United States Patent
Webster et al.

(10) Patent No.: US 12,352,625 B2
(45) Date of Patent: Jul. 8, 2025

(54) AUTOMATED CONTROL OF CELL CULTURE USING RAMAN SPECTROSCOPY

(71) Applicant: Lonza Ltd, Visp (CH)

(72) Inventors: Thaddaeus Webster, Rollinsford, NH (US); Brian Hadley, Dover, NH (US); Carrie Mason, Brentwood, NH (US); Colin Jaques, London (GB); Seshu Tummala, Newburyport, MA (US); Ruth Christine Rowland-Jones, Chelmsford (GB); Yonatan Levinson, Silver Spring, MD (US); Nicholas Uth, Washington, DC (US); Pankaj Sinha, Alpharetta, GA (US); Eytan Abraham, Potomac, MD (US)

(73) Assignee: Lonza Ltd, Visp (CH)

( * ) Notice: Subject to any disclaimer, the term of this patent is extended or adjusted under 35 U.S.C. 154(b) by 0 days.

(21) Appl. No.: 18/171,438

(22) Filed: Feb. 20, 2023

(65) Prior Publication Data
US 2023/0204421 A1    Jun. 29, 2023

Related U.S. Application Data

(63) Continuation of application No. 16/152,950, filed on Oct. 5, 2018, now Pat. No. 11,609,120.
(Continued)

(51) Int. Cl.
*G01J 3/44* (2006.01)
*C12M 1/00* (2006.01)
(Continued)

(52) U.S. Cl.
CPC .............. *G01J 3/44* (2013.01); *C12M 31/08* (2013.01); *C12M 41/32* (2013.01); *C12M 41/36* (2013.01);
(Continued)

(58) Field of Classification Search
CPC ... G01J 3/44; G01N 21/65; G01N 2021/8411; C12M 31/08; C12M 41/30; C12M 41/32;
(Continued)

(56) References Cited

U.S. PATENT DOCUMENTS

| 5,656,491 A | 8/1997 | Cassani et al. |
| 6,168,941 B1 * | 1/2001 | Liu ........................ C12N 15/86 |
| | | 435/235.1 |

(Continued)

FOREIGN PATENT DOCUMENTS

| CN | 101443444 A | 5/2009 |
| JP | 2005337777 | 12/2005 |

(Continued)

OTHER PUBLICATIONS

Matthews, T.E. et al., Closed loop control of lactate concentration in mammalian cell culture by Raman spectroscopy leads to improved cell density, viability, and biopharmaceutical protein production. Biotechnol. Bioeng., 113: 2416-2424. https://doi.org/10.1002/bit.26018 (Year: 2016).*

(Continued)

*Primary Examiner* — Kara E. Geisel
*Assistant Examiner* — Jonathon Cook
(74) *Attorney, Agent, or Firm* — Dority & Manning, P.A.

(57) ABSTRACT

The monitoring and control of bioprocesses is provided. The present disclosure provides the ability to generate generic calibration models, independent of cell line, using inline Raman probes to monitor changes in glucose, lactate, glutamate, ammonium, viable cell concentration (VCC), total cell concentration (TCC) and product concentration. Calibration models were developed from cell culture using two different CHOK1SV GS-KO™ cell lines producing different monoclonal antibodies (mAbs). Developed predictive models, qualified using an independent CHOK1SV GS-KO™

(Continued)

cell line not used in calibration, measured changes in glucose, lactate, ammonium, VCC, and TCC with minor prediction errors over the course of cell culture with minimal cell line dependence. The development of these generic models allows the application of spectroscopic PAT techniques in a clinical manufacturing environment, where processes are typically run once or twice in GMP manufacturing based on a common platform process.

20 Claims, 28 Drawing Sheets

Related U.S. Application Data

(60) Provisional application No. 62/569,076, filed on Oct. 6, 2017, provisional application No. 62/569,190, filed on Oct. 6, 2017.

(51) Int. Cl.

| | | |
|---|---|---|
| *C12M 1/34* | (2006.01) | |
| *C12M 1/36* | (2006.01) | |
| *C12N 5/0735* | (2010.01) | |
| *C12N 5/0783* | (2010.01) | |
| *G01N 21/65* | (2006.01) | |
| *G01N 21/84* | (2006.01) | |

(52) U.S. Cl.
CPC .......... *C12M 41/48* (2013.01); *C12N 5/0606* (2013.01); *C12N 5/0636* (2013.01); *G01N 21/65* (2013.01); *G01N 2021/8411* (2013.01); *G01N 2201/129* (2013.01)

(58) Field of Classification Search
CPC ..... C12M 41/36; C12M 41/48; C12N 5/0606; C12N 5/0636
See application file for complete search history.

(56) References Cited

U.S. PATENT DOCUMENTS

| | | |
|---|---|---|
| 6,544,424 B1 | 4/2003 | Sheivitz |
| 6,803,020 B1 | 10/2004 | Agnely et al. |
| 7,330,746 B2 | 2/2008 | Demuth et al. |
| 7,629,167 B2 | 12/2009 | Hodge et al. |
| 8,298,054 B2 | 10/2012 | Hodge et al. |
| 8,318,416 B2 | 11/2012 | Tsang et al. |
| 8,355,767 B2 | 1/2013 | Hunter et al. |
| 8,771,635 B2 | 7/2014 | Mohtadi et al. |
| 9,109,193 B2 | 8/2015 | Galliher et al. |
| 9,212,379 B2 | 12/2015 | Tsang et al. |
| 9,260,695 B2 | 2/2016 | Crowley et al. |
| 9,388,373 B2 | 7/2016 | Rao et al. |
| 9,568,449 B2 | 2/2017 | Downey et al. |
| 9,650,412 B2 | 5/2017 | Konstantinov et al. |
| 9,670,446 B2 | 6/2017 | Khan |
| 9,670,520 B2 | 6/2017 | Zijlstra et al. |
| 10,118,149 B2 | 11/2018 | Reintjens et al. |
| 10,214,718 B2 | 2/2019 | Berteau et al. |
| 10,544,395 B2 | 1/2020 | Hiller et al. |
| 11,104,875 B2 | 8/2021 | Hiller et al. |
| 11,292,829 B2 | 4/2022 | Follstad et al. |
| 11,452,797 B2 | 9/2022 | Ross |
| 2004/0259240 A1* | 12/2004 | Fadden ................ C12M 47/10 435/261 |
| 2005/0054101 A1* | 3/2005 | Felder .................. C12M 25/16 435/383 |
| 2006/0019333 A1 | 1/2006 | Rodgers et al. |
| 2006/0199260 A1 | 9/2006 | Zhang et al. |
| 2009/0048816 A1 | 2/2009 | Srinivasa |
| 2009/0104594 A1 | 4/2009 | Webb |
| 2009/0305626 A1 | 12/2009 | Hope |
| 2011/0060463 A1 | 3/2011 | Selker |
| 2012/0077429 A1 | 3/2012 | Wernimont et al. |
| 2013/0017577 A1 | 1/2013 | Arunakumari et al. |
| 2014/0185033 A1 | 7/2014 | Moretto |
| 2014/0295532 A1 | 10/2014 | Ray et al. |
| 2015/0210971 A1 | 7/2015 | Baskar et al. |
| 2015/0219622 A1 | 8/2015 | Hickman |
| 2015/0247210 A1 | 9/2015 | Olesberg et al. |
| 2015/0299638 A1 | 10/2015 | Shimoni et al. |
| 2016/0025633 A1 | 1/2016 | Moretto et al. |
| 2016/0145563 A1 | 5/2016 | Berteau et al. |
| 2016/0161478 A1* | 6/2016 | Sulya ................ G01N 33/54386 435/7.1 |
| 2016/0244725 A1 | 8/2016 | Lawrence |
| 2016/0289633 A1 | 10/2016 | Yang et al. |
| 2016/0341667 A1 | 11/2016 | Ramasubramanyan et al. |
| 2017/0009269 A1 | 1/2017 | Ozturk |
| 2017/0114381 A1 | 4/2017 | Goudar |
| 2017/0130186 A1 | 5/2017 | Berry et al. |
| 2017/0355947 A9 | 12/2017 | Berry et al. |
| 2018/0171279 A1 | 6/2018 | Hiller et al. |
| 2018/0171294 A1* | 6/2018 | Czerniecki ........... C12N 5/0636 |
| 2018/0291329 A1 | 10/2018 | Moretto et al. |
| 2018/0312802 A1 | 11/2018 | Bielser et al. |
| 2019/0112569 A1 | 4/2019 | Czeterko et al. |
| 2019/0137338 A1 | 5/2019 | Webster et al. |
| 2019/0153381 A1 | 5/2019 | Angelini et al. |

FOREIGN PATENT DOCUMENTS

| | | |
|---|---|---|
| WO | WO2005084696 | 9/2005 |
| WO | WO2016004322 A2 | 1/2016 |
| WO | WO2016196315 A2 | 12/2016 |
| WO | WO2018188395 | 10/2018 |

OTHER PUBLICATIONS

Gregory N. Bancroft, Vassilios I. Sikavitsas, and Antonios G. Mikos. Technical Note: Design of a Flow Perfusion Bioreactor System for Bone Tissue-Engineering Applications. Tissue Engineering. Jun. 2003.549-554.http://doi.org/10.1089/107632703322066723 (Year: 2003).*

Ozturk SS, Thrift JC, Blackie JD, Naveh D. Real-time monitoring and control of glucose and lactate concentrations in a mammalian cell perfusion reactor. Biotechnol Bioeng. Feb. 20, 1997;53(4):372-8. doi: 10.1002/(SICI)1097-0290(19970220)53:4<372::AID-BIT3>3.0.CO;2-K. PMID: 18634025. (Year: 1997).*

Matthews, T.E., Berry, B.N., Smelko, J., Moretto, J., Moore, B. and Wiltberger, K. , Closed loop control of lactate concentration in mammalian cell culture by Raman spectroscopy leads to improved cell density, viability, and biopharmaceutical protein production. Biotechnol. Bioeng., 113: 2416-2424 (Year: 2016).*

Abdul-Aziz, Z., Z. Wahid, and a. V. Metcalfe. n.d. "Using 'Design of experiments' to overcome limitation of 'One-Variable-At-A-Time' approach to experimentation; the case of a rubber glove manufacturing facility in Malaysia." Proceedings of the 5th Biannual World Automation Congress 487-93. Retrieved http://ieeexplore.ieee.org/Ipdocs/epic03/Wrapper.htm?arnumber=1049485.

Abu-Absi, Nicholas R. et al. 2011. "Real time monitoring of multiple parameters in mammalian cell culture bioreactors using an in-line Raman spectroscopy probe." *Biotechnology and bioengineering* 108(5):1215-21. Retrieved Jun. 7, 2013 http://www.ncbi.nim.nih.gov/pubmed/21449033.

Ahn, Woo Suk, Jae-Jin Jeon, Yeong-Ran Jeong, Seung Joo Lee, and Sung Kwan Yoon. 2008. "Effect of culture temperature on erythropoietin production and glycosylation in a perfusion culture of recombinant CHO cells." Biotechnology and bioengineering 101(6):1234-44. Retrieved Mar. 7, 2016 http://www.ncbi.nlm.nih.gov/pubmed/18980186.

Analysis of a Batch Fermentation Process; Kaiser Optical Systems Inc.

Application Note. Analysis of a Mammalian Cell Culture; Kaiser Ogtical Systems Inc. Application Note.

Anderson, C. A., and R. Bro. 2000. "The N-way Toolbox for Matlab." *Chemometrics and Intelligent Laboratory Systems* 52(1):1-4. Retrieved http://www.models.life.ku.dk/source/nwaytoolbox/.

(56) References Cited

OTHER PUBLICATIONS

Anderson, Rosaleen J., David J. Bendell, and Paul W. Groundwater. 2004b. "Ultraviolet-Vis Spectroscopy." pp. 9-10 in *Organic Spectroscopic Analysis*. The Royal Society of Chemistry.

Anderson-Cook, Christine M., Connie M. Borror, and Douglas C. Montgomery. 2009. "Response surface design evaluation and comparison." *Journal of Statistical Planning and Inference* 139(2):629-41. Retrieved Jan. 3, 2017 http://linkinghub.elsevier.com/retrieve/pii/S0378375808001572.

André, Silvère et al. 2015. "In-line and real-time prediction of recombinant antibody titer by in situ Raman spectroscopy." *Analytica chimica acta* 892:148-52. Retrieved Dec. 18, 2015 http://www.ncbi.nlm.nih.gov/pubmed/26388485.

Arnold, S. Alison, John Crowley, Nigel Woods, Linda M. Harvey, and Brian McNeil. 2003. "In-situ near infrared spectroscopy to monitor key analytes in mammalian cell cultivation." *Biotechnology and bioengineering* 84(1):13-19. Retrieved Jul. 26, 2013 http://www.nobl.nlm.nih.gov/pubmed/12910538.

Ashton, Lorna et al. 2013. "The challenge of applying Raman spectroscopy to monitor recombinant antibody production." *The Analyst* 138(22):6977-85. Retrieved Feb. 9, 2016 http://www.ncbi.nlm.nih.gov/pubmed/24093128.

Bahram, Morteza, Rasmus Bro, Colin Stedmon, Abbas Afkhami, and Dk-Roskilde. 2007. "Handling of Rayleigh and Raman scatter for PARAFAC modeling of fluorescence data using interpolation." *Journal of Chemometrics* (*in press*).

Banwell, C. N. 1972. "Infra-Red Spectroscopy." pp. 65-119 in *Fundamentals of Molecular Spectroscopy*, edited by P Sykes. McGraw-Hill Book Company (UK) Limited.

Beckman Coulter Inc. 2013. "Vi-CELL XR Bioprocess Tracking." Retrieved https://www.beckmancoulter.com/wsrportal/bibliography?docname=BR-18086.pdf.

Berry, Brandon, Justin Moretto, Thomas Matthews, John Smelko, and Kelly Wiltberger. 2014. "Cross-scale predictive modeling of CHO cell culture growth and metabolites using Raman spectroscopy and multivariate analysis." *Biotechnology progress* 31(2):566-77. Retrieved May 26, 2016 (http://www.ncbi.nlm.nih.gov/pubmed/25504860).

Berry, Brandon N. et al. 2015. "Quick generation of Raman spectroscopy based in-process glucose control to influence biopharmaceutical protein product quality during mammalian cell culture." *Biotechnology progress* 32(1):224-34. Retrieved Jul. 22, 2016 http://www.ncbi.nim.nih.gov/pubmed/26587969.

Betts, Jonathan I., and Frank Baganz. 2006. "Miniature bioreactors: current practices and future opportunities." *Microbial cell factories* 5:21. Retrieved Nov. 7, 2013 http://www.pubmedcentral.nih.gov/articlerender.fcgi?artid=1523360&tool=pmcentrez&rendertype=abstract.

Biechele, Philipp, Christoph Busse, Dörte Solle, Thomas Scheper, and Kenneth Reardon. 2015. "Sensor systems for bioprocess monitoring." *Engineering in Life Sciences* 15(5):469-88. Retrieved Apr. 5, 2016 http://doi.wiley.com/10.1002/elsc.201500014.

Birch, John R., and Andrew J. Racher. 2006. "Antibody production." *Advanced drug delivery reviews* 58(5-6):671-85. Retrieved May 28, 2013 http://www.nobi.nim.nih.gov/pubmed/16822577.

Bridwell, Heather, Vikas Dhingra, Daniel Peckman, and Jennifer Roark. 2010. "Perspectives on Method Validation : Importance of Adequate Method Validation." *The Quality Assurance Journal* 13(3-4):72-77.

Bro, Rasmus. 1996. "Multiway calibration. multilinear pls." *Journal of Chemometrics* 10:47-61.

Bro, Rasmus. 1997. "PARAFAC. Tutorial and applications." *Chemical Engineering Research and Design* 38:149-71.

Bro, Rasmus. 1998. "Core Consistency." pp. 113-121 in *Multi-Way Analysis in the Food Industry. PhD Thesis*. Amsterdam.

Bro, Rasmus, and Charlotte M. Andersen. 2003. "Theory of net analyte signal vectors in inverse regression." *Journal of Chemometrics* 17(12):646-52. Retrieved Aug. 1, 2016 http://doi.wiley.com/10.1002/cem.832.

Bro, Rasmus, and Henk a. L. Kiers. 2003. "A new efficient method for determining the number of components in PARAFAC models." *Journal of Chemometrics* 17(5):274-86. Retrieved May 13, 2015 http://doi.wiley.com/10.1002/cem.801.

Bro, Rasmus, and Age K. Smilde. 2014. "Principal Component Analysis." *Analytical Methods* 6:2812-31.

Bruhlmann, David et al. 2015. "Tailoring recombinant protein quality by rational media design." *Biotechnology progress* 31(3):615-29. Retrieved Oct. 5, 2016 http://www.ncbi.nlm.nih.gov/pubmed/25864704.

Buchs, J. 2001. "Introduction to advantages and problems of shaken cultures." *Biochemical engineering journal* 7(2):91-98. Retrieved http://www.ncbi.nim.nih.gov/pubmed/11173295.

Buckley et al. "Applications of Raman Spectroscopy in Biopharmaceutical Manufacturing: A Short Review," Applied Spectroscopy, 2017 vol. 71(6), pp. 1085-1116.

Bumbrah, Gurvinder Singh, and Rakesh Mohan Sharma. 2016. "Raman spectroscopy—Basic principle, instrumentation and selected applications for the characterization of drugs of abuse." *Egyptian Journal of Forensic Sciences* 6(3):209-15. Retrieved Nov. 22, 2016 http://linkinghub.elsevier.com/retrieve/pii/S2090536X15000477.

Butler, Michael. 2005. "Hybridomas—source of antibodies." pp. 151-174 in *Animal Cell Culture and technology*. Garland Science/BIOS Scientific Publishers.

Cacciatore, Jonathan J., Lawrence a Chasin, and Edward F. Leonard. 2010. "Gene amplification and vector engineering to achieve rapid and high-level therapeutic protein production using the Dhfr-based CHO cell selection system." *Biotechnology Advances* 28(6):673-81.

Calvet, Amandine, Boyan Li, and Alan G. Ryder. 2014. "A rapid fluorescence based method for the quantitative analysis of cell culture media photo-degradation." *Analytica chimica acta* 807:111-19. Retrieved Jul. 28, 2014 http://www.ncbi.nlm.nih.gov/pubmed/24356227.

CAMO Software AS. 2016. "Classical DOE Methods and PLS-ANOVA." Retrieved Nove. 2, 1BC http://www.camo.com/resources/classical-doe-methods-plsanova.html.

Capito, Florian, Aline Zimmer, and Romas Skudas. 2015. "Mid-infrared spectroscopy-based analysis of mammalian cell culture parameters." *Biotechnology progress* 31(2):578-84. Retrieved Aug. 9, 2016 http://www.ncbi.nlm.nih.gov/pubmed/25504543.

Carter, Paul J. 2011. "Introduction to current and future protein therapeutics: a protein engineering perspective." *Experimental cell research* 317(9):1261-69. Retrieved May 23, 2014 http://www.ncbi.nlm.nih.gov/pubmed/21371474.

Chaplin, Martin. 2013. "Enzyme Technology." Retrieved Jul. 16, 2014 http://www1.lsbu.ac.uk/water/enztech/amperometric.html.

ChemAxon Ltd. n.d. "Chemicalize platform." Retrieved http://www.chemicalize.org.

Chon, John H., and Gregory Zarbis-Papastoitsis. 2011. "Advances in the production and downstream processing of antibodies." *New biotechnology* 28(5):458-63. Retrieved Oct. 6, 2016 http:/www.ncbi.nlm.nith.gov/pubmed/21515428.

Christopher B. Lewis, Roger J. McNichols, Ashok Gowda and Gerard L. Cote. 2000. "Investigation of Near-Infrared Spectroscopy for Periodic Determination of Glucose in Cell Culture Media in Situ." *Applied Spectroscopy* 54(10):1453-57.

Clayden, Jonathan, Nick Greeves, Stuart Warren, and Peter Wothers. 2001. "Infrared Spectra." pp. 65-78 in *Organic Chemistry*. Oxford University Press Inc.

Comparison of Spectroscopy Technologies for Improved Monitoring of Cell Culture Processes in Miniature Bioreactors; Rowland-Jones; 1Newcastle University, 2Lonza, 3University of Copenhagen, 4University of Leeds. Published in Biotechnology Progress.

Correa, Elon et al. 2012. "Rapid reagentless quantification of alginate biosynthesis in Pseudomonas fluorescens bacteria mutants using FT-IR spectroscopy coupled to multivariate partial least squares regression." *Analytical and bioanalytical chemistry* 403(9):2591-99. Retrieved Apr. 12, 2013 http://www.ncbi.nim.nih.gov/pubmed/22585056.

Cozzolino, D., and C. Curtin. 2012. "The use of attenuated total reflectance as tool to monitor the time course of fermentation in wild

(56) References Cited

OTHER PUBLICATIONS ferments." *Food Control* 26(2):241-46. Retrieved Apr. 12, 2013 http://linkinghub.elsevier.com/retrieve/pii/S0956713512000801.
Craven, Stephen, Jessica Whelan, and Brian Glennon. 2014. "Glucose concentration control of a fed-batch mammalian cell bioprocess using a nonlinear model predictive controller." *Journal of Process Control* 24(4):344-57. Retrieved Jul. 22, 2016 http://linkinghub.elsevier.com/retrieve/pii/S0959152414000584.
Craven Stephen et al: "Glucose concentration control of a fed-batch mammalian cell bioprocess using a nonlinear model predictive controller", Journal of Process Control, vol. 24, No. 4, Mar. 21, 2014, pp. 344-357.
Cross-scale In Situ Raman Monitoring of a Cell Culture Bioprocess; Kaiser Optical Systems Inc. Application Note.
Cross-Scale Predictive Modeling of CHO Cell Culture Growth and Metabolities Using Raman Spectroscopy and Multivariate Analysis; Berry et al.; Published in Biotechnology Progress.
Cruz, H. J., C. M. Freitas, P. M. Alves, J. L. Moreira, and M. J. T. Carrondo. 2000. "Effects of ammonia and lactate on growth , metabolism , and productivity of BHK cells ." *Enzyme and Microbial Technology* 27:43-52.
Dean, Jason, and Pranhitha Reddy. 2013. "Metabolic analysis of antibody producing CHO cells in fed-batch production." *Biotechnology and bBoengineering* 110(6):1735-47. Retrieved Oct. 19, 2016 http://www.ncbi.nlm.nih.gov/pubmed/23296898.
Devos, Olivier, and Ludovic Duponchel. 2011. "Parallel genetic algorithm co-optimization of spectral pre-processing and wavelength selection for PLS regression." *Chemometrics and Intelligent Laboratory Systems* 107(1):50-58. Retrieved Jul. 17, 2013 http://linkinghub.elsevier.com/retrieve/pii/S0169743911000116.
Ecker, Dawn M., Susan Dana Jones, and Howard L. Levine. 2015. "The therapeutic monoclonal antibody market." *mAbs* 7(1):9-14. Retrieved Oct. 5, 2016 http://www.pubmedcentral.nih.gov/articlerender.fcgi?artid=4622599&tool=pmcentrez& rendertype=abstract.
Eigenvector Research Inc. 2011. "Advanced Spectral Preprocessing: Sample Normnalization." Eigenvector University. Retrieved Jan. 23, 2017 http:/wiki.eigenvector.com/index.php?title=Advanced_ Preprocessing:_Sample_Normalization.
Eigenvector Research Inc. 2012. "T-Squared Q residuals and Contributions." Retrieved Aug. 18, 2014 http://wiki.eigenvector.com/index.php?title=TSquared_Q_residuals_and_Contributions.
Eigenvector Research Inc. 2013a. "Advanced Preprocessing: Noise, Offset, and Baseline Filtering." Retrieved Jan. 23, 2017 http://wiki.eigenvector.com/index.php?title=Advanced_Preprocessing:_Noise,_Offset,_and_Baseline_Filtering.
Eigenvector Research Inc. 2013b. "Cross-Validation." Retrieved Aug. 4, 2014 http://wiki.eigenvector.com/index.php?title=Using_ Cross-Validation.
Eigenvector Research Inc. 2013c. "SRatio." Retrieved Aug. 7, 2014 http://wiki.eigenvector.com/index.php?title=Sratio.
Eigenvector Research Inc. 2014a. "Clustering and Classification." in *Eigenvector University*.
Eigenvector Research Inc. 2014b. "Vip." Retrieved Aug. 7, 2014 http://wiki.eigenvector.com/index.php?title=Vip.
Elvin, John G., Ruairidh G. Couston, and Christopher F. van der Walle. 2013. "Therapeutic antibodies: market considerations, disease targets and bioprocessing." *International journal of pharmaceutics* 440(1):83-98. Retrieved Oct. 5, 2016 http://www.ncbi.nlm.nih.gov/pubmed/22227342.
Eriksson, L. et al. 2006. "PCA." pp. 39-62 in *Multi- and Megavariate Data Analysis. Part 1 Basic Principles and Applications*. Umetrics AB.
Esquerre, C., a. a. Gowen, J. Burger, G. Downey, and C. P. O'Donnell. 2012. "Suppressing sample morphology effects in near infrared spectral imaging using chemometric data pre-treatments." *Chemometrics and Intelligent Laboratory Systems* 117:129-37. Retrieved Jul. 17, 2013 http://linkinghub.elsevier.com/retrieve/pii/S0169743912000408.
European Medicines Agency. 2011. *ICH guideline Q11 on development and manufacture of drug substances (chemical entities and biotechnological / biological entities) ICH guideline Q11 on development and manufacture of drug substances (chemical entities and biotechnological / biological*.
Ewanick, Shannon M., Wesley J. Thompson, Brian J. Marquardt, and Renata Bura. 2013. "Real-time understanding of lignocellulosic bioethanol fermentation by Raman spectroscopy." *Biotechnology for biofuels* 6(1):28. Retrieved Apr. 12, 2013 http://www.biotechnologyforbiofuels.com/content/6/1/28.
Faassen, Saskia M., and Bernd Hitzmann. 2015. "Fluorescence spectroscopy and chemometric modeling for bioprocess monitoring." *Sensors* (Basel, Switzerland) 15(5): 10271-91. Retrieved Jul. 22, 2016 http://www.pubmedcentral.nih.gov/articlerender.fcgi?artid=4481931&tool=pmcentrez&rendertype=abstract.
FDA. 2004. *Guidance for Industry PAT—A Framework for Innovative Pharmaceutical Development, Manufacturing, and Quality Assurance*.
Ferré, Joan, and Nicolaas (Klaas) M. Faber. 2003. "Net analyte signal calculation for multivariate calibration." *Chemometrics and Intelligent Laboratory Systems* 69(1-2):123-36. Retrieved Aug. 1, 2016 http://linkinghub.elsevier.com/retrieve/pii/S0169743903001187.
Franco, Vanina G., Juan C. Perin, Victor E. Mantovani, and Héctor C. Goicoechea. 2006. "Monitoring substrate and products in a bioprocess with FTIR spectroscopy coupled to artificial neural networks enhanced with a genetic-algorithm-based method for wavelength selection." *Talanta* 68(3):1005-12. Retrieved Mar. 14, 2013 http://www.nobl.nim.nih.gov/pubmed/18970424.
Geladi, Paul. 2002. "Some recent trends in the calibration literature." 60:211-24.
Geladi, Paul, and Bruce R. Kowalski. 1986. "Partial least-squares regression: a tutorial." *Analytica Chimica Acta* 186:1-17.
Generic Raman-Based Calibration Models Enabling Real-Time Monitoring of Cell Culture Bioreactors; Mehdizadeh et al.; Pfizer . Published in Biotechnology Progress.
Gronemeyer, Petra, Reinhard Ditz, and Jochen Strube. 2014. "Trends in Upstream and Downstream Process Development for Antibody Manufacturing." *Bioengineering* 1(4):188-212. Retrieved Oct. 5, 2016 http://www.mdpi.com/2306-5354/1/4/188/.
Hakemeyer, Christian et al. 2012. "At-line NIR spectroscopy as effective PAT monitoring technique in Mab cultivations during process development and manufacturing." *Talanta* 90:12-21. Retrieved Dec. 1, 2016 http://www.nobi.nim.nih.gov/pubmed/22340110.
Hasuer, Hansjorg, and Roland Wagner. 2015. "Introduction." pp. 1-10 in *Animal Cell Biotechnology in Biologics Production*, edited by Hansjorg Hasuer and Roland Wagner. Walter de Gruyter GmbH, Berlin.
Hisiger, Steve, and Mario Jolicoeur. 2005. "A multiwavelength fluorescence probe: is one probe capable for on-line monitoring of recombinant protein production and biomass activity?" *Journal of biotechnology* 117(4):325-36. Retrieved Jul. 28, 2014 http://www.ncbi.nlm.nih.gov/pubmed/15890426.
Hofkens, J., and J. Enderlein. 2011. "Basic Principles of Fluorescence Spectroscopy." pp. 1-30 in *Handbook of Fluorescence Spectroscopy and Imaging*. Wiley-VCH.
How to Develop and Implement Raman Glucose Control for Biomanufacturing Mammalian Cell Culture Processes; Smellko, 1Biogen, Inc. Presented at SCIX2017.
Huang, Jun, Saly Romero-Torres, and Mojgan Moshgbar. 2010. "Practical Considerations in Data Pre-treatment for NIR and Raman Spectroscopy." *American Pharmaceutical Review*. Retrieved http://www.americanpharmaceuticalreview.com/Featured-Articles/116330-Practical-Considerations-in-Data-Pre-treatment-for-NIR-and-Raman-Spectroscopy/.
Lan R. Lewis, Howell Edwards. 2001. "Raman Spectroscopy and its Adaptation to the Industrial Environment." p. 93 in *Handbook of Raman Spectroscopy: From the Research Laboratory to the Process Line (Practical Spectroscopy)*. Marcel Dekker, Inc.
ICH Harmonised Tripartite Guideline. 2005. "Validation of analytical procedures: text and methodology (Q2) R1."
ICH Harmonised Tripartite Guideline. 2009. "Guidance for Industry: Q8(R2) Pharmaceutical Development." 8 (November).
Jain, Garima, Guhan Jayaraman, Öznur Kokpinar, Ursula Rinas, and Bernd Hitzmann. 2011. "On-line monitoring of recombinant bacterial cultures using multi-wavelength fluorescence spectros-

(56) References Cited

OTHER PUBLICATIONS copy." *Biochemical Engineering Journal* 58-59:133-39. Retrieved Jul. 28, 2014 http://linkinghub.elsevier.com/retrieve/pii/S1369703X11002373.

Janakiraman, Vijay, Chris Kwiatkowski, Rashmi Kshirsagar, Thomas Ryll, and Yao-Ming Huang. 2015. "Application of high-throughput mini-bioreactor system for systematic scale-down modeling, process characterization, and control strategy development." *Biotechnology progress* 31(6):1623-32. Retrieved Aug. 8, 2016 http://www.nobl.nlm.nih.gov/pubmed/26317495.

Jayapal, Karthik P., Katie F. Wlaschin, Wei-Shou Hu, and Miranda G. S. Yap. 2007. "Recombinant Protein Therapeutics from CHO Cells—20 Years and Counting." *CHO Consortium: SBE Special Section* 40-47.

Jenkins, Nigel, Lisa Murphy, and Ray Tyther. 2008. "Post-translational modifications of recombinant proteins: significance for biopharmaceuticals." *Molecular biotechnology* 39(2):113-18. Retrieved Oct. 5, 2016 http://www.ncbi.nlm.nih.gov/pubmed/18327554.

Jessica Whelan et al: "In situ Raman spectroscopy for simultaneous monitoring of multiple process parameters in mammalian cell culture bioreactors", Biotechnology Progress, vol. 28. No. 5, Jul. 20, 2012, pp. 1355-1362.

Jørgensen, Anna. 2000. "C Lustering Excipient Near Infrared Spectra Using Different Chemometric Seminar summary."

Jose, Gledson E. et al. 2011. "Predicting Mab product yields from cultivation media components, using near-infrared and 2D-fluorescence spectroscopies." *Biotechnology progress* 27(5):1339-46. Retrieved Mar. 3, 2013 http://www.ncbi.nlm.nih.gov/pubmed/21618724.

Kantardjieff, Anne, and Weichang Zhou. 2014. *Mammalian cell cultures for biologics manufacturing.* Retrieved http://www.ncbi.nim.nih.gov/pubmed/24258145.

King, David J. 1998. "Preparation, structure and function of monoclonal antibodies." pp. 1-25 in *Applications and Engineering of Monoclonal Antibodies.*

L.Eriksson, E.Johansson, N. Kettaneh-Wold, J. Trygg, C. Wikstrom, S. Wold. 2006a. "Classifcation and Discimination." pp. 171-194 in *Multi- and Megavariate Data Analysis. Part 1 Basica Principles and Applications.* Umetrics AB.

L.Eriksson, E.Johansson, N. Kettaneh-Wold, J. Trygg, C. Wikstrom, S. Wold. 2006b. "PLS." pp. 63-101 in *Multi- and Megavariate Data Analysis. Part 1 Basica Principles and Applications.* Umetrics AB.

Lai, Tingfeng, Yuansheng Yang, and Say Kong Ng. 2013. "Advances in Mammalian cell line development technologies for recombinant protein production." *Pharmaceuticals* 6(5):579-603. Retrieved Oct. 6, 2016 http://www.pubmedcentral.nih.gov/articlerender.fcgi?artid=3817724&tool=pmcentrez&rendertype=abstract.

Lao, Mio-sam, and Derek Toth. 1997. "Effects of Ammonium and Lactate on Growth and Metabolism of a Recombinant Chinese Hamster Ovary Cell Culture." *Biotechnolology Progress* 13:688-91.

Larkin, Peter. 2011a. "Basic Principles." pp. 7-26 in *Infrared and Raman Spectroscopy; Principles and Spectral Interpretation.* Elsevier.

Larkin, Peter. 2011b. "Instumentation and Sampling Methods." pp. 27-54 in *Infrared and Raman Spectroscopy; Principles and Spectral Interpretation.* Elsevier.

Lasch, Peter. 2012. "Spectral pre-processing for biomedical vibrational spectroscopy and microspectroscopic imaging." *Chemometrics and Intelligent Laboratory Systems* 117:100-114. Retrieved Jul. 17, 2013 http:/linkinghub.elsevier.com/retrieve/pil/S0169743912000561.

Leader, Benjamin, Quentin J. Baca, and David E. Golan. 2008. "Protein therapeutics: a summary and pharmacological classification." *Nature reviews. Drug discovery* 7(1):21-39. Retrieved http://www.nobi.nlm.nih.gov/pubmed/18097458.

Lee, Hae Woo, Andrew Christie, Jin Xu, and Seongkyu Yoon. 2012. "Data fusion-based assessment of raw materials in mammalian cell culture." *Biotechnology and bioengineering* 109(11):2819-28. Retrieved Jul. 25, 2016 http://www.ncbi.nim.nih.gov/pubmed/22566239.

Leys, Christophe, Christophe Ley, Olivier Klein, Philippe Bernard, and Laurent Licata. 2013. "Detecting outliers: Do not use standard deviation around the mean, use absolute deviation around the median." *Journal of Experimental Social Psychology* 49(4):764-66. Retrieved Nov. 26, 2014 http://linkinghub.elsevier.com/retrieve/pii/S0022103113000668.

Li, Boyan et al. 2010. "Rapid Characterization and Quality Control of Complex Cell Culture Media Solutions Using Raman Spectroscopy and Chemometrics." 107(2):290-301.

Li, Boyan, Michael Shanahan, Amandine Calvet, Kirk J. Leister, and Alan G. Ryder. 2014. "Comprehensive, quantitative bioprocess productivity monitoring using fluorescence EEM spectroscopy and chemometrics." *The Analyst* 139(7):1661-71. Retrieved Jul. 22, 2016 http://www.ncbi.nlm.nih.gov/pubmed/24504094.

Li, Feng, Natarajan Vijayasankaran, Amy (Yijuan) Shen, Robert Kiss, and Ashraf Amanullah. 2010. "Cell culture processes for monoclonal antibody production." *mAbs* 2(5):466-79.Retrieved Oct. 5, 2016 http://www.tandfonline.com/doi/abs/10.4161/mabs.2.5.12720.

Li, Ying-Sing, and Jeffrey S. Church. 2014. "Raman spectroscopy in the analysis of food and pharmaceutical nanomaterials." *Journal of food and drug analysis* 22(1):29-48. Retrieved Jun. 11, 2015 http://www.ncbi.nlm.nih.gov/pubmed/24673902.

Lin, Mengshi, Barabara A. Rasco, Anna G. Cavinato, and Murad Al-Holy. 2009. "Infrared Spectroscopy—Near Infrared Spectrscopy and Mid-Infrared Spectroscopy." pp. 119-141 in *Infrared Spectroscopy for Food Quality Analysis and Control.* Elsevier Inc.

Lindemann, C., S. Marose, H. O. Nielsen, and T. Scheper. 1998. "Two-dimensional fluorescence spectroscopy for on-line bioprocess monitoring." *Biotechnology progress* 14(1):63-74. Retrieved http://www.nebi.nlm.nih.gov/pubmed/9496670.

Liu, Hui F., Junfen Ma, Charles Winter, and Robert Bayer. 2010. "Recovery and purification process development for monoclonal antibody production." *mAbs* 2(5):480-99. Retrieved Oct. 6, 2016 http://www.tandfonline.com/doi/abs/10.4161/mabs.2.5.12645.

Lonza. n.d. "Media and Feed—Overview of Process Platforms for GS." Retrieved Mar. 7, 2016 http://www.lonza.com/custom-manufacturing/development-technologies/gs-geneexpression-system/additional-qs-kits-and-services/media-and-feeds.aspx.

Louis, Kristine S., and Andre C. Siegel. 2011. "Chapter 2. Cell Viability Analysis Using Trypan Blue: Manual and Automated Methods." pp. 7-12 in *Mammalian Cell Viability*, vol. 740, edited by Martin J. Stoddart. Totowa, NJ: Humana Press. Retrieved Nov. 1, 2016 http://link.springer.com/10.1007/978-1-61779-108-6.

M.S. Dhonoa, S.J. Lister, R. Sanderson and R. J. Barnes. 1994. "The link between MSC and SNV transformations of NIR spectra." *Near Infrared Spectroscopy* 2:43-47.

Machin, Marianna, Lorenz Liesum, and Antonio Peinado. 2011. "The FDA 's PAT Initiative, past and present Using miRNA manipulation as an Supplement Implementation of Modelling Approaches in The QbD Framework : Examples From the Novartis." (6).

Maggio, Rubén M. et al. 2009. "Monitoring of fatty acid composition in virgin olive oil by Fourier transformed infrared spectroscopy coupled with partial least squares." *Food Chemistry* 114(4):1549-54. Retrieved Aug. 1, 2016 http://linkinghub.elsevier.com/retrieve/pli/S0308814608013757.

Mammalian Cell Culture Monitoring Using in Situ Spectroscopy: Is Your Method Really Optimised ?; Andre et al.; Universite de Lille. Published in Biotechnology Progress.

Massarini, Enrico et al. 2015. "Methodologies for assessment of limit of detection and limit of identification using surface-enhanced Raman spectroscopy." *Sensors and Actuators B: Chemical* 207(February): 437-46. Retrieved May 25, 2016 http://linkinghub.elsevier.com/retrieve/pii/S0925400514012064.

Matthews, Thomas E et al. 2016. "Closed loop control of lactate concentration in mammalian cell culture by Raman spectroscopy leads to improved cell density, viability and biopharmaceutical protein production." *Biotechnology and Bioengineering* 9999(xxx):1-9. Retrieved May 24, 2016 http://doi.wiley.com/10.1002/bit.26018.

McCreery, Richard L. 2000. *Raman Spectroscopy for Chemical Analysis.* John Wiley & Sons, Inc.

Mehdizadeh, Hamidreza et al. 2015. "Generic Raman-based calibration models enabling realtime monitoring of cell culture bioreac-

(56) References Cited

OTHER PUBLICATIONS tors." *Biotechnology progress* 31(4):1004-13. Retrieved Jul. 22, 2016 http://www.nobi.nlm.nih.gov/pubmed/25825868.

Milligan, Michael, Nicholas Lewin-Koh, Daniel Coleman, Adeyma Arroyo, and Victor Saucedo. 2014. "Semisynthetic model calibration for monitoring glucose in mammalian cell culture with in situ near infrared spectroscopy." *Biotechnology and bioengineering* 111(5):896-903. Retrieved Jul. 22, 2016 http://www.ncbi.nim.nih.gov/pubmed/24284833.

Mobili, P., A. Londero, and G. De Antoni. 2010. "Multivariate analysis of Raman spectra applied to microbiology: Discrimination of microorganisms at the species level." *Revista Mexicana De Fisica* 56(5):378-85.

Montgomery, D. 2013a. "Introduction to Designed Experiments." pp. 1-24 in *Design and Analysis of Experiments*. John Wiley & Sons, Inc.

Montgomery, D. 2013b. "Two-Level Factorial Designs." pp. 233-292 in *Design and Analysis of Experiments*. John Wiley & Sons, Inc.

Montgomery, Douglas C. 2013. "Response Surface Methodology." pp. 478-522 in *Design and Analysis of Experiments*. John Wiley & Sons, Inc.

Moretto, Justin, John Paul Smelko, Brandon Berry, Alex Doane, and Kelly Wiltberger. 2011. "Process Raman Spectroscopy for In-Line CHO Cell." (April):9-13.

Mortensen, Peter P., and Rasmus Bro. 2006. "Real-time monitoring and chemical profiling of a cultivation process." *Chemometrics and Intelligent Laboratory Systems* 84(1-2):106- 13. Retrieved Jul. 28, 2014 http://linkinghub.elsevier.com/retrieve/pii/S0169743906001158.

Moses, Sarah, Matthew Manahan, Alexandre Ambrogelly, and Wai Lam W. Ling. 2012. "Assessment of AMBR as a model for high-throughput cell culture process development strategy." *Advances in Bioscience and Biotechnology* 03(07):918-27. Retrieved Nov. 7, 2013 http://www.scirp.org/journal/PaperDownload.aspx?DOI=10.4236/abb.2012.37113.

Murphy, Kathleen R., Colin A. Stedmon, Daniel Graeber, and Rasmus Bro. 2013. "Fluorescence spectroscopy and multi-way techniques. PARAFAC." *Analytical Methods* 5(23):6557. Retrieved Oct. 3, 2016 http://xlink.rsc.org/?DOI=c3ay41160e.

Musmann, Carsten, Klaus Joeris, Sven Markert, Dorte Solle, and Thomas Scheper. 2016. "Spectroscopic methods and their applicability for high-throughput characterization of mammalian cell cultures in automated cell culture systems." *Engineering in Life Sciences* 16(5):405-16. Retrieved Aug. 8, 2016 http://doi.wiley.com/10.1002/elsc.201500122.

Nadler, Boaz, and Ronald R. Coifman. 2005. "Partial least squares, Beer's law and the net analyte signal: statistical modeling and analysis." *Journal of Chemometrics* 19(1):45-54. Retrieved Aug. 1, 2016 http://doi.wiley.com/10.1002/cem.906.

Nicolet Thermo Corporation. 2001. "Introduction to Fourier Transform Infrared Spectrometry."

Nienow, Alvin W. et al. 2013. "The physical characterisation of a microscale parallel bioreactor platform with an industrial CHO cell line expressing an IgG4." *Biochemical Engineering Journal* 76:25-36. Retrieved Nov. 7, 2013 http://linkinghub.elsevier.com/retrieve/pii/S1369703X13001150.

NIST. 2013. "NIST/Sematech e-Handbook of Statistical Methods." Measures of Scale. Retrieved Apr. 27, 2016 http://www.itl.nist.gov/div898/handbook/.

NIST/Sematech. 2012. "Choosing an Experimental Design." *e-Handbook of Statistical Methods*. Retrieved Aug. 14, 1BC http://www.itl.nist.go/div898/handbook/.

Nomikos, Paul, and John F. Macgregor. 1994. "Monitoring Batch Processes Using Multiway Principal Component Analysis." *American Institute of Chemical Engineers Journal* 40(8):1361-75.

De Noord, Onno E. 1994. "The influence of data preprocessing on the robustness and parsimony of multivariate calibration models." *Chemometrics and Intelligent Laboratory Systems* 23(1):65-70. Retrieved http://linkinghub.elsevier.com/retrieve/pii/0169743993E0065C.

Nova Biomedical Corporation. n.d. "BioProfile Automated Chemistry Analysers: For Cell Culture and Fermentation." Retrieved Dec. 13, 1BC http://www.lhybride.info/media/files/NOVA-BioProfile.pdf.

Ohadi, Kaveh, Hengameh Aghamohseni, Raymond L. Legge, and Hector M. Budman. 2014. "Fluorescence-based soft sensor for at situ monitoring of chinese hamster ovary cell cultures." *Biotechnology and Bioengineering* 111(8): 1577-86. Retrieved Jul. 28, 2014 http://doi.wiley.com/10.1002/bit.25222.

Olivieri, Alejandro C. et al. 2006. "Uncertainty estimation and figures of merit for multivariate calibration (IUPAC Technical Report)." *Pure and Applied Chemistry* 78(3):633-61. Retrieved Aug. 1, 2016 http://www.degruyter.com/view/j/pac.2006.78.issue-3/pac200678030633/pac200678030633.xml.

Pacis, Efren, Marcella Yu, Jennifer Autsen, Robert Bayer, and Feng Li. 2011. "Effects of cell culture conditions on antibody N-linked glycosylation-what affects high mannose 5 glycoform." *Biotechnology and Bioengineering* 108(10):2348-58. Retrieved Nov. 8, 2016 http://doi.wiley.com/10.1002/bit.23200.

Pandey, Shanta, and Charlotte Lyn Bright. 2008. "What Are Degrees of Freedom ?" *Social Work Research* 32(2).

PCT/US2018/054524 International Search Report and Written Opinion dated Jan. 25, 2019.

Pearson, K. 1901. "On lines and planes of closest fit to systems of points in space." *Philosophical Magazine* 6(2):559-72.

PerkinElmer. 2005. F T-I R S P E C T R O S C O P Y FT-IR *Spectroscopy Attenuated Total Reflectance ( ATR)*. USA. Retrieved http://www.utsc.utoronto.ca/~traceslab/ATR_FTIR.pdf.

Phillips, G. R., and J. M. Harris. 1990. "Polynomial Filters for Data Sets with Outlying or Missing Observations : Application to Charge-Coupled-Device-Detected Raman Spectra Contaminated by Cosmic Rays." *Analytical Chemistry* 62(21):2351-57.

Photometrics. 2010. *Keep the Noise Down ! Low Noise : An Integral Part of High-Performance CCS (HCCS) Camera Systems*.

Pray, Leslie. 2008. "Recombinant DNA Technology and Transgenic Animals." *Nature Education* 1(1):51. Retrieved http://www.nature.com/scitable/topicpage/recombinantdna-technology-and-transgenic-animals-34513.

Quick Generation of Raman Spectroscopy Based In-Process Glucose Control to Influence Biopharmaceutical Protein Product Quality During Mammalian Cell Culture; Berry et al.; Biogen. Published in Biotechnology Progress.

Raman-Based Nutrient Control in Bioprocessing Optimizes Viable Cell Density and Protein Glycation; Kaiser Optical Systems Inc. Application Note.

Raman-Based Bioreactor Control: Building Sustainable Applications; Bobiak et al., 1Bristol Myers Squibb. Presented at SCIX2017.

Rathore, A. S., R. Bhambure, and V. Ghare. 2010. "Process analytical technology (PAT) for biopharmaceutical products." *Analytical and bioanalytical chemistry* 398(1): 137-54. Retrieved Sep. 11, 2016 http://www.ncbi.nlm.nih.gov/pubmed/20480150.

Rathore, Anurag S. 2014. "QbD/PAT for bioprocessing: moving from theory to implementation." *Current Opinion in Chemical Engineering* 6:1-8. Retrieved Dec. 6, 2016 (http://linkinghub.elsevier.com/retrieve/pii/S2211339814000549).

Rathore, Anurag S., and Gautam Kapoor. 2016. "Implementation of Quality by Design for processing of food products and biotherapeutics." *Food and Bioproducts Processing* (99):231-43. Retrieved Dec. 6, 2016 (http://linkinghub.elsevier.com/retrieve/pii/S0960308516300414).

Rathore, Anurag S., Shachi Mittal, Mili Pathak, and Arushi Arora. 2014. "Guidance for performing multivariate data analysis of bioprocessing data." *Biotechnology Progress* 30(4):967-73.

Reitzer, Lawrence J., Burton M. Wice, and David Kennell. 1979. "Evidence That Glutamine, Not Sugar, Is the Major Energy Source of Cultured Hela Cells." *The Journal of Biological Chemistry* 254(8):2669-76.

Ren, Min, and Mark a Arnold. 2007. "Comparison of multivariate calibration models for glucose, urea, and lactate from near-infrared and Raman spectra." *Analytical and bioanalytical chemistry* 387(3):879-88. Retrieved Oct. 17, 2016 http://www.ncbi.nlm.nih.gov/pubmed/17200856.

Riley, M. R. et al. 2001. "Simultaneous measurement of 19 components in serum-containing animal cell culture media by fourier

(56) References Cited

OTHER PUBLICATIONS transform near-infrared spectroscopy." *Biotechnology progress* 17(2):376-78. http://www.ncbi.nim.nih.gov/pubmed/11312719.

Rinnan, Åsmund, and Charlotte M. Andersen. 2005. "Handling of first-order Rayleigh scatter in PARAFAC modelling of fluorescence excitation-emission data." *Chemometrics and Intelligent Laboratory Systems* 76(1):91-99. Retrieved Jun. 1, 2015 http:/linkinghub.elsevier.com/retrieve/pil/S0169743904002242.

Rinnan, Åsmund, Frans Van Den Berg, and Søren Balling Engelsen. 2009. "Review of the most common pre-processing techniques for near-infrared spectra." *TrAC Trends in Analytical Chemistry* 28(10):1201-22. Retrieved Oct. 15, 2014 http://linkinghub.elsevier.com/retrieve/pii/S0165993609001629.

Rinnan, Åsmund, Lars Nørgaard, and Frans Van Den Berg. 2009. "Data Pre-processing." in *Infrared Spectroscopy for Food Quality Analysis and Control*, vol. 3. Elsevier Inc.

Rita Costa, a, M. Elisa Rodrigues, Mariana Henriques, Joana Azeredo, and Rosário Oliveira. 2010. "Guidelines to cell engineering for monoclonal antibody production." *European journal of pharmaceutics and biopharmaceutics : official journal of Arbeitsgemeinschaft für Pharmazeutische Verfahrenstechnik e.V* 74(2):127-38. Retrieved Feb. 8, 2016 http://www.ncbi.nlm.nih.gov/pubmed/19853660.

Rodgers, Kyla R., and Richard C. Chou. 2016. "Therapeutic monoclonal antibodies and derivatives: Historical perspectives and future directions." *Biotechnology Advances* 34(6):1149-58. Retrieved Nov. 7, 2016 http://linkinghub.elsevier.com/retrieve/pii/S734975001630091X.

Roychoudhury, Payal, Linda M. Harvey, and Brian McNeil. 2006. "The potential of mid infrared spectroscopy (MIRS) for real time bioprocess monitoring." *Analytica chimica acta* 571(2):159-66. Retrieved Apr. 9, 2013 http://www.ncbi.nlm.nih.gov/pubmed/17723434.

Roychoudhury, Payal, Ronan O'Kennedy, Brian McNeil, and Linda M. Harvey. 2007. "Multiplexing fibre optic near infrared (NIR) spectroscopy as an emerging technology to monitor industrial bioprocesses." *Analytica chimica acta* 590(1):110-17. Retrieved Jul. 26, 2013 http://www.ncbi.nlm.nih.gov/pubmed/17416230.

Royle, Kate E., Ioscani Jimenez del Val, and Cleo Kontoravdi. 2013. "Integration of models and experimentation to optimise the production of potential biotherapeutics." *Drug discovery today* 18(23-24):1250-55. Retrieved Jun. 6, 2014 http://www.ncbi.nlm.nih.gov/pubmed/23850703.

Ryan, Paul W., Boyan Li, Michael Shanahan, Kirk J. Leister, and Alan G. Ryder. 2010. "Prediction of cell culture media performance using fluorescence spectroscopy." *Analytical chemistry* 82(4): 1311-17. Retrieved Jul. 25, 2013 http://www.ncbi.nlm.nih.gov/pubmed/20088547.

Ryder, Alan G. et al. 2010. "A stainless steel multi-well plate (SS-MWP) for high-throughput Raman analysis of dilute solutions." *Journal of Raman Spectroscopy* 41(10):1266-75. Retrieved Apr. 15, 2014 http://doi.wiley.com/10.1002/jrs.2586.

Sandor, M. et al. 2013. "Comparative study of non-invasive monitoring via infrared spectroscopy for mammalian cell cultivations." *Journal of biotechnology* 168(4):636-45. Retrieved Jan. 5, 2015 http://www.ncbi.nlm.nih.gov/pubmed/23948256.

Sathyanarayana, D. N. 2004. *Vibrational Spectroscopy. Theory and Applications*. New Age International P (Lts.) Publishers.

Schwab, Karen, Thomas Amann, Jakob Schmid, René Handrick, and Friedemann Hesse. 2016. "Exploring the Capabilities of Fluorometric Online Monitoring on CHO Cell Cultivations Producing a Monoclonal Antibody." *Biotechnology progress*. Retrieved http://onlinelibrary.wiley.com/doi/10.1002/btpr.2326/epdf.

Sellick, Christopher a et al. 2010. "Rapid monitoring of recombinant antibody production by mammalian cell cultures using fourier transform infrared spectroscopy and chemometrics." *Biotechnology and bioengineering* 106(3):432-42. Retrieved Mar. 3, 2013 http://www.ncbi.nlm.nih.gov/pubmed/20198655.

Shakirova, Laisana et al. 2013. "FT-IR spectroscopic investigation of bacterial cell envelopes from Zymomonas mobilis which have different surface hydrophobicities." *Vibrational Spectroscopy* 64:51-57. Retrieved Apr. 12, 2013 http:/linkinghub.elsevier.com/retrieve/pii/S9024203112001981.

Shao, Jun. 1993. "Linear Model Selection by Cross-Validation Linear Model Selection by Cross-Validation." *Journal of the American Statistical Association* 88(422):486-94.

Sheehan, David. 2000. *Physical Biochemistry: Principles and Applications*. John Wiley & Sons Ltd.

Shukla, Abhinav a, and Uwe Gottschalk. 2013. "Single-use disposable technologies for biopharmaceutical manufacturing." *Trends in biotechnology* 31(3):147-54. Retrieved Nov. 6, 2013 http://www.ncbi.nlm.nih.gov/pubmed/23178074.

Shukla, Abhinav a, and Jörg Thömmes. 2010. "Recent advances in large-scale production of monoclonal antibodies and related proteins." *Trends in biotechnology* 28(5):253-61. Retrieved Jul. 10, 2014 http://www.ncbi.nlm.nih.gov/pubmed/20304511.

Silva, Maurício a M., Marcus H. Ferreira, Jez W. B. Braga, and Marcelo M. Sena. 2012. "Development and analytical validation of a multivariate calibration method for determination of amoxicillin in suspension formulations by near infrared spectroscopy." *Talanta* 89:342-51. Retrieved Aug. 1, 2016 http://www.ncbi.nlm.nih.gov/pubmed/22284501.

Singh, Gajendra P., Shireen Goh, Michelangelo Canzoneri, and Rajeev J. Ram. 2015. "Raman spectroscopy of complex defined media: biopharmaceutical applications." *Journal of Raman Spectroscopy* 46(6):545-50. Retrieved Oct. 17, 2016 http://doi.wiley.com/10.1002/jrs.4686.

Skibsted, E., C. Lindemann, C. Roca, and L. Olsson. 2001. "On-line bioprocess monitoring with a multi-wavelength fluorescence sensor using multivariate calibration." *Journal of biotechnology* 88(1):47-57. Retrieved http://www.ncbi.nlm.nih.gov/pubmed/11377764.

Smelko, John Paul, Thomas Ryll, and Dethardt Muller. 2015. "Concepts and Technologies for Advanced Process Monitoring and Control." pp. 523-570 in *Animal Cell Biotechnology*, edited by Hansjorg Hauser and Roland Wagner. Walter de Gruyter GmbH, Berlin.

Smilde, A., R. Bro, and p. Geladi. 2004. "Split-Half Analysis." pp. 164-166 in *Multi-Way Analysis: Applications in the Chemical Sciences*. John Wiley & Sons Ltd.

Smith, Brian C. 1996. "How an FTIR Works." pp. 15-27 in *Fundamentals of Fourier Transform Infrared Spectroscopy*. CRC Press LLC.

Smith, E., and G. Dent. 2004a. *Modern Raman Spectroscopy*. Chichester, UK: John Wiley & Sons, Ltd. Retrieved http://doi.wiley.com/10.1002/0470011831.

Smith, E., and G. Dent. 2004b. "The theory of Raman Spectroscopy." pp. 71-92 in *Modern Raman Spectroscopy—A Practical Approach*. Chichester, UK: John Wiley & Sons, Ltd.

Smith, Ewen, and G. Dent. 2004a. "The Raman Experiment—Raman Instrumentation, Sample Presetations, Data Handling and Practical Aspects of Interpretation." pp. 23-61 in *Modern Raman Spectroscopy—A Practical Approach*. Chichester, UK: John Wiley & Sons, Ltd. Retrieved http://doi.wiley.com/10.1002/0470011831.

Smith, Ewen, and Geoffrey Dent. 2004b. "2.4 NIR Excitation." pp. 30-31 in *Modern Raman Spectroscopy—A Practical Approach*. Chichester, UK: John Wiley & Sons, Ltd. Retrieved http://doi.wiley.com/10.1002/0470011831.

Smith, Lindsay I. 2002. "A tutorial on Principal Components Analysis Introduction."

Smith, Wendell F. 2005. "Some Design Considerations." pp. 45-46 in *Experimental Design for Formulation*. American Statistical Association and the Society for Industrial and Applied Mathematics.

Sperry, W. H. Nelson and J. F. 1991. *The Rapid Detection of Single Bacterial Cells by Deep UV Micro Raman Spectroscopy*. Retrieved http://www.dtic.mil/dtic/tr/fulltext/02/a249811.pdf.

Stat-Ease Inc. 2008. "FDS—A Power Tool for Designers of Optimization Experiments." (September):1-4.

Stat-Ease Inc. 2016. "Multifactor RSM Tutorial." pp. 1-56 in *Design-Expert 10 User's Guide*.

Stryjewska, Agnieszka, Katarzyna Kiepura, Tadeusz Librowski, and Stanislaw Lochyński. 2013. "Biotechnology and genetic engineering in the new drug development." *Pharmacological Reports* 65:1075-85.

(56) References Cited

OTHER PUBLICATIONS

Student. 1908. "The Probable Error of a Mean.pdf." *Biometrika* 6(1):1-25.

Subramanian, Anand, and Luis Rodriguez-saona. 2009. "Fourier-Transform Infrared Spectroscopy." pp. 145-174 in *Infrared Spectroscopy for Food Quality Analysis and Control*. Elsevier Inc.

Swiech, Kamilla, Virginia Picanco-Castro, and Dimas Tadeu Covas. 2012. "Human cells: new platform for recombinant therapeutic protein production." *Protein expression and purification* 84(1):147-53. Retrieved Jul. 29, 2014 http://www.ncbi.nlm.nih.gov/pubmed/22580292.

Swierenga, H., A. P. de Weijer, R. J. van Wijk, and L. M. C. Buydens. 1999. "Strategy for constructing robust multivariate calibration models." *Chemometrics and Intelligent Laboratory Systems* 49:1-17. Retrieved http://linkinghub.elsevier.com/retrieve/pii/S0169743999000283.

Tayi, Venkata, and Michael Butler. 2015a. "5.1. Physiology and Metabolism of Animal Cells for Production." pp. 301-318 in *Animal Cell Biotechnology: in biologics production*, edited by Hansjorg Hauser and Roland Wagner. Walter de Gruyter GmbH, Berlin.

Tayi, Venkata, and Michael Butler. 2015b. "Basic Aspect of Animal Cell Cultivation." pp. 301-325 in *Animal Cell Biotechnology*, edited by Hansjorg Hauser and Roland Wagner. Walter de Gruyter GmbH, Berlin.

Teixeira, a P., R. Oliveira, P. M. Alves, and M. J. T. Carrondo. 2009. "Advances in on-line monitoring and control of mammalian cell cultures: Supporting the PAT initiative." *Biotechnology advances* 27(6):726-32. Retrieved Jul. 25, 2016 http://www.ncbi.nlm.nih.gov/pubmed/19450676.

Teixeira, Ana P. et al. 2009. "In situ 2D fluorometry and chemometric monitoring of mammalian cell cultures." *Biotechnology and bioengineering* 102(4):1098-1106. Retrieved Jul. 22, 2016 http://www.nobi.nlm.nih.gov/pubmed/18853411.

The Pennsylvania State University. 2016. "STAT 501 Regression Methods." 2.6 The Analysis of Variance (ANOVA) table and the. Retrieved https://onlinecourses.science.psu.edu/stat501/node/266.

Thygesen, Lisbeth Garbrecht, Åsmund Rinnan, Søren Barsberg, and Jens K. S. Møller. 2004. "Stabilizing the PARAFAC decomposition of fluorescence spectra by insertion of zeros outside the data area." *Chemometrics and Intelligent Laboratory Systems* 71(2):97-106. Retrieved Apr. 26, 2016 http://linkinghub.elsevier.com/retrieve/pii/S0169743904000048.

Thomas E. Matthews et al; "Closed loop control of lactate concentration in mammalian cell culture by Raman spectroscopy leads to improved cell density, viability, and biopharmaceutical protein production", Biotechnology and Bioengineering, vol. 113, No. 11, Jun. 9, 2016, pp. 2416-2424.

Ulber, Roland, Jan-Gerd Frerichs, and Sascha Beutel. 2003. "Optical sensor systems for bioprocess monitoring." *Analytical and bioanalytical chemistry* 376(3):342-48. Retrieved Jul. 25, 2016 http://www.ncbi.nlm.nih.gov/pubmed/12728296.

Ündey, Cenk, Sinem Ertunç, Thomas Mistretta, and Manuj Pathak. 2010. "Applied Advanced Process Analytics in Biopharmaceutical Manufacturing : Challenges and Prospects in Real-time Monitoring and Control." Journal of Process Control 20(9):1009-18. Retrieved http://dx.doi.org/10.1016/j.jprocont.2010.05.008.

Velioglu, Serap Durakli et al. 2016. "Raman Spectroscopic Barcode Use for Differentiation of Vegetable Oils and Determination of Their Major Fatty Acid Composition." *Journal of the American Oil Chemists' Society* 93(5):627-35. Retrieved Aug. 1, 2016 http://link.springer.com/10.1007/s11746-016-2808-7.

Venkateswarlu, P., H. D. Bist, and Y. S. Jain. 1975. "Laser excited Raman spectrum of ammonium sulfate single crystal." *Journal of Raman Spectroscopy* 3(2-3):143-51. Retrieved Oct. 17, 2016 (http://doi.wiley.com/10.1002/jrs.1250030205).

Verboven, Sabine, Mia Hubert, and Peter Goos. 2012. "Robust preprocessing and model selection for spectral data." *Journal of Chemometrics* 26(6):282-89. Retrieved Jun. 15, 2013 http://doi.wiley.com/10.1002/cem.2446.

Victoria Brewster, Roger Jarvis, Royston Goodacre. 2009. "Raman Spectroscopic Techniques for Biotechnology and Bioprocessing." *European Pharmaceutical Review* (1):48-52.

Victoria L. Brewster, Lorna Ashton, and Royston Goodacre. 2011. "Monitoring the Glycosylation Status of Proteins Using Raman Spectroscopy." *Analytical Chemistry* 83:6074-81.

Wang, Yu-Chieh, Suzanne E. Peterson, and Jeanne F. Loring. 2014. "Protein posttranslational modifications and regulation of pluripotency in human stem cells." *Cell research* 24(2):143-60. Retrieved Oct. 13, 2016 http://www.pubmedcentral.nih.gov/articlerender.fcgi?artid=3915910&tool=pmcentrez&rendertype=abstract.

Wei E. Huang, Robert I. Griffiths, Ian P. Thompson, Mark J. Bailey and Andrew S. Whiteley. 2004. "Raman Microscopic Analysis of Single microbial Cells." *Analytical Chemistry* 76(15):4452-58.

Whelan, Jessica, Stephen Craven, and Brian Glennon. 2012. "In situ Raman spectroscopy for simultaneous monitoring of multiple process parameters in mammalian cell culture 245 bioreactors." *Biotechnology progress* 28(5):1355-62. Retrieved Mar. 27, 2013 http://www.nobl.nim.nih.gov/pubmed/22740438.

Whitcomb, Patrick J., and Kinley Lamtz. 1992. "The role of pure error on normal probability plots." *ASQC Technical Conference Transactions* 1223-29.

Winder, Catherine L. et al. 2011. "Metabolic fingerprinting as a tool to monitor whole-cell biotransformations." *Analytical and bioanalytical chemistry* 399(1):387-401. Retrieved Apr. 11, 2013 http://www.ncbi.nlm.nih.gov/pubmed/21038074.

Wold, Svante. 1992. "Nonlinear partial least squares modelling II. Spline inner relation." Chemometrics and Intelligent Laboratory Systems 14(1-3):71-84. Retrieved http://linkinghub.elsevier.com/retrieve/pii/016974399280093J.

Wold, Svante. 1995. "Chemometrics; what do we mean with it, and what do we want from it?" *Chemometrics and Intelligent Laboratory Systems* 30(1):109-15. Retrieved http://linkinghub.elsevier.com/retrieve/pii/0169743995000429.

Wold, Svante, Kim Esbensen, and Paul Geladi. 1987. "Principal component analysis." *Chemometrics and Intelligent Laboratory Systems* 2(1-3):37-52. Retrieved http://linkinghub.elsevier.com/retrieve/pii/0169743987800849.

Wold, Svante, and Johan Trygg. 2004. "The PLS method—partial least squares projections to latent structures—and its applications in industrial RDP ( research , development , and production )." 1(June): 1-44.

Wolf, G. et al. 2001. "Two-dimensional fluorometry coupled with artificial neural networks: a novel method for on-line monitoring of complex biological processes." *Biotechnology and bioengineering* 72(3):297-306. Retrieved http://www.ncbi.nlm.nih.gov/pubmed/11135199.

Xiaobo, Zou, Zhao Jiewen, Malcolm J. W. Povey, Mel Holmes, and Mao Hanpin. 2010. "Variables selection methods in near-infrared spectroscopy." *Analytica chimica acta* 667(1-2): 14-32. Retrieved May 23, 2014 http://www.nobi.nlm.nih.gov/pubmed/20441862.

Xu, Lu et al. 2008. "Ensemble preprocessing of near-infrared (NIR) spectra for multivariate calibration." *Analytica chimica acta* 616(2):138-43. Retrieved Jul. 16, 2013 http://www.nobi.nlm.nih.gov/pubmed/18482596.

Yoon, Sung Kwan, Sang Lim Choi, Ji Yong Song, and Gyun Min Lee. 2005. "Effect of culture pH on erythropoietin production by Chinese hamster ovary cells grown in suspension at 32.5 and 37.0° C." *Biotechnology and Bioengineering* 89(3):345-56. Retrieved Nov. 8, 2016 http://doi.wiley.com/10.1002/bit.20353.

Yoon, Sung Kwan, Sun Ok Hwang, and Gyun Min Lee. 2004. "Enhancing Effect of Low Culture Temperature on Specific Antibody Productivity of Recombinant Chinese Hamster Ovary Cells : Clonal Variation." *Biotechnology Progress* 20:1683-88.

Zanghi, James A., Albert E. Schmelzer, Thomas P. Mendoza, Richard H. Knop, and William M. Miller. 1999. "Bicarbonate Concentration and Osmolality Are Key Determinants in the Inhibition of CHO Cell Polysialylation Under Elevated $pCO_2$ or pH." *Biotechnology and Bioengineering* 65(2):182-91.

Zhu, Marie M. et al. 2005. "Effects of Elevated $pCO_2$ and Osmolality on Growth of CHO Cells and Production of Antibody-Fusion Protein B1 : A Case Study." 6-9.

(56) References Cited

OTHER PUBLICATIONS

Zhu et al. "Industrial Production of Therapeutic Proteins: Cell Lines, Cell Culture, and Purification," Springer International Publishing AG 2017, Handbook of Industrial Chemistry and Biotechnology, pp. 1639-1669.

\* cited by examiner

Figure 2: A) Spectra used for calibration set and B) after trimming wavelengths and applying preprocessing.

Figure 3: Calibration model predicted versus offline reference measurement plot for A) glucose, B) glutamate, C) lactate, D) ammonium, E) VCC, F) TCC, and G) product concentration.

Figure 4: Raman Predictions versus offline reference method A) glucose B) glutamate C) lactate D) ammonium E) VCC F) TCC G) product concentration. Raman prediction (Dark line), + RMSEP (Lighter lines), offline reference (Squares). i=5 L Run 1, ii=5 L Run 2, iii = 10 L Run

AUTOMATED CONTROL OF CELL CULTURE USING RAMAN SPECTROSCOPY

CROSS-REFERENCE TO RELATED APPLICATIONS

This application is a continuation of U.S. patent application Ser. No. 16/152,950, having a filing date of Oct. 6, 2018, which claims filing benefit of U.S. Provisional Patent Application Ser. No. 63/066,909, having a filing date of Aug. 18, 2020 and PCT Patent Application Serial No. PCT/US2021/046228, having a filing date of Aug. 17, 2021, which are incorporated herein by reference for all purposes.

RELATED APPLICATIONS

The present application is based on and claims priority to U.S. Provisional Patent Application Ser. No. 62/569,076 having a filing date of Oct. 6, 2017, and U.S. Provisional Patent Application Ser. No. 62/569,190 having a filing date of Oct. 6, 2017, both of which are incorporated herein by reference in its entirety.

BACKGROUND

Bioreactors, which are apparatuses in which biological reactions or processes can be carried out on a laboratory or industrial scale, are used widely within the biopharmaceutical industry. Bioreactors can be used to produce all different types of bioproducts. Bioproducts can include, for instance, cell cultures and materials derived from cell cultures including beverages, biofuels, bioenergy, biochemicals, antibiotics, amino acids, enzymes, monoclonal antibodies, monomers, proteins, food cultures, biopolymers, alcohols, flavorings, fragrances, and the like. In some embodiments, cell cultures can be grown for cell therapy. Cell therapy is the prevention, treatment, cure or mitigation of disease or injuries in humans by the administration of autologous, allogeneic or xenogeneic cells that have been manipulated or altered ex vivo. One goal of cell therapy is to repair, replace or restore damaged tissues or organs.

Cell cultures are typically grown in batch processes where the biological material remains in the bioreactor until the end of the reaction time. In certain of these processes, fluid medium contained within the bioreactor can be periodically or continuously removed and resupplied in order to replenish nutrients contained within the fluid medium and for possibly removing damaging by-products that are produced during the process.

During the growth of cell cultures, the regulation of key nutrients in the medium can have a direct impact on the quality of the product that is produced. For example, various carbohydrates, such as glucose, are fed to bioreactors in order to promote cell growth. Less than optimum glucose levels, however, can stunt or inhibit growth. For instance, lower glucose levels can starve cell cultures and lead to the build-up of waste. Simply increasing glucose levels to prevent depletion can also lead to a dramatic fluctuations in glucose levels which also adversely affect cell growth. Attempting to maintain optimum nutrient and waste levels in cell cultures can be unpredictable and subject to unforeseeable changes when the cell culture is not constantly monitored.

Historically, upstream bioprocesses have been monitored by removing samples that are then analyzed for selected metabolites, cell growth, and product concentration using offline methods, with continuous real time measurements being limited in scope (e.g., pH, dissolved oxygen tension (DOT), temperature). The offline methods require trained operators, are often labor intensive, and generate waste through the use of expensive reagents and samples. Additionally, offline measurement typically occurs at infrequent intervals (e.g., every 12 or 24 hrs) which can potentially miss shifts in cell metabolism that may be indicative of abnormal processes. Furthermore, every sample removed from the bioreactor carries the added potential risk for contamination.

Recent process improvement efforts within the industry have focused on identifying process analytical technologies that can be used to continuously monitor and control bioprocesses in real time. While these options enable more frequent monitoring of the bioreactor process, they require continuous sample removal from the bioreactor and still require the use of expensive reagents for analysis. Additionally, concerns over the scalability of these systems and the increased potential risk of contamination from sample removal make these options less desirable for continuous process monitoring. In view of the above, a need exists for a process and system for monitoring biochemical and biopharmaceutical processes such as processes for propagating cell cultures that is noninvasive and allows for continuous or periodic adjustments in order to maintain optimum conditions within a bioreactor.

SUMMARY

The present disclosure is generally directed to a processing system for propagating biomaterials, such as cell cultures. In one embodiment, for instance, the processing system of the present disclosure is directed to propagating mammalian cell cultures. In an alternative embodiment, the system and process of the present disclosure can be used for propagating cells for cell therapy. Cell cultures processed in accordance with the present disclosure, for instance, can include stem cells, T cells, and immune cells, including B cells, natural killer cells, dendritic cells, tumor infiltrating lymphocytes, monocytes, megakaryocytes, and the like. In accordance with the present disclosure, Raman spectroscopy is used in order to monitor one or more parameters of a bioprocess within a bioreactor. The use of Raman spectroscopy in accordance with the present disclosure allows for the periodic or continuous monitoring of one or more parameters in a bioprocess without the disadvantages associated with offline sampling. For example, Raman spectroscopy can reduce the volume and analysis time required for parameter concentration analysis. In accordance with the present disclosure, Raman spectroscopy is coupled with a control system which allows for the automation of process speeds which results in improved process robustness and control. In one embodiment, for instance, the control system can include a predictive model that extrapolates parameter concentrations in the future for maintaining the bioprocess environment within carefully controlled limits.

In one embodiment, for instance, the present disclosure is directed to a process for propagating a cell culture. The process includes exposing a cell culture and a bioreactor to a coherent light source causing light to scatter. The coherent light source, for instance, may comprise a light beam emitted by a laser. The light contacting the cell culture, in one embodiment, can have a wavelength of from about 400 nm to about 1500 nm, such as from about 700 nm to about 850 nm.

An intensity of the scattered light is measured using Raman spectroscopy. A concentration of at least one parameter in the cell culture is determined based upon the measured intensity of light. In one embodiment, for instance, the concentration is determined by a controller. Based on the determined concentration of the parameter, the controller can then selectively increase or decrease flow of a parameter influencing substance to the bioreactor in order to maintain the parameter within preset limits.

The parameter measured according to the process can comprise, for instance, glucose concentration, lactate concentration, glutamate concentration, ammonium concentration, viable cell concentration, total cell concentration, product concentration, or mixtures thereof. In one embodiment, for instance, at least two, such as at least three, such as least four different parameters are measured from the intensity of the scattered light using Raman spectroscopy. The controller can be configured to receive all of the concentration data and control one or more parameter influencing substances. The parameter influencing substance, for instance, may comprise one or more nutrient medias. For instance, the controller may increase flow of a carbohydrate, such as glucose into the bioreactor. Alternatively, the controller can increase the withdrawal of a fluid medium from the bioreactor in a process that uses perfusion.

The concentration of the at least one parameter can be determined using various methods. In one embodiment, for instance, the concentration of the parameter is determined by comparing the light intensity data to reference data contained within the controller. In one embodiment, the controller can include a predictive model that extrapolates a future concentration of the parameter based on the determined concentration of the parameter and can selectively increase or decrease at least one parameter influencing substance in order to maintain the parameter within preset limits based on the calculated future concentration.

In determining the concentration of the parameter, statistical analysis can be conducted on the scattered light intensity measured using Raman spectroscopy. In one embodiment, for instance, a standard normal variate can be applied to the measured scattered light intensity. After the standard normal variate is applied, a first derivative can be applied followed by detrending. The conducted statistical analysis can be modeled using a least squares regression method. After preprocessing the measured scattered light intensity, a spectral range can be selected that correlates to the parameter being monitored. The statistical analysis or the preprocessing of the measured scattered light intensity can be conducted by the controller.

In one embodiment, the cell culture is propagated in a batch process for from about 2 days to about 28 days and then harvested. The concentration of the at least one parameter can be determined within the first 12 hours to 4 days of the process. The initial concentration data can then be used by the controller to selectively increase or decrease the flow rate of a parameter influencing substance after the initial measurements.

During the process, the concentration of the at least one parameter can be determined periodically or continuously. In one embodiment, for instance, concentration determinations can be made at least every 24 hours, such as at least every 16 hours, such as at least every 8 hours, such as at least every 4 hours, such as at least every 2 hours, such as at least every hour.

The present disclosure is also directed to a system for propagating a cell culture. The system includes a bioreactor defining a hollow interior for receiving a cell culture. The bioreactor includes a plurality of ports for feeding and/or removing materials from the hollow interior. A nutrient media feed for feeding a nutrient media to the hollow interior of the bioreactor is included in the system and is in fluid communication with at least one of the ports on the bioreactor. The system further includes a light conveying device in communication with the hollow interior of the bioreactor. The light conveying device is for conveying light to the bioreactor and for conveying light away from the bioreactor.

The system further includes a coherent light source in communication with the light conveying device. The coherent light source exposes a cell culture in the bioreactor to a beam of light. The coherent light source, for instance, may comprise a laser that is configured to emit light at a wavelength of from about 400 nm to about 1500 nm.

The light conveying device is in communication with a Raman spectrometer. The Raman spectrometer is for receiving scattered light from the bioreactor after a cell culture has been exposed to a beam of light from the coherent light source. The Raman spectrometer is for measuring an intensity of the scattered light for determining the concentration of one or more parameters contained within the bioreactor.

In accordance with the present disclosure, the system further includes a controller. The controller can be in communication with the Raman spectrometer for receiving information regarding the intensity of the scattered light. The controller can be configured to determine the concentration of one or more parameters from the Raman spectrometer. The controller can be further configured to control the nutrient media feed based upon the determined parameter concentrations. The controller, for instance, can selectively increase or decrease flow of a nutrient media from the nutrient media feed to the bioreactor in order to maintain the concentration of one or more parameters within preset limits.

The controller can comprise one or more microprocessors. As used herein, a microprocessor can include any programmable logic unit.

In one embodiment, the controller can be programed with a predictive model that can extrapolate and predict the concentration of one or more parameters in the future while the cell culture is propagating. The controller can be configured to selectively increase or decrease nutrient feed to the bioreactor based on the determined concentration of the one or more parameters and based upon the future predicted concentration of the one or more parameters.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
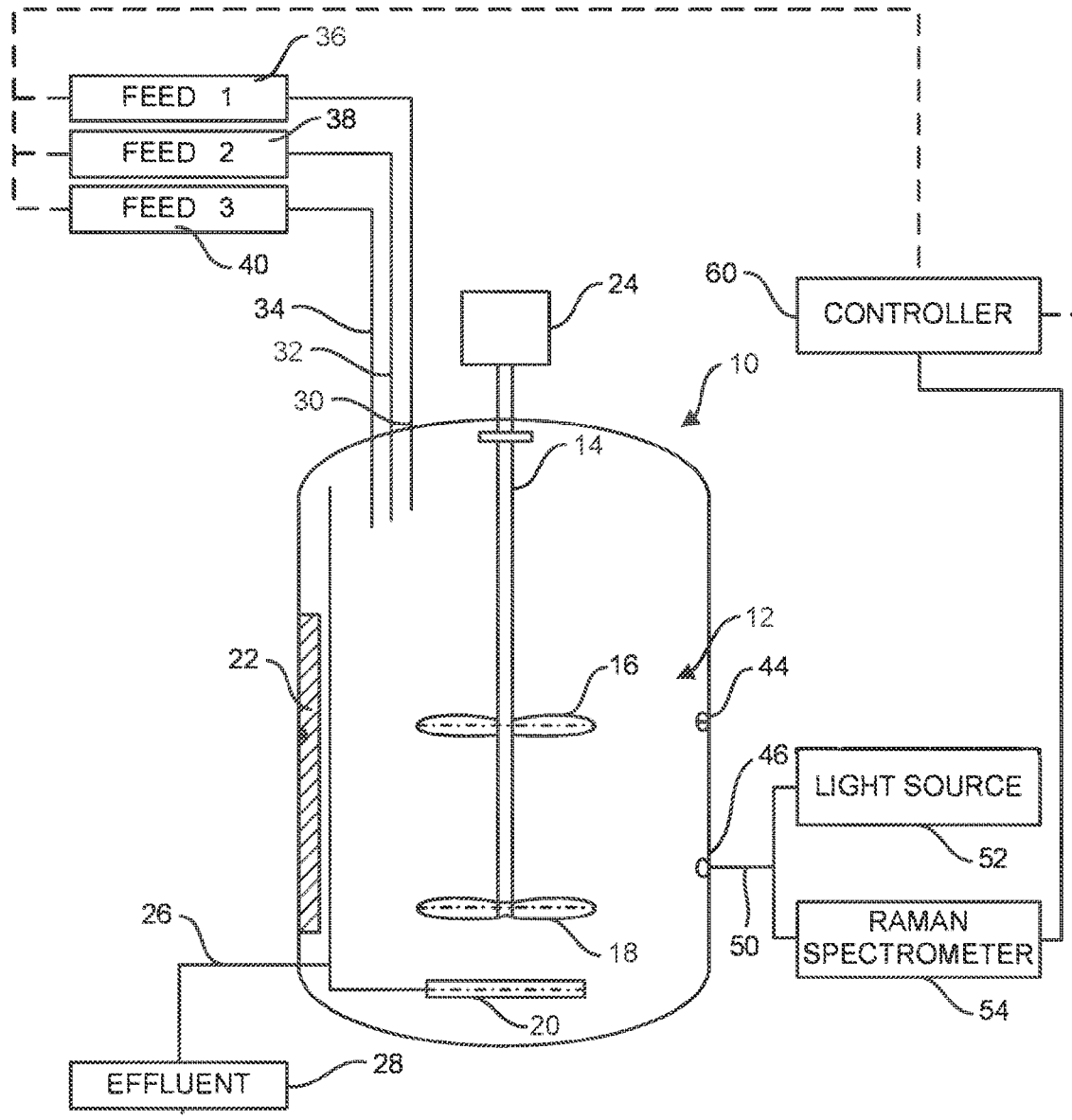
FIG. 1 is a cross sectional view of one embodiment of a bioreactor system in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a process and system for producing a bioproduct. In one embodiment, for instance, the present disclosure is directed to a process and system for propagating a cell culture within a bioreactor. The system of the present disclosure can use open loop or closed loop control for monitoring one or more parameters in the bioreactor and then automatically changing or varying the flow of a parameter influencing substance into or out of the bioreactor. The autonomous control is coupled with Raman spectroscopy which allows for continuous or periodic noninvasive monitoring of one or more parameters within the bioreactor. Raman spectroscopy can, for instance, continuously monitor and collect information within a wavelength region, such as from about 800 nm to about 2500 nm, and collect information about the overtones of fundamental absorption bands observed, which can be used to determine parameter concentrations.

Raman spectroscopy measures changes in the vibrational frequency of component specific molecular bonds. Raman provides complimentary information to more traditional mid-IR spectroscopy, while having more utility in aqueous solutions due to its resistance to water interference, making it desirable for bioreactor applications.

Raman spectra collected from inline Raman probes, coupled with multivariate analysis (MVA), can monitor metabolites and cell concentration. Raman spectroscopy provides the ability to monitor bioprocesses in real time which allows for the implementation of feedback controls for nutrient feeds leading to improved product quality and cell productivity.

In accordance with the present disclosure, in line spectroscopy can be coupled with predictive model control. Of particular advantage, the process and system of the present disclosure can be scaled to various different bioreactor sizes and to various cell lines. For instance, the predictive models used in accordance with the present disclosure are robust and developed for platform processes that are not cell line dependent and thus can be used in clinical as well as commercial manufacturing. In particular, it was discovered that certain parameters contained in the bioreactor during the production of bioproducts are generic and thus not dependent upon specific cell line applications.

Referring to FIG. 1, one embodiment of a bioreactor system in accordance with the present disclosure is shown. The bioreactor system includes a bioreactor 10. In general, the system and process of the present disclosure can use any suitable bioreactor. The bioreactor, for instance, may comprise a fermenter, a stirred-tank reactor, an adherent bioreactor, a wave-type bioreactor, a disposable bioreactor, and the like. In the embodiment illustrated in FIG. 1, the bioreactor 10 comprises a hollow vessel or container that includes a bioreactor volume 12 for receiving a cell culture within a fluid growth medium. As shown in FIG. 1, the bioreactor system can further include a rotatable shaft 14 coupled to an agitator such as dual impellers 16 and 18.

The bioreactor 10 can be made from various different materials. In one embodiment, for instance, the bioreactor 10 can be made from metal, such as stainless steel. Metal bioreactors are typically designed to be reused.

Alternatively, the bioreactor 10 may comprise a single use bioreactor made from a rigid polymer or a flexible polymer film. When made from a rigid polymer, for instance, the bioreactor walls can be free standing. Alternatively, the bioreactor can be made from a flexible polymer film or shape conforming material that can be liquid impermeable and can have an interior hydrophilic surface. In one embodiment, the bioreactor 10 can be made from a flexible polymer film that is designed to be inserted into a rigid structure, such as a metal container for assuming a desired shape. Polymers that may be used to make the rigid vessel or flexible polymer film include polyolefin polymers, such as polypropylene and polyethylene. Alternatively, the polymer can be a polyamide. In still another embodiment, a flexible polymer film can be formed from multiple layers of different polymer materials. In one embodiment, the flexible polymer film can be gamma irradiated.

The bioreactor 10 can have any suitable volume. For instance, the volume of the bioreactor 10 can be from 0.1 mL to about 25,000 L or larger. For example, the volume 12 of the bioreactor 10 can be greater than about 0.5 L, such as greater than about 1 L, such as greater than about 2 L, such as greater than about 3 L, such as greater than about 4 L, such as greater than about 5 L, such as greater than about 6 L, such as greater than about 7 L, such as greater than about 8 L, such as greater than about 10 L, such as greater than about 12 L, such as greater than about 15 L, such as greater than about 20 L, such as greater than about 25 L, such as greater than about 30 L, such as greater than about 35 L, such as greater than about 40 L, such as greater than about 45 L. The volume of the bioreactor 10 is generally less than about 25,000 L, such as less than about 15,000 L, such as less than about 10,000 L, such as less than about 5,000 L, such as less than about 1,000 L, such as less than about 800 L, such as less than about 600 L, such as less than about 400 L, such as less than about 200 L, such as less than about 100 L, such as less than about 50 L, such as less than about 40 L, such as less than about 30 L, such as less than about 20 L, such as less than about 10 L. In one embodiment, for instance, the volume of the bioreactor can be from about 1 L to about 5 L. In an alternative embodiment, the volume of the bioreactor can be from about 25 L to about 75 L. In still another embodiment, the volume of the bioreactor can be from about 1,000 L to about 5,000 L.

In addition to the impellers 16 and 18, the bioreactor 10 can include various additional equipment, such as baffles, spargers, gas supplies, heat exchangers or thermal circulator ports, and the like which allow for the cultivation and propagation of biological cells. For example, in the embodiment illustrated in FIG. 1, the bioreactor 10 includes a sparger 20 and a baffle 22. In addition, the bioreactor system can include various probes for measuring and monitoring pressure, foam, pH, dissolved oxygen, dissolved carbon dioxide, and the like.

As shown in FIG. 1, the bioreactor 10 can include a rotatable shaft 14 attached to impellers 16 and 18. The rotatable shaft 14 can be coupled to a motor 24 for rotating the shaft 14 and the impellers 16 and 18. The impellers 16 and 18 can be made from any suitable material, such as a metal or a biocompatible polymer. Examples of impellers suitable for use in the bioreactor system include hydrofoil impellers, high-solidity pitch-blade impellers, high-solidity hydrofoil impellers, Rushton impellers, pitched-blade impellers, gentle marine-blade impellers, and the like. When containing two or more impellers, the impellers can be spaced apart along the rotating shaft 14.

As shown in FIG. 1, the bioreactor 10 also includes a plurality of ports. The ports can allow supply lines and feed lines into and out of the bioreactor 10 for adding and removing fluids and other materials. In addition, the one or more ports may be for connecting to one or more probes for monitoring conditions within the bioreactor 10. In addition, the bioreactor 10 and be placed in association with a load cell for measuring the mass of the culture within the bioreactor.

In the embodiment illustrated in FIG. 1, the bioreactor 10 includes a bottom port 26 connected to an effluent 28 for withdrawing materials from the bioreactor continuously or periodically. Materials can be withdrawn from the bioreactor 10 using any suitable method. For instance, in an alternative embodiment, an effluent can be removed from the bioreactor 10 from the top of the bioreactor using a dip tube. In addition, the bioreactor 10 includes a plurality of top ports, such as ports 30, 32, and 34. Port 30 is in fluid communication with a first fluid feed 36, port 32 is in fluid communication with a second feed 38 and port 34 is in fluid communication with a third feed 40. The feeds 36, 38 and 40 are for feeding various different materials to the bioreactor 10, such as a nutrient media. As used herein, a nutrient media refers to any fluid, compound, molecule, or substance that can increase the mass of a bioproduct, such as anything that may be used by an organism to live, grow or otherwise add biomass. For example, a nutrient feed can include a gas, such as oxygen or carbon dioxide that is used for respiration or any type of metabolism. Other nutrient media can include carbohydrate sources. Carbohydrate sources include complex sugars and simple sugars, such as glucose, maltose, fructose, galactose, and mixtures thereof. A nutrient media can also include an amino acid. The amino acid may comprise, glycine, alanine, valine, leucine, isoleucine, methionine, proline, phenylalanine, tryptophan, serine, threonine, asparagine, glutamine, tyrosine, cysteine, lysine, arginine, histidine, aspartic acid and glutamic acid, single stereoisomers thereof, and racemic mixtures thereof. The term "amino acid" can also refer to the known non-standard amino adds, e.g., 4-hydroxyproline, ε-N,N,N-trimethyllysine, 3-methylhistidine, 5-hydroxylysine, O-phosphoserine, γ-carboxyglutamate, γ-N-acetyllysine, ω-N-methylarginine, N-acetylserine, N,N,N-trimethylalanine, N-formylmethionine, γ-arninobutyric acid, histamine, dopamine, thyroxine, citrulline, ornithine, β-cyanoalanine, homocysteine, azaserine, and S-adenosylmethionine. In some embodiments, the amino acid is glutamate, glutamine, lysine, tyrosine or valine.

The nutrient media can also contain one or more vitamins. Vitamins that may be contained in the nutrient media include group B vitamins, such as B12. Other vitamins include vitamin A, vitamin E, riboflavin, thiamine, biotin, and mixtures thereof. The nutrient media can also contain one or more fatty acids and one or more lipids. For example, a nutrient media feed may include cholesterol, steroids, and mixtures thereof. A nutrient media may also supply proteins and peptides to the bioreactor. Proteins and peptides include, for instance, albumin, transferrin, fibronectin, fetuin, and mixtures thereof. A growth medium within the present disclosure may also include growth factors and growth inhibitors, trace elements, inorganic salts, hydrolysates, and mixtures thereof. In one embodiment, the growth medium can contain a serum, such as human serum or calf serum.

As shown in FIG. 1, the bioreactor can be in communication with multiple nutrient feeds. In this manner, a nutrient media can be fed to the bioreactor containing only a single nutrient for better controlling the concentration of the nutrient in the bioreactor during the process. In addition or alternatively, the different feed lines can be used to feed gases and liquids separately to the bioreactor.

In addition to ports on the top and bottom of the bioreactor 10, the bioreactor can include ports located along the sidewall. For instance, the bioreactor 10 shown in FIG. 1 includes ports 44 and 46. The ports located along the sidewall are optional. For instance, in an alternative embodiment, monitoring of the cell culture can occur from the top of the bioreactor 10 using headplate ports.

In accordance with the present disclosure, port 46 is in communication with a parameter monitoring and control system that can maintain optimum concentrations of one or more parameters in the bioreactor 10 for propagating cell cultures or otherwise producing a bioproduct. In the embodiment illustrated in FIG. 1, the system is designed to take in line measurements. In particular, measurements are made of the cell culture while the cell culture resides within the bioreactor 10, i.e. online. Alternatively, however, measurements can be taken at line or off line. For example, in one embodiment, the bioreactor 10 can be in communication with a sampling station. Samples of the cell culture can be fed to the sampling station for taking light scattering measurements. In still another embodiment, samples of the cell culture can be removed from the bioreactor and measured off line.

In the embodiment illustrated in FIG. 1, port 46 is in communication with a light conveying device 50. The light conveying device 50 is in communication with a light source 52, such as a coherent light source. In addition, the light conveying device 50 is in communication with a Raman spectrometer 54. The light source 52 is for exposing a cell culture within the bioreactor 10 to a beam of light. The light conveying device 50 is then configured to convey scattered light reflected off of the cell culture to the Raman spectrometer 54 for determining the concentration of one or more parameters within the bioreactor 10. The Raman spectrometer 54 and/or the light source 52 can be in communication with a controller 60. The controller 60 can determine the concentration of one or more parameters within the bioreactor 10 from the information or data received from the Raman spectrometer 54 and, based on the data, control one or more feeds 36, 38, or 40 and/or control the effluent 28 in order to maintain one or more parameters within preset concentration limits within the bioreactor 10.

The light source 52 in accordance with the present disclosure can emit a coherent light beam having a controlled wavelength or wavelength range. The light source 52, for instance, may comprise a laser, a light emitting diode, or possibly a filament bulb in conjunction with various filters. The light source 52 can be selected based on various factors including the biomaterials being present in the bioreactor 10. The light source 52, for instance, can be adapted to the geometry and sensitivity of the system and can be selected based upon the spectral properties of the biomaterials contained within the reactor. In one embodiment, the light source 52 emits monochromatic light for irradiation of the cell culture within the bioreactor 10. In one embodiment, a single light source 52 may be used. Alternatively, however, the system can include multiple light sources that all operate at the same wavelength or at different wavelengths. In general, the light beam emitted by the light source 52 can have wavelengths in the visible spectrum, the IR spectrum, and/or the NIR spectrum. For instance, the wavelength of light can generally be greater than about 400 nm, such as greater than about 500 nm, such as greater than about 600 nm, such as greater than about 700 nm. The wavelength of the light being emitted by the light source 52 can generally be less than about 1500 nm, such as less than about 1200 nm, such as less than about 1000 nm, such as less than about 900 nm. In one embodiment, the wavelength of the light source can be from about 700 nm to about 850 nm. In one particular embodiment, the light source emits a light beam that has a wavelength of 785 nm. Longer wavelengths of light, for instance, can decrease the intensity of Raman scattered radiation.

The light source 52 can optionally be coupled with one or more lenses, beam splitters, diffraction gratings, polarization filters, band pass filters, or other optical elements selected for illuminating the sample within the bioreactor in a desired manner.

The light source 52 can directly emit a beam of light onto a cell culture contained within the bioreactor 10. Alternatively, radiation from the light source 52 can be transmitted to the sample surface by way of one or more light conveying devices 50, such as optical fibers. The one or more optical fibers can be used to illuminate the surface of the sample continuously or intermittently. In addition, the one or more optical fibers can illuminate generally the same area of a cell culture or can be positioned to irradiate the cell culture at different locations.

In one embodiment, one or more optical fibers used to illuminate the sample within the bioreactor are bundled together with one or more optical detection fibers that are used to collect radiation reflected, emitted, or scattered from the surface. The discreet bundles of illumination and detection optical fibers can be directed to selected areas of the sample surface. The illumination fibers in each bundle can transmit light from light source 52 to the selected area of the surface. Light reflected, emitted, or scattered from that area of the surface can then be collected by the detection fibers. Light transmitted by the detection fibers in each bundle can be assessed in a combined or discrete fashion as desired.

The light conveying device 50 or optical fibers can optionally be coupled to one or more lenses, beam splitters, diffraction gratings, polarization filters, band pass filters, or other optical elements. In one embodiment, for instance, the reflected or scattered light collected by the light conveying device 50 can be in communication with a holographic notch filter, In addition to a holographic notch filter, transmitted, reflected, emitted or scattered light from the illuminated sample can include various other optical elements to facilitate transmission of light and to measure intensity. For instance, other optical elements that can be included in the pathway include lenses, beam splitters, diffraction gratings, polarization lifters, band pass lifters, and the like. When detecting Raman-shifted radiation scattered by a sample, for instance, other suitable filters can include cut-off filters, a Fabry Perot angle tuned filter, an acousto-optic tunable filter, a liquid crystal tunable filter, a Lyot filter, an Evans split element liquid crystal tunable filter, a Solc liquid crystal tunable filter, a liquid crystal Fabry Perot tunable filter, and the like, Suitable interferometers that may be used include polarization-independent imaging interferometers, a Michelson interferometer, a Sagnac interferometer, a Twynam-green interferometer, a Mach-Zehnder interferometer, a tunable Fabry Perot interferometer, and the like. In general, any suitable detector can be used in order to better identify the Raman-shifted scattered radiation received from the sample area.

As shown in FIG. 1, the light conveying device 50 which may comprise one or more optical fibers is connected to the Raman spectrometer 54. The Raman spectrometer 54 includes a detector. For example, scattered light can be transmitted to the detector in a mappable or addressable fashion such that light transmitted from different assessed regions of the sample surface can be differentiated by the detector. Otherwise, light from discrete assessed regions of a sample surface can be transmitted separately to discrete portions of a detector having a linear or two-dimensional array of detector elements.

The Raman spectrometer 54 as shown in FIG. 1 can include the detector. During Raman spectroscopy, the intensity of scattered light is measured and vibrational, rotational, and other low-frequency changes or shifts are observed. In one embodiment, the light scattered from the sample or cell culture is fed through a filter, such as a holographic notch filter, in order to only observe inelastic scattering of the light, In this manner, one can observe the shift in photons from the original wavelength. For example, the interaction of the beam of light with chemical constituents within the cell culture results in laser photons being shifted up or down. The shift in energy gives information about the vibrational mode in the system and can be used to fingerprint different parameters, such as the presence and concentration of various molecules.

In one embodiment of the present disclosure, the Raman spectrometer 54 includes a wavelength separator and a CCD (charge coupled device) camera for better measuring the photon shifts and the intensity of the photon shifts. In this manner, the Raman spectrometer 54 can detect one or more parameters simultaneously within the bioreactor 10.

Raman spectroscopy can provide numerous advantages and benefits when used in accordance with the present disclosure. For example, as described above, Raman spectroscopy processes inelastic light scattering in order to provide specific information as to the presence of particular molecular bonds within the sample. In this way, multiple parameters or components can be measured and monitored simultaneously. Raman spectroscopy is capable of not only identifying the presence of particular parameters, but also capable of providing information regarding the concentration of those parameters. As shown in FIG. 1, Raman spectroscopy can also be used in line without having to remove a sample of the cell culture from the bioreactor 10. Samples also do not require any dilution and the measurement is not impacted significantly by the presence of water. In addition, measurements can be taken continuously or with relatively short time intervals. For instance, measurements can be taken at least every 24 hours, such as at least every 20 hours, such as at least every 15 hours, such as at least every 10 hours, such as at least every 8 hours, such as at least every 4 hours, such as at least every 2 hours, such as at least every hour, such as at least every 30 minutes, such as at least every 10 minutes, such as at least every 5 minutes.

Data from the Raman spectrometer 54 can be fed to the controller 60. The controller 60 and/or the Raman spectrometer can calculate the concentration of one or more parameters of a cell culture contained in the bioreactor 10.

In one embodiment, the processes of the present disclosure can be used to monitor and adjust one or more quality characteristics. For instance, one product quality characteristic that can be monitored and controlled is the glycosylation profile which impacts proteins. Another product quality attribute that can be monitored and varied is the charge variant profile which can indicate the presence of impurities in the product.

Various different parameters can be monitored in accordance with the present disclosure. For example, in one embodiment, the concentration of a nutrient can be monitored. Examples of nutrients that can be monitored include, for instance, glucose, glutamine and/or glutamate. Alternatively, the monitored parameter may relate to the concentration of a waste product. Waste products that can be monitored in accordance with the present disclosure include lactate and ammonium. In addition, various growth and characteristics can be monitored. For example, growth characteristic parameters include the viable cell concentration and the total cell concentration. Finally, the monitored parameter can comprise the concentration of the final product.

In accordance with the present disclosure, in one embodiment, the controller 50 can collect Raman spectra that covers expected process variations that may occur within the bioreactor 10. The controller 60 can then determine the concentration of the one or more parameters using any suitable method. In one embodiment, for instance, the parameter concentrations are measured by comparing the collected spectra with off line reference data. The controller 60 can also develop calibration models using multivariate software. In one embodiment, the controller can also include qualifying predictive models that are developed based on independent data sets.

In one embodiment, the Raman spectra collected by the controller can undergo various statistical analysis or preprocessing prior to determining parameter concentrations. For example, in one embodiment, standard normal variate can be applied to the Raman spectra in order to remove scattering effects. For example, in one embodiment, the standard normal variate can calculate a mean and a standard deviation in order to produce a probability density function. For example, in one particular embodiment, the standard normal variate may include an expected value 0 with variance of 1.

In one embodiment, the standard normal variate can be used in conjunction with applying a first derivative and detrending. Detrending, for instance, can be used to reduce an upward baseline trend caused by fluorescence. After applying the standard normal variate, detrending, and applying the first derivative, a spectral range can then be selected that correlates to the parameter of interest. In one embodiment, the processed spectra can be modeled using partial least squares regression.

The controller 60 may comprise one or more programmable devices or microprocessors. As shown in FIG. 1, the controller 60 can be in communication with the one or more feeds 36, 38 and 40 and with one or more effluents 28. The controller can be configured to increase or decrease the flow of materials and substances into the bioreactor 10 based upon the concentration of one or more parameters. For example, the controller 60 can analyze signals received from the Raman spectrometer 54 and generate output signals capable of controlling one or more input and/or output devices.

In one embodiment, the controller 60 can be configured to selectively increase or decrease the flow of a parameter influencing substance into or out of the bioreactor 10 based upon the measured concentration of a parameter using its Raman spectra. In this manner, the controller 60 can maintain the concentration of the parameter within preset limits. The controller 60 can operate in an open loop control system or can operate in a closed loop control system, where adjustments to input and/or output devices are completed automatically.

In one embodiment, the controller 60 monitors at least two parameters within the bioreactor 10. For instance, the controller 60 can monitor at least three parameters, such as at least 4 parameters, such as at least 5 parameters. For instance, in one embodiment, the controller 60 can monitor from about 2 to about 10 parameters, such as from about 2 to about 6 parameters.

In one embodiment, the controller can be programmed with a predictive model that can predict future concentrations of the one or more parameters to ensure that optimal conditions remain within the bioreactor from the beginning of the process to the end of the process. Programming the controller 60 with a predictive model, for instance, in combination with continuous monitoring, provides potential feedback control for very complex solutions. Using a predictive model, especially in conjunction with monitoring more than one parameter, for instance, can capture as much variability as possible during the entire process of propagating the cell culture.

The predictive model can be created using a design of experiments approach that contains concentrations of desired parameters and associated Raman spectra that covers as much of the process as possible. Further improvements can be obtained by spiking in parameters at varying concentrations and measuring the resulting spectra. In addition, further improvements in predictive models can be obtained by forcibly breaking the correlations that may be present. Inclusion of these data points in the calibration model improves the predictive ability of the model for future data sets. Once the calibration and predictive models from Raman spectra are developed, they can be used for process monitoring and feedback control within the bioreactor. Of particular advantage, the process of the present disclosure allows for the predictive mod& to be used against many different cell cultures and in many different types of bioreactors.

In one embodiment, the bioreactor 10 is for growing a cell culture in a batch process. Alternatively, the bioreactor 10 can be operated in a perfusion process, where fluids are continuously removed and replenished. The amount of time the cell culture is propagated can vary depending upon various factors. In general, for instance, the cell culture can be propagated for a period of time of from about 6 days to about 30 days, such as from about 8 days to about 20 days. In one embodiment, concentration measurements of one or more parameters can be obtained in the initial stages of cell growth. For instance, Raman spectra can be obtained for different parameters over the first 1 to 6 days, such as over the first 2 to 4 days. The controller 60 can receive this information and begin building predictive data that predicts future concentrations of each of the monitored parameters. After receiving the information for a period of time, the controller 60 can then selectively increase or decrease a parameter influencing substance that may be fed or withdrawn from the bioreactor 10. For example, in one embodiment, the controller 60 can begin making selective adjustments to the bioreactor after 2 to 4 days of receiving data and based upon how the concentrations of the parameters fit within the predictive model.

For example, in one embodiment, the system can be configured to monitor glucose concentration in conjunction with at least one other parameter, such as lactate concentration. Based upon the monitored concentration of both parameters, the controller 60 can then automatically make adjustments to the flow of one or more nutrient media into the bioreactor 10. The nutrient media, for instance, may contain glucose. In this manner, glucose concentrations can be maintained within preset parameters in conjunction with maintaining lactate concentrations within preset parameters. In one embodiment, for instance, glucose levels are maintained so as to minimize fluctuations in lactate levels and maintain lactate levels below desired set points.

In an alternative embodiment, the controller can be used to control the effluent rate in a continuous perfusion bioreactor to maintain parameter levels below a desired set point, such as to maintain lactate levels below a desired set point.

In addition to monitoring one or more parameters through Raman spectroscopy, the controller can control various other process conditions. For instance, the controller can be in communication and control thermocirculators, load cells, control pumps, and receive information from various sensors and probes. For instance, the controller may control and/or monitor the pH, the oxygen tension, dissolved carbon dioxide, the temperature, the agitation conditions, the alkali condition, the pressure, foam levels, and the like. For example, based on pH readings from a pH probe, the controller may be configured to regulate pH levels by adding requisite amounts of acid or alkali. The controller may also use a carbon dioxide gas supply to decrease pH. Similarly, the controller can receive temperature information and control fluids being feed to a water jacket surrounding the bioreactor for increasing or decreasing temperature.

Many different cell cultures can be maintained or propagated using the process of the present disclosure. For instance, in one embodiment, the bioreactor can contain mammalian cells. Alternatively, the process of the present disclosure can be used to harvest cells for cell therapy. For example, in one embodiment, the bioreactor can contain stem cells, T cells, immune cells, and the like.

Through the process of the present disclosure, cell cultures can be grown with excellent product characteristics. For example, cell cultures can be grown with excellent viability characteristics. For example, viability can be measured by dividing the viable cell count with the total cell count, which are two parameters that can both be measured using the Raman spectra. In accordance with the present disclosure, cell cultures can be grown in accordance with the present disclosure having a viability ratio as described above of greater than about 0.6, such as greater than about 0.7, such as greater than about 0.8, such as greater than about 0.9. In fact, the viability ratio can be greater than about 0.94, such as greater than about 0.96, such as greater than about 0.98.

The present disclosure may be better understood with reference to the following examples.

Example No. 1

Three different CHOK1SV GS-KO™ cell lines producing different monoclonal antibodies (mAbs) were used during this study. Two cell lines were used for calibration model development and the remaining cell line was used for model qualification. All cell lines were cultured on platform media and feeds over a 15-day period. All cell cultures for the calibration models were performed in four stirred tank reactors (STRs) with a 5 liter working volume. Each calibration cell culture had two controls operating at a target residual glucose concentration of ≈3 g/L. To expand the operating range for glucose two STRs were operated with ≈1 g/L extra initial glucose and maintained at a target residual glucose concentration of 1 g/L. Additionally, data from one round of abnormal cell culture in four STRs with a 5 liter working volume was included to account for metabolite and cell concentrations well outside of expected ranges for the platform process. For model qualification two STRs were operated with a 5 liter working volume, while one STR was operated with a 10 liter working volume to assess model scalability.

Offline Analytics

During culture, offline samples (≈20 mL) were taken twice daily from each culture for analysis of metabolites and cell growth. Offline analysis of glucose, lactate, glutamate, and ammonium were performed using a NOVA Bioprofile 400 (NOVA Biomedical). Offline analysis of VCC (viable cell concentration) and TCC (total cell concentration) was performed using a Vi-Cell XR (Beckman Coulter). From day 4 of culture onwards, twice daily aliquots (≈2 mL) were saved from cell culture supernatant for product concentration analysis. Product concentration was analyzed via Protein A HPLC.

Inline Raman spectra were collected using a RAMANRXN2™ (RXN2) system from Kaiser Optical System, Inc. with a 785 nm laser using four 420 mm bio-optic probes (1 probe per bioreactor). Raman spectra were generated from 150 scans with a 5 second exposure time for a total analysis time of ≈12.5 minutes. For cell cultures used to build the calibration set, inline Raman spectra were collected twice daily from each bioreactor and coincided with measurement of the offline samples. Total collection time for inline Raman spectra from all four probes was ≈1 hour.

Figure 2A:
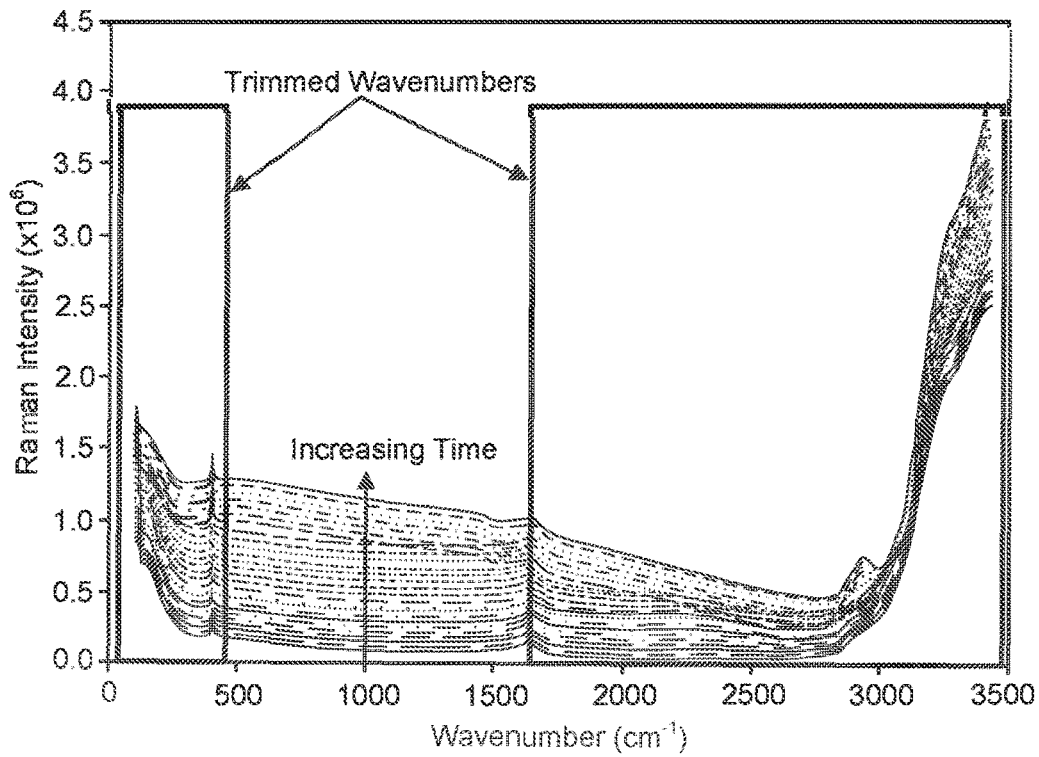
FIG. 2 through FIG. 20 are graphical representations of some of the results obtained in the examples below.
Figure 2B:
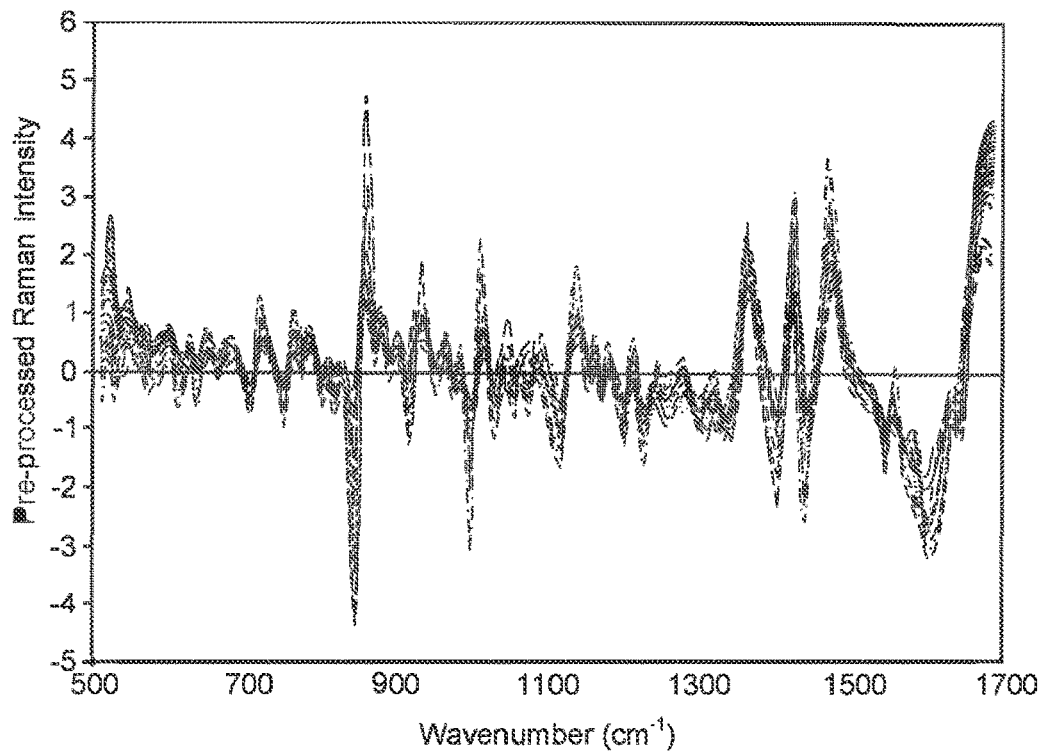
Figure 3A:
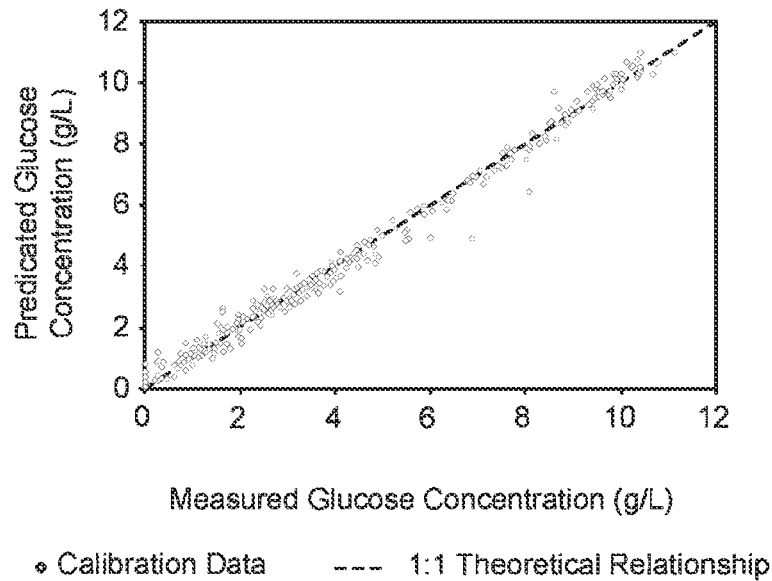
Figure 3B:
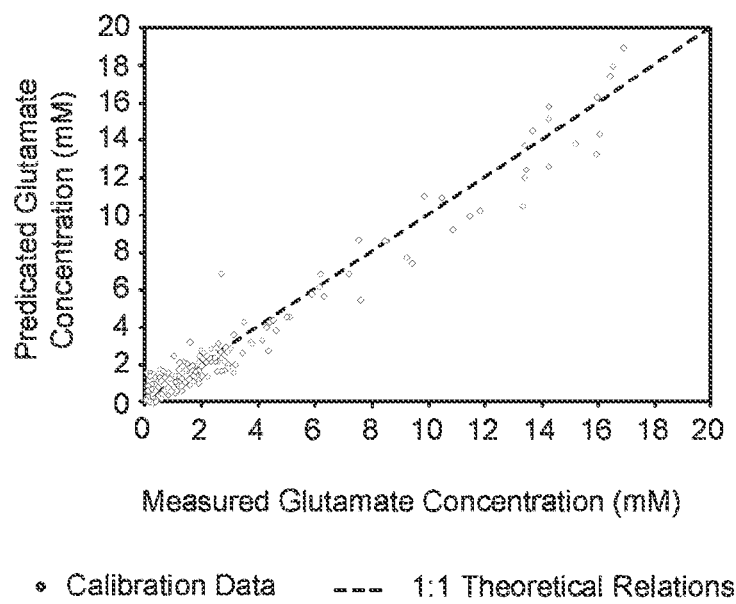
Figure 3C:
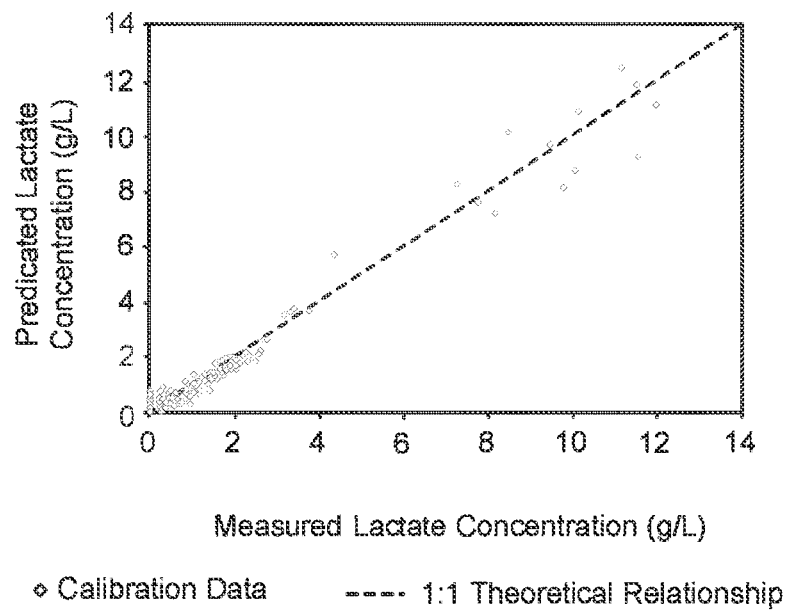
Figure 3D:
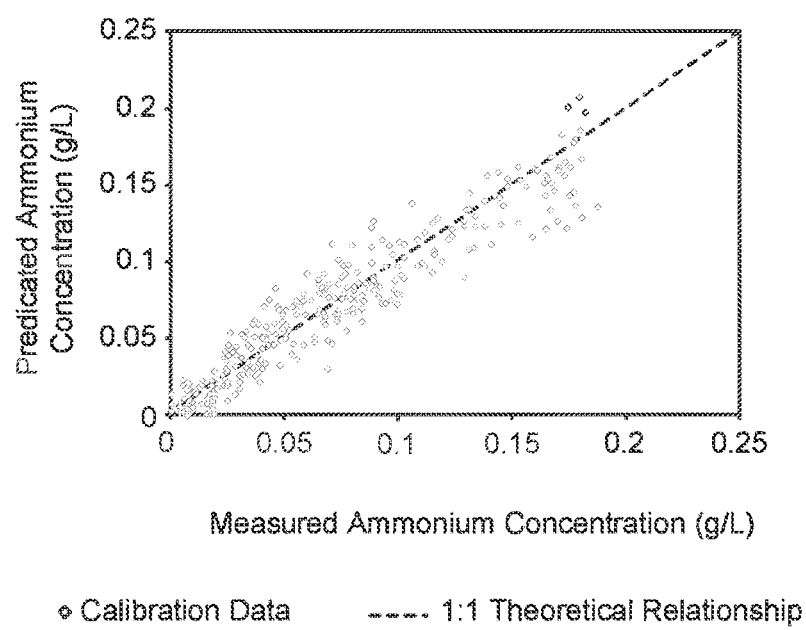
Figure 3E:
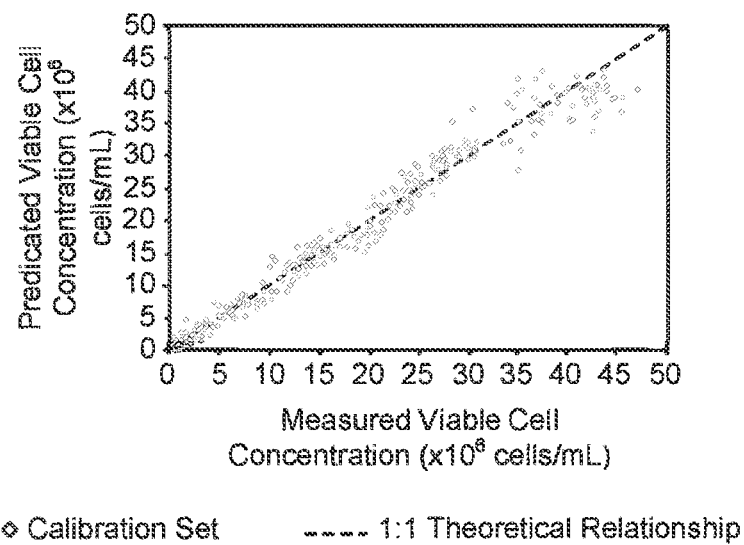
Figure 3F:
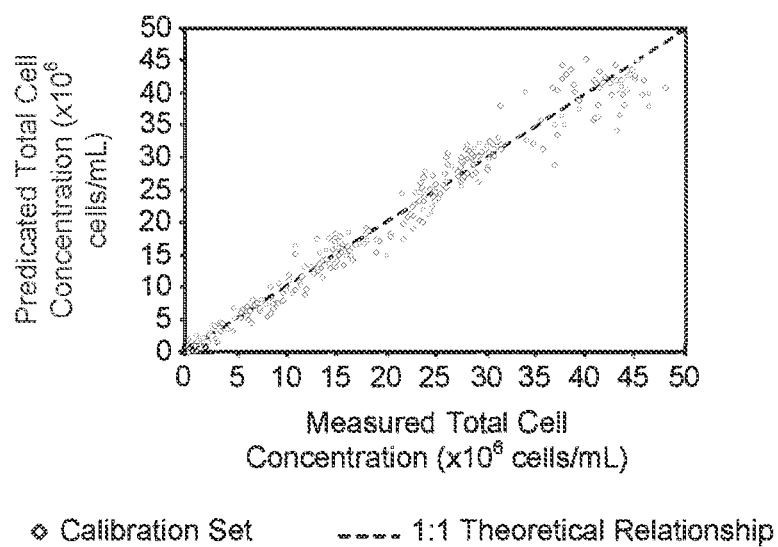
Figure 3G:
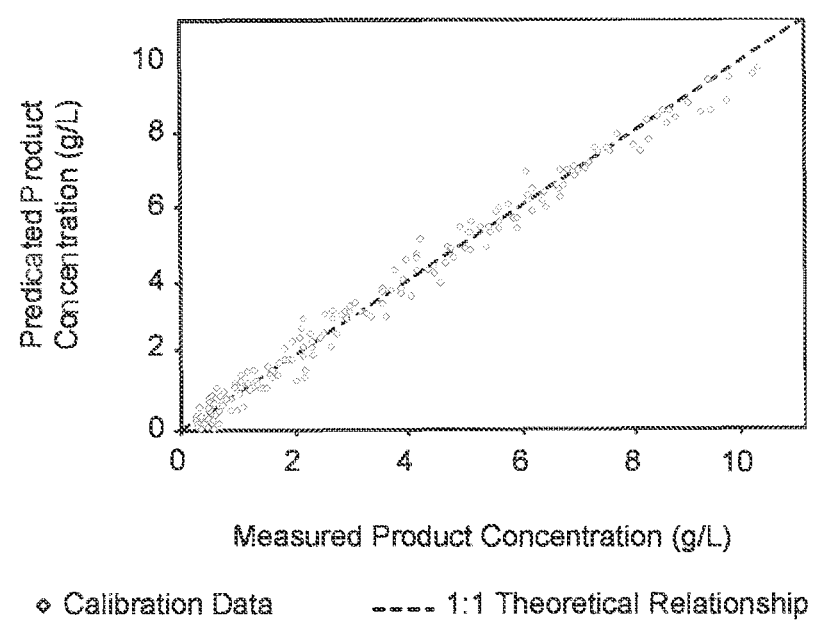

For model qualification inline Raman spectra were collected every three hours and compared to the offline measurements. The extra spectra collected in between offline sampling during the qualification run allowed for trending the measured parameters over time and offered additional insight into the ability of the developed models to monitor where matched with their respective offline measurements prior to being imported into SIMCA v13.0.3. Next regions outside the fingerprint region were removed (<500 cm-1 and >1700 cm-1 for most models) to prevent these signals being given inappropriate weight in the resulting models (FIG. 2A). If left in these regions of noise can mask the impact of Raman regions correlated to changes in metabolite concentration (e.g., residual glucose concentration) hindering model robustness. After spectral trimming, different combinations of spectral pre-processing were applied and PLS models were constructed. The raw spectra from the different cell culture runs showed a baseline shift over the course of the experiments which was reduced by application of a 1st derivative filter (FIG. 2B). Moreover, derivative filters were required to create the best models for all parameters in this study. It should be noted that the actual spectral pre-processing utilized is parameter dependent. The resulting model statistics were compared and the models with the lowest RMSEE/RMSECV were saved for use in monitoring the qualification set.

Model Calibration

Offline data from 12 cell culture runs utilizing a platform process in 5 liter STRs were combined with their respective Raman spectra and used to produce calibration models for glucose, glutamate, lactate, ammonium, viable cell concentration (VCC), total cell concentration (TCC), and product concentration (Table 1). In general, the models had low RMSEE/RMSECV values with R2Y>0.90 for all parameters. Additionally, all models had a relatively low number of latent variables (LV's), with the exception of ammonium. The high number of LV's for the ammonium model may indicate that the model is over fit for this parameter (R2cv=0.89). In building the models offline data and spectra were collected that covered ranges outside of normal operating conditions for the platform process. This was done to avoid creating situations where the models would be required to extrapolate. Calibration model plots for predicted glucose, glutamate, lactate, ammonium, VCC, TCC, and product concentrations versus their respective offline reference methods, indicate that in general all models correlate well with the measured values (FIG. 3).

TABLE 1

Calibration Model Statistics

| Parameter | N | LV | $R^2Y$ | $R^2_{CV}$ | RMSEE | RMSECV | Range |
|---|---|---|---|---|---|---|---|
| Glucose (g/L) | 344 | 5 | 0.99 | 0.99 | 0.33 | 0.39 | 0.00-11.14 |
| Lactate (g/L | 344 | 5 | 0.97 | 0.96 | 0.34 | 0.36 | 0.00-12.47 |
| Glutamate (mM) | 342 | 6 | 0.96 | 0.94 | 0.71 | 0.79 | 0.00-19.92 |
| Ammonium | 344 | 9 | 0.94 | 0.89 | 0.015 | 0.017 | 0.000-0.208 |
| VCC ($\times 10^6$) | 344 | 6 | 0.97 | 0.97 | 2.24 | 2.40 | 0.43-47.10 |
| TCC ($\times 10^6$) | 344 | 6 | 0.98 | 0.97 | 2.21 | 2.34 | 0.44-48.00 |
| Product | 267 | 6 | 0.99 | 0.98 | 0.48 | 0.49 | 0.04-10.15 |

Model Qualification & Scalability

Figure 4A:
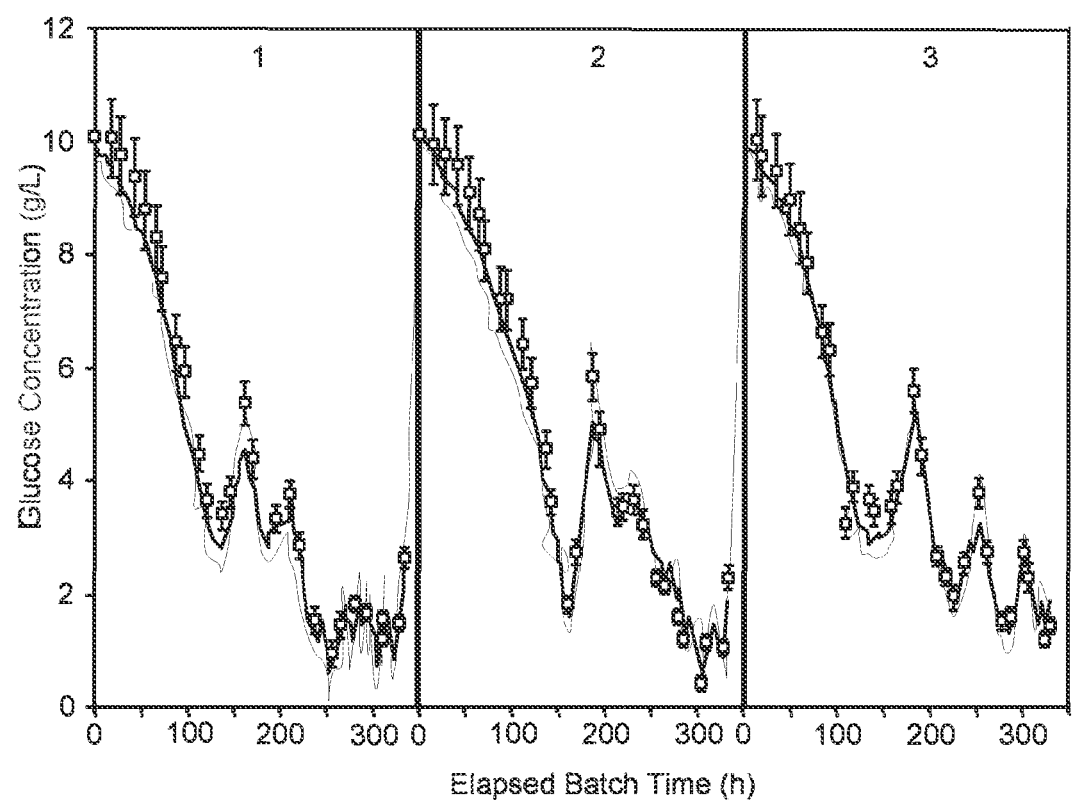

Models were qualified using a cell line not included in the calibration models. All qualification runs were performed under normal operating conditions for the platform process. To investigate the potential scalability of the developed model a 10 liter culture was also performed. The resulting prediction versus offline reference method profiles for all three qualification runs are shown in FIG. 4. The error bars for predicted values are ± the RMSEP for each culture run. The error bars for the offline reference method are ± precision as specified by the vendor. All models were able to monitor changes in the desired parameters with relatively low RMSEP values. (Table 2).

is attributed to utilizing a calibration dataset with a concentration range for lactate that was well outside of what is typically observed for this process (Table 1). As PLS models are unable to extrapolate data, ensuring that any potential excursion is included during calibration helps to increase the robustness of the model to atypical culture performance (FIG. 4Cii).

The predictive model developed for ammonium was capable of monitoring changes in the ammonium concentration across all cultures with an average RMSEP of 0.03 g/L versus an average process ammonium concentration of 0.09 g/L. A slight under prediction was observed for one cell culture towards the end of the run (FIG. 4Dii). This is likely

TABLE 2

Summary Model Statistics for Qualification Round

| Parameter | N | Concentration Range | $R^2_p$ i | ii | iii | RMSEP i | ii | iii |
|---|---|---|---|---|---|---|---|---|
| Glucose (g/L) | 87 | 0.44-10.12 | 0.99 | 0.98 | 0.99 | 0.47 | 0.43 | 0.41 |
| Lactate (g/L) | 87 | 0.00-3.76 | 0.96 | 0.97 | 0.94 | 0.30 | 0.22 | 0.18 |
| Glutamate (mM) | 87 | 0.00-5.34 | 0.60 | 0.18 | 0.56 | 0.97 | 1.63 | 0.89 |
| Ammonium (g/L) | 87 | 0.009-0.242 | 0.88 | 0.81 | 0.93 | 0.02 | 0.04 | 0.02 |
| VCC ($\times 10^6$ cells/mL) | 87 | 0.51-34.87 | 0.98 | 0.99 | 0.99 | 1.90 | 2.32 | 1.48 |
| TCC ($\times 10^6$ cells/mL) | 87 | 0.51-35.58 | 0.98 | 0.99 | 0.99 | 2.25 | 1.97 | 1.34 |
| Product Concentration (g/L) | 66 | 0.00-4.70 | 0.94 | 0.94 | 0.99 | 1.21 | 0.75 | 0.98 | i = 5 L Run 1, ii = 5 L Run 2, and iii = 10 L Run

The predictive model developed for glucose was found to satisfactorily predict concentrations of glucose over all three cell cultures with an average RMSEP of 0.44 g/L versus an average process glucose concentration of 5.18 g/L. Importantly the developed models were capable of monitoring changes in residual glucose concentration as cultures were fed a concentrated glucose feed (FIG. 4A). Careful glucose feeding to CHO cell cultures has been shown to increase product quality. The percent glycation can be reduced by approximately half through the control of residual glucose, made possible through inline Raman monitoring.

The predictive model developed for lactate satisfactorily monitored changes in lactate concentration across all three cultures with an average RMSEP of 0.23 g/L versus an average process lactate concentration of 0.81 g/L. A slight over prediction of lactate was observed towards the end of one culture (FIG. 4Ci). This may be due to the measured values being below the lower range of offline reference method, which defaults to a value of 0 g/L. Importantly, it was able to measure a shift in lactate concentration outside of expected ranges for the platform process (FIG. 4Cii). This due to the concentration range for ammonium in the calibration cultures being <0.2 g/L causing the model to extrapolate these values (Table 1, FIG. 4D). Inclusion of more offline reference measurements covering a broader range of ammonium concentrations should allow a more robust model with an improved ability to monitor changes in ammonium concentration.

The predictive models developed for VCC and TCC were capable of monitoring changes across all three qualification cultures with average RMSEP's of $1.90 \times 10^6$ and $1.85 \times 10^6$ cells/mL versus average process values of $1.80 \times 10^6$ and $1.86 \times 10^6$ cells/mL respectively. Importantly the models were able to predict VCC and TCC within the errors of the offline reference method for the majority of the qualification cultures. Discrepancies between predicted and measured VCC during the stationary phase of growth may be a result of dilution errors associated with sample preparation for Vi Cell XR analysis at these high cell concentrations. Despite these errors the developed model for VCC is considered to be suitable to provide online control of nutrient feeds to fed-batch and perfusion cell cultures, which historically have been adjusted based on daily VCC measurements and using inline capacitance probes. While capacitance based predictions were shown to be effective, engineering constraints limit the number of available probe ports in typical GMP bioreactor vessels. In this case the use of a single probe to monitor multiple parameters for feedback control of nutrient feeds is desirable, giving inline Raman probes a clear advantage.

Figure 4B:
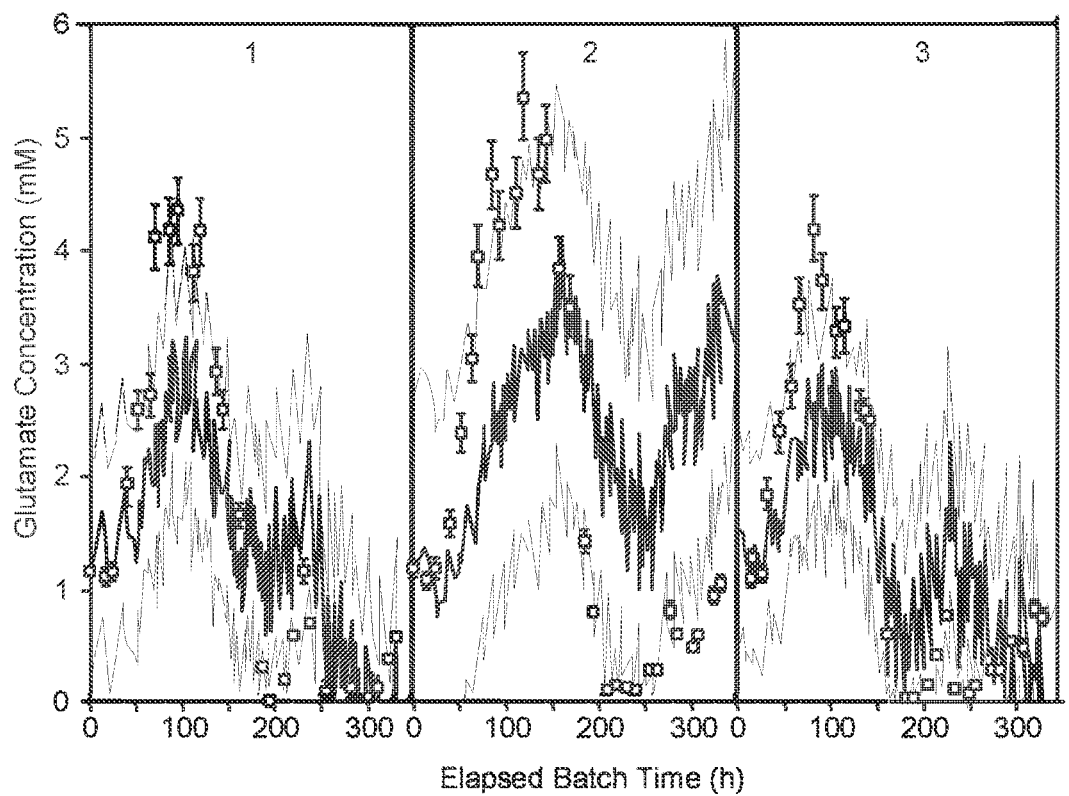
Figure 4C:
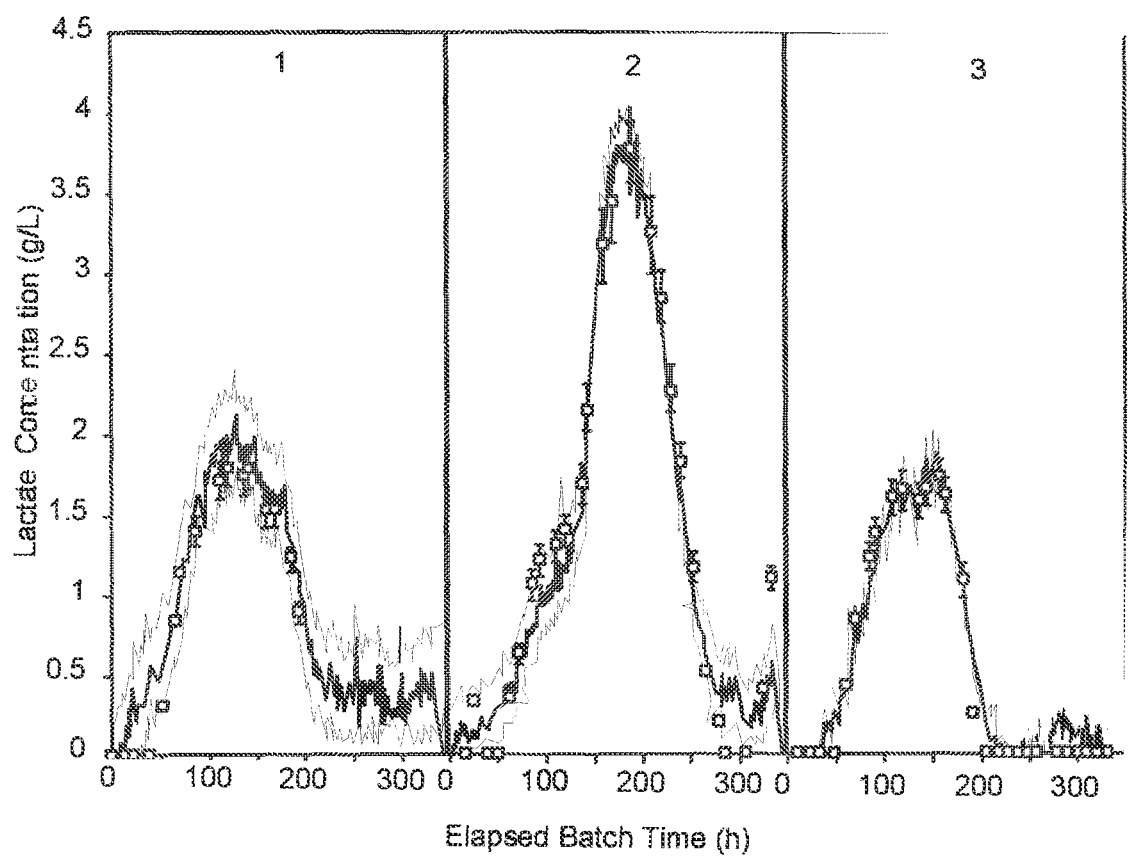
Figure 4D:
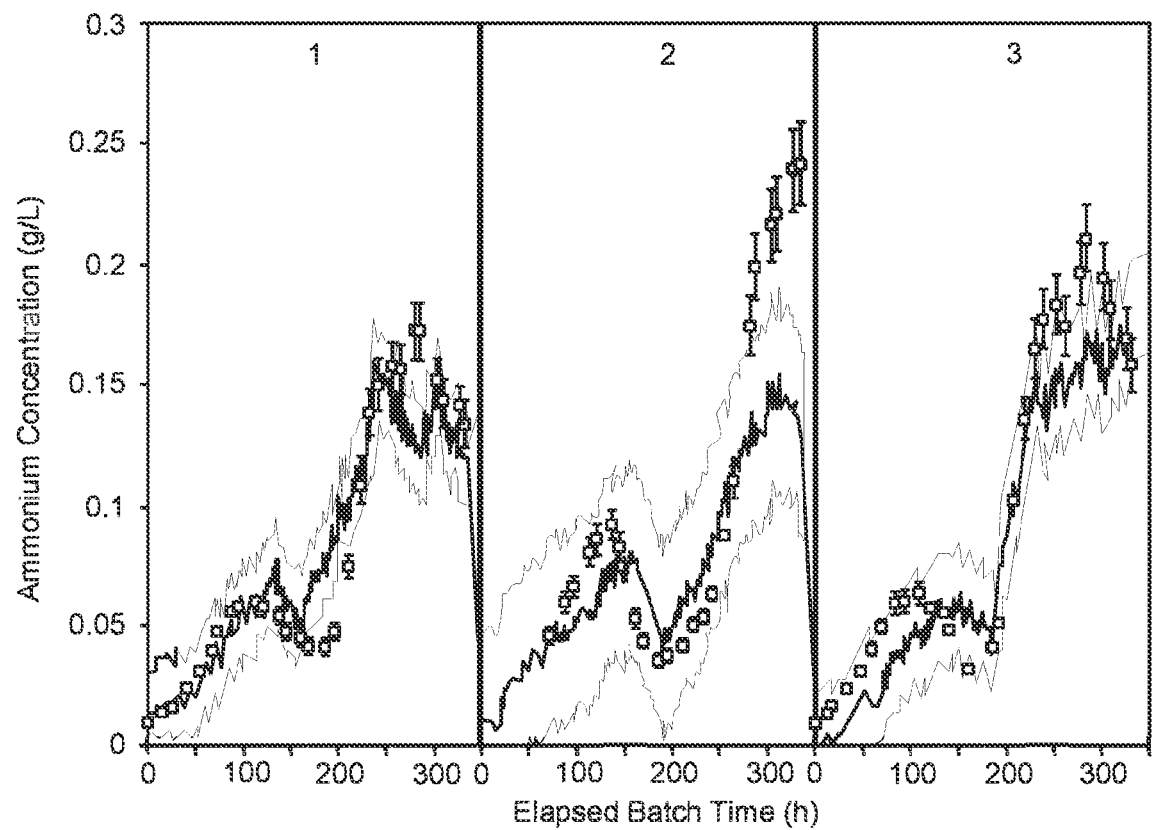
Figure 4E:
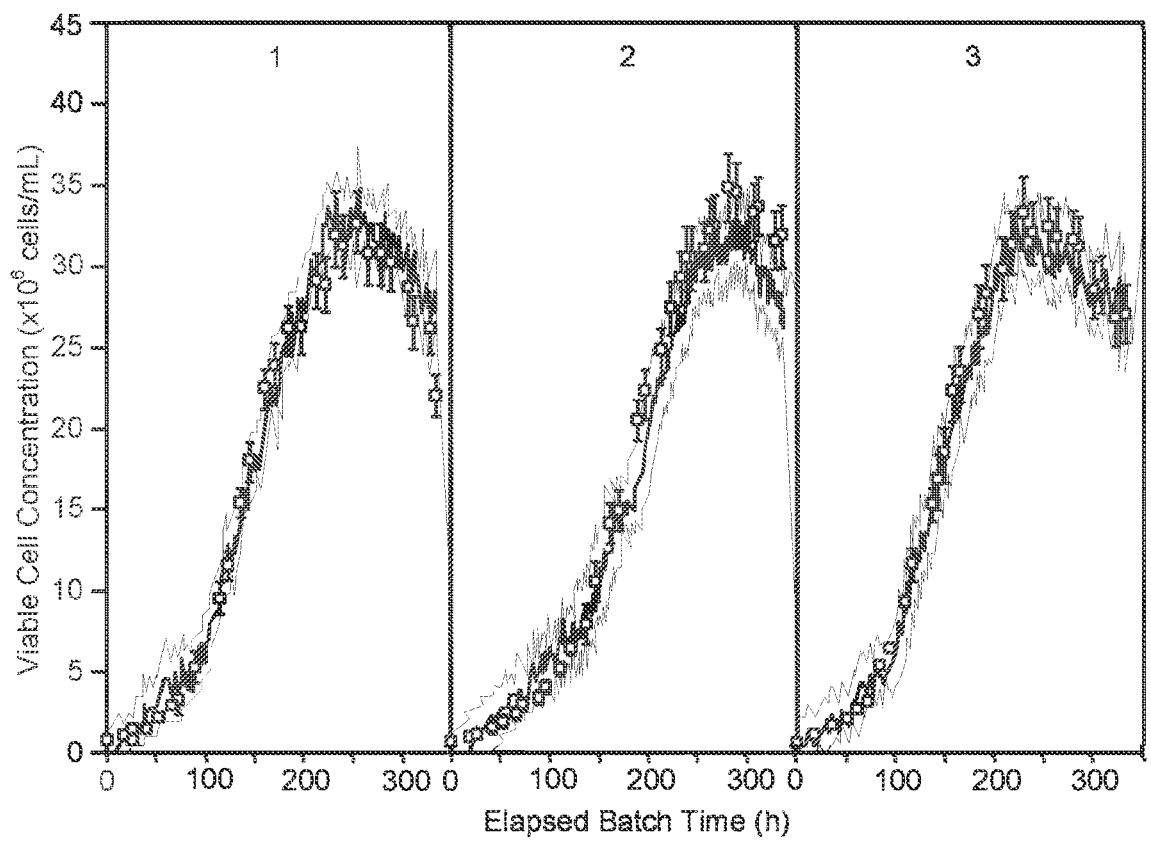
Figure 4F:
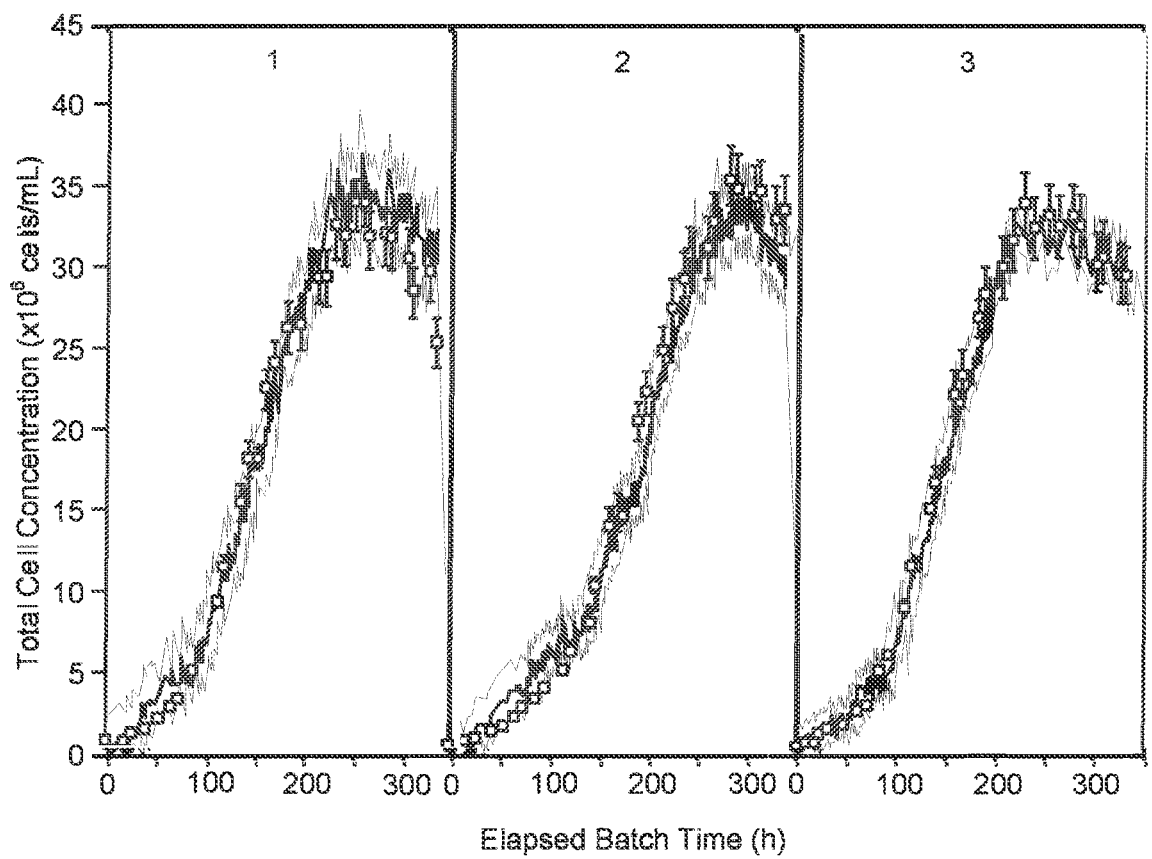
Figure 4G:
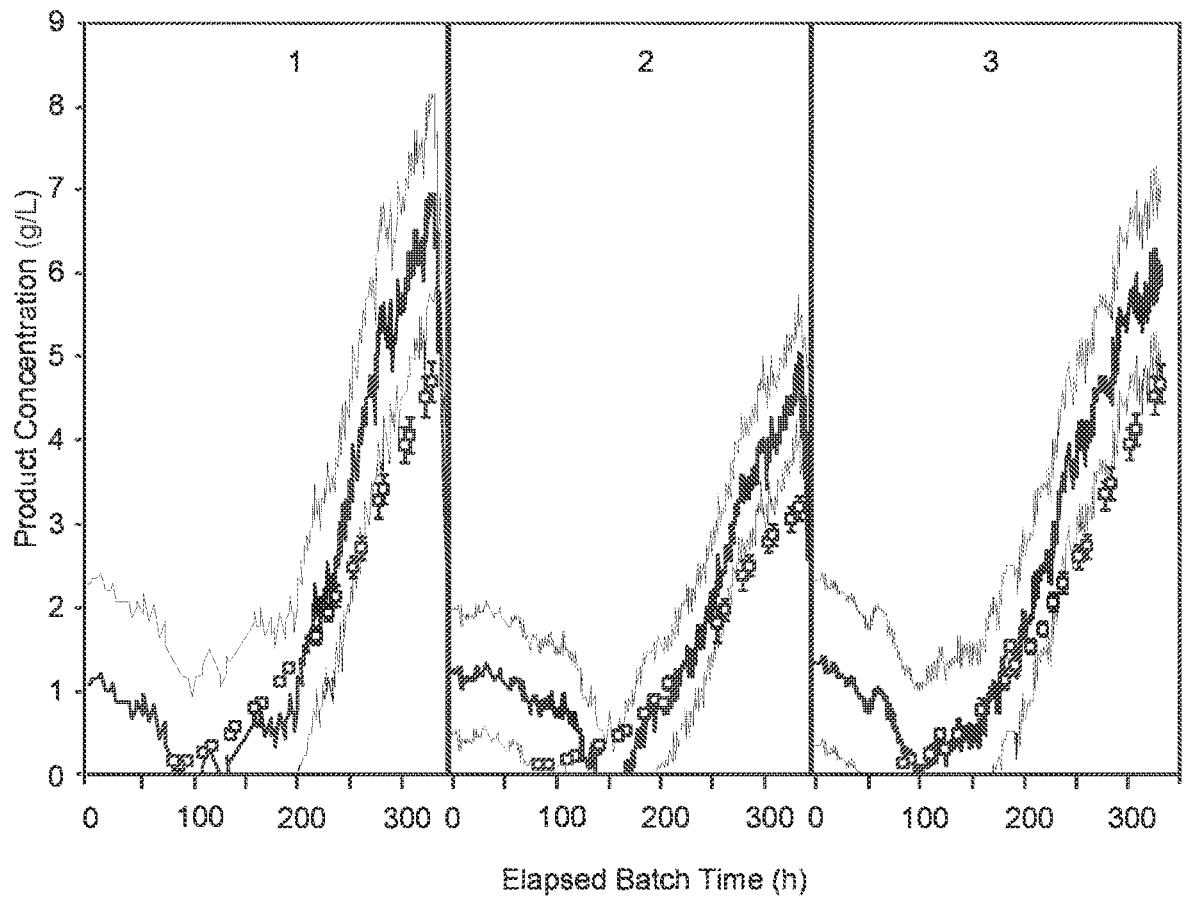

The predictive model developed for glutamate monitored changes across the qualification cultures with an average RMSEP of 1.61 mM versus an average process glutamate concentration of 1.64 mM (FIG. 4B). Any error in the glutamate model may be due to the measurement error associated with glutamate detection from the NOVA Bioprofile 400. Accurate measurement by the offline reference method may be required to build robust PLS models from inline Raman spectra. As such, the glutamate model could be improved through the use of a more accurate reference method for this component.

The predictive model developed for product concentration had an average RMSEP of 0.98 g/L versus an average product concentration of 1.74 g/L for the process (FIG. 4). Any errors in the prediction of product concentration may be attributed to a lack of data from the early time points of cell culture used for model development. At the beginning of cell culture, the model predicted the presence of a substantial amount of product when very little is expected to be present (FIG. 4G). This discrepancy could be due to the fact that the calibration model does not contain offline product concentration data prior to day 4 of culture. The inclusion of such data may enable the development of an improved predictive model. It is possible that any prediction errors later in the culture indicate that the model built from the Raman spectra is not directly measuring changes in product concentration, but estimating product concentration based on other factors that are correlated with this parameter. For instance, product concentration is correlated with time and VCC, however this correlation varies significantly between cell lines and products. If the model was estimating product concentration from correlations with time and VCC this may help explain why the model was slightly off when predicting product concentration at later time points, for a cell line not included in the calibration model (FIG. 4G). Additionally, different mAbs can have different amino acid sequences which may yield different Raman signals. This could in turn impact the ability of the developed model to predict a different mAbs concentration during cell culture.

Inline Raman spectra from four different Raman probes were used to create calibration models from offline reference measurements of two CHOK1SV GS-KO™ cell lines cultured on a platform media that covered the expected variation in the process metabolites, cell growth, and product concentration. Calibration models were capable of predicting the concentrations of glucose, lactate, ammonium, viable cell concentration and total cell concentration within the error of the offline reference methods for three rounds of qualification cell culture at different scales. Furthermore, these generic models were found to be independent of the CHOK1SV GS-KO™ cell line used for these process parameters. Robust models may be satisfactorily made for glutamate and product concentration with small changes. More sensitive offline methods and inclusion of more data could improve the models for glutamate and product concentration respectively.

Figure 5:
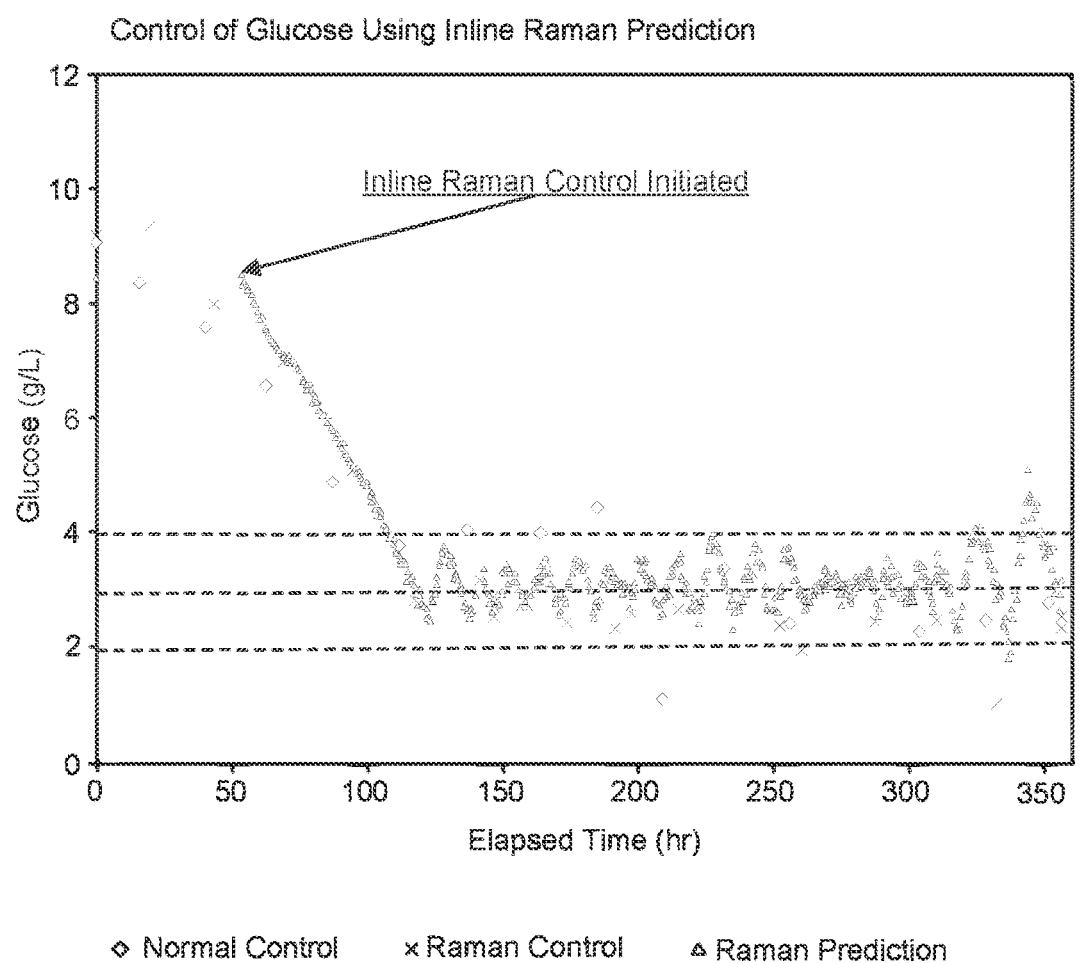

Through the process of the present disclosure, feedback control of nutrient feeds allows for careful monitoring and automatic adjustment of cell cultures for improving output in quality. Referring to FIG. 5, glucose concentration is illustrated over time. As shown, the process of the present disclosure is capable of maintaining glucose levels within carefully controlled limits, especially in comparison to prior systems that simply adjust the feed rate of glucose based on daily measurements. As shown in FIG. 5, the continued adjustment of the glucose feed from a Raman signal leads to a more consistent glucose profile around the target for the majority of the culture.

Figure 6:
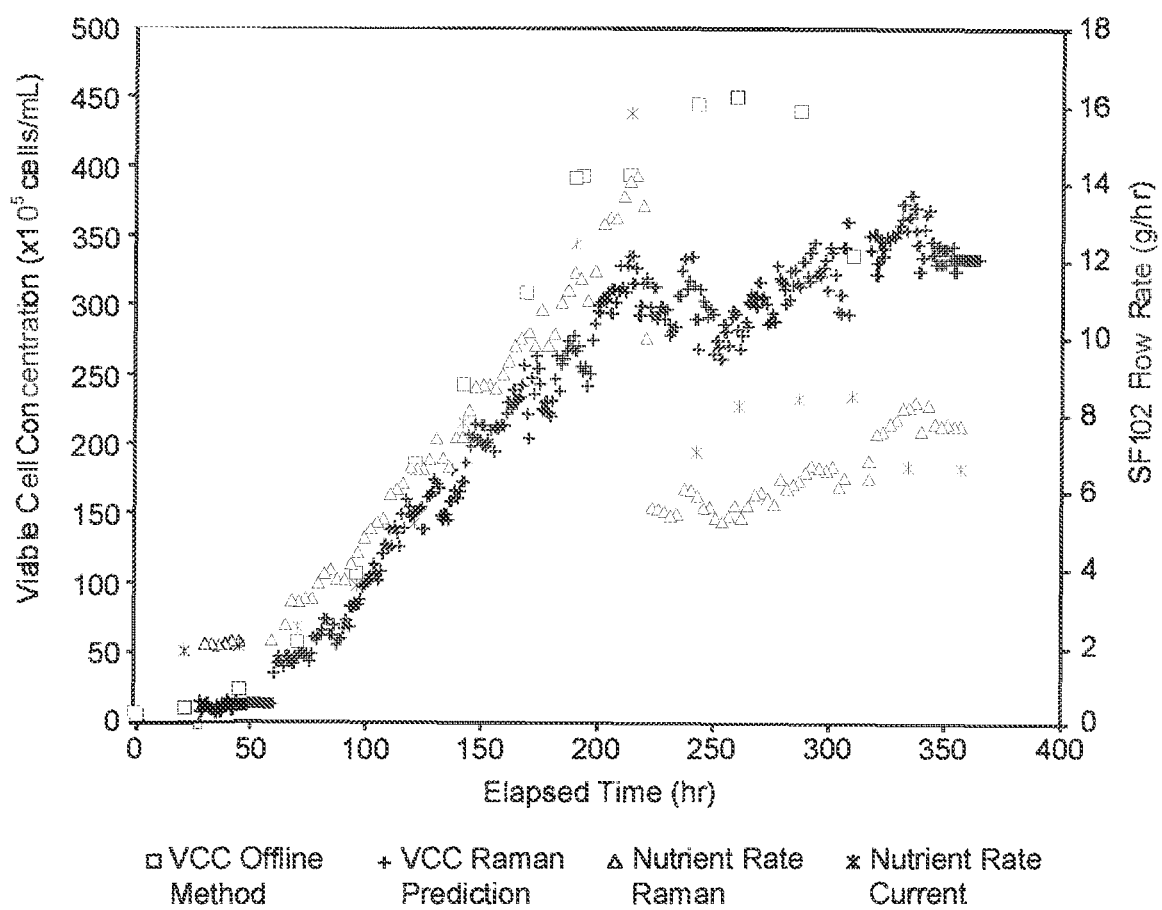

Control of a complex nutrient feed tied to variable cell concentration in accordance with the present disclosure is also shown in FIG. 6.

Attached also is further information and illustrations regarding the system and process of the present disclosure.

The development of generic models demonstrates that it is possible to apply Raman spectroscopy for measuring key culture metabolites in an industrial platform process. Moreover, these models can help realize the potential of automated process control in clinical manufacturing operations where processes are run only once or twice at GMP scale. Finally, the successful monitoring of the highlighted parameters using the developed models should enable the use of inline Raman probes for continuous monitoring and control of nutrient feeds to provide more robust and consistent processes at both the clinical and commercial manufacturing scales.

Example No. 2

Human mesenchymal stem cells (MSCs) were cultured in a stirred tank bioreactor containing microcarriers. The culture period totaled eight days. For the first four days, cells were incubated in MSC media at a glucose concentration of 2 g/L. Starting on day 4 of culture, and through day 8, continuous perfusion was initiated, replacing the old media with fresh MSC media at a glucose concentration of 4 g/L. Over the course of these eight days, samples were periodically drawn from the bioreactors and glucose, lactate, and ammonium concentrations were measured from fresh samples using the Nova BioProfile Flex instrument. Inline Raman spectra were collected using a RamanRXN2™ system from Kaiser Optical System, Inc. with a 785 nm laser scanning through a specific spectral range, with 420-2465 $cm^{-1}$ used for modeling.

Model Calibration:

Four 5 L bioreactors containing 3.5 L of culture were run for model calibration. The Raman instrument used a 10 second exposure time, and for each measurement collected 75 accumulations. Measurements were taken every 30 minutes. A total of 47 (N=47) samples were measured on the Nova from the four runs.

Figure 7:
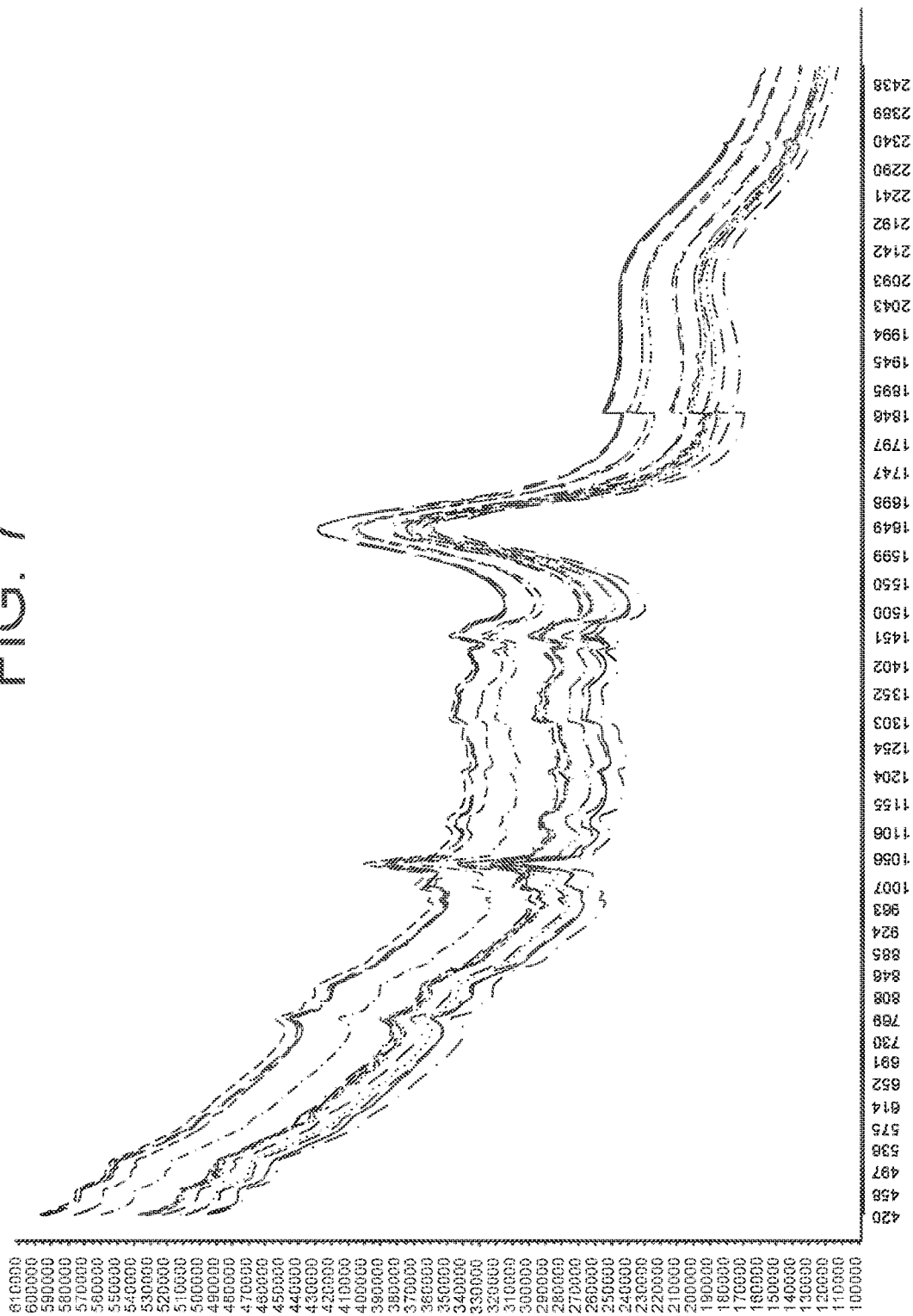
Figure 8:
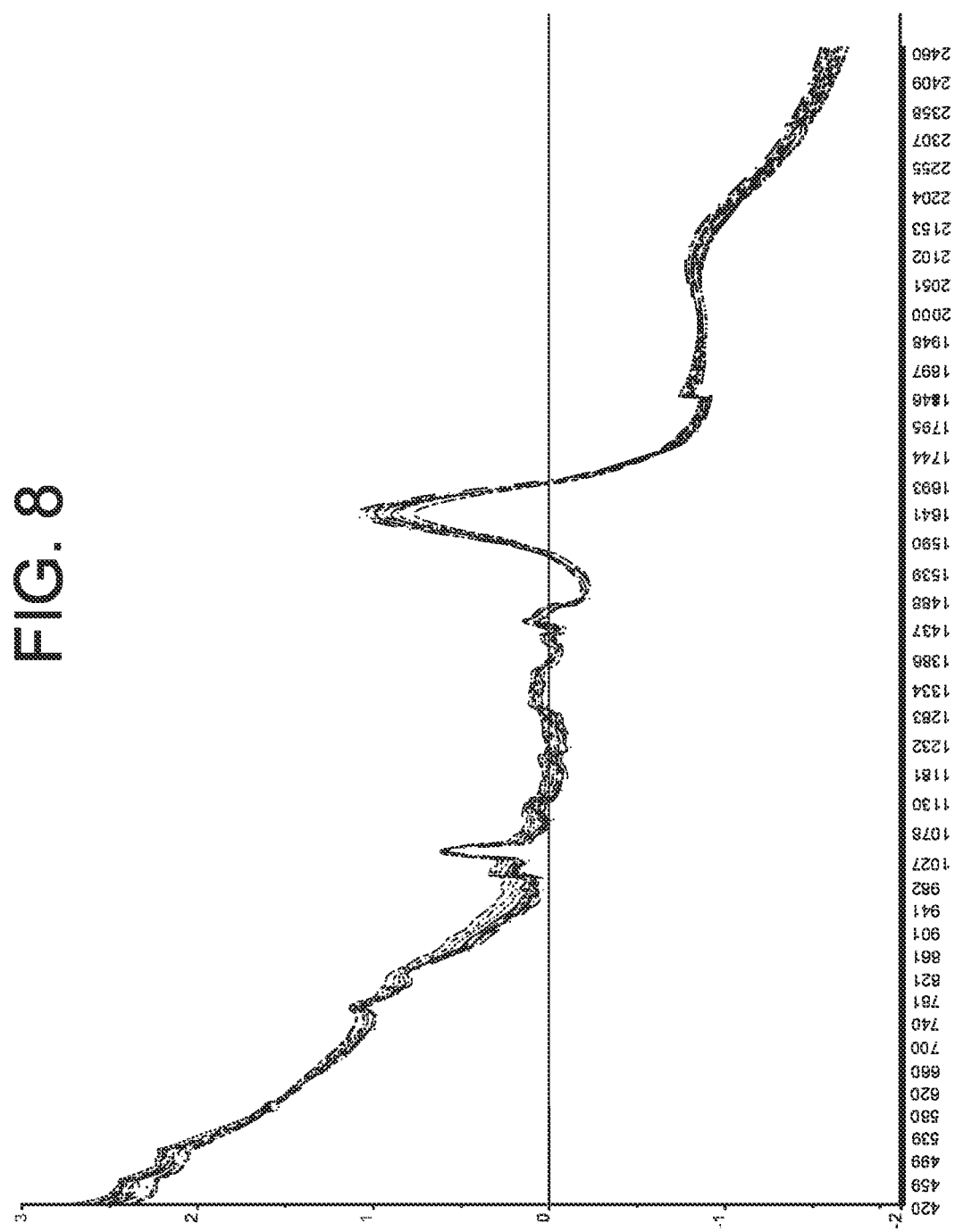
Figure 9:
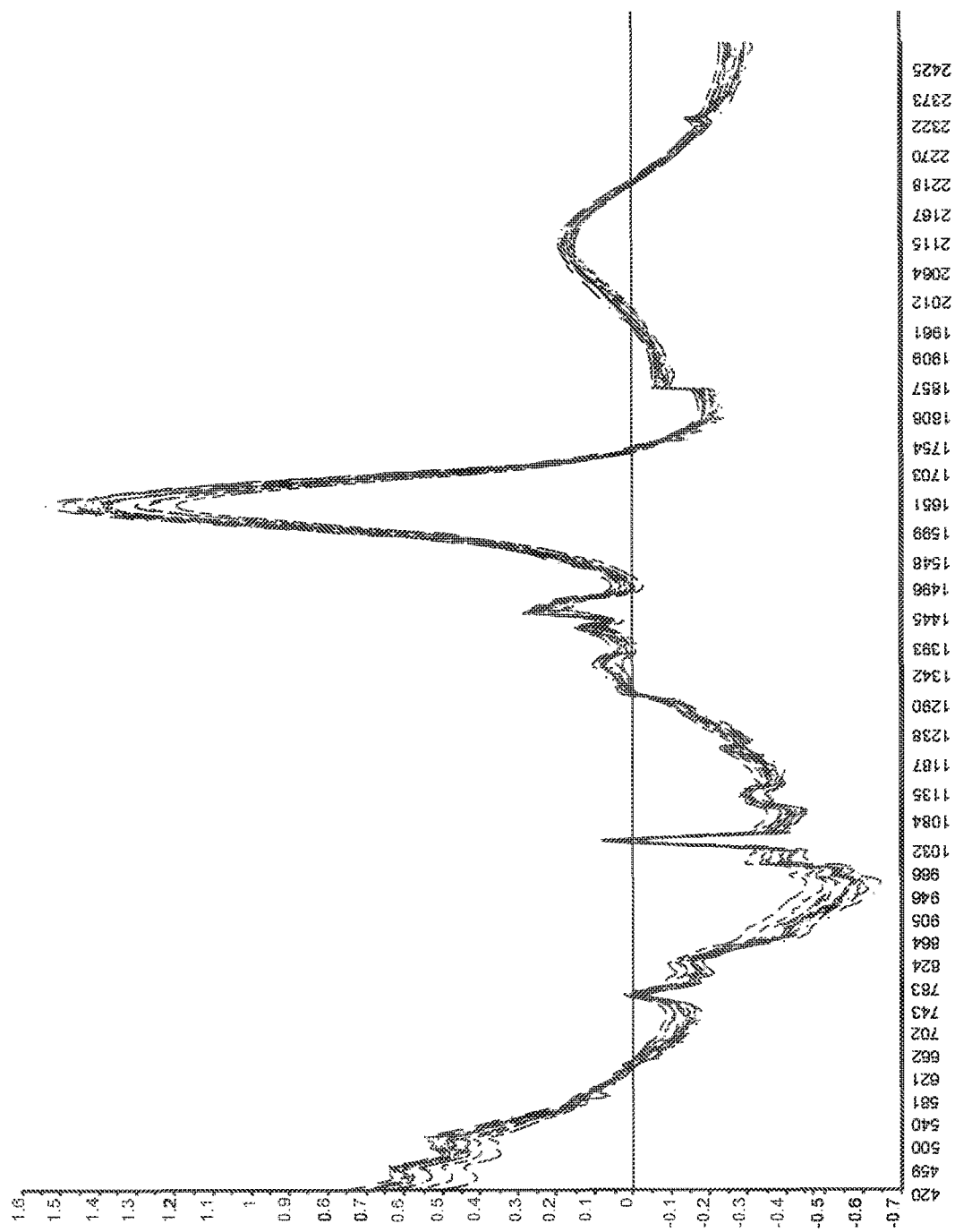
Figure 10:
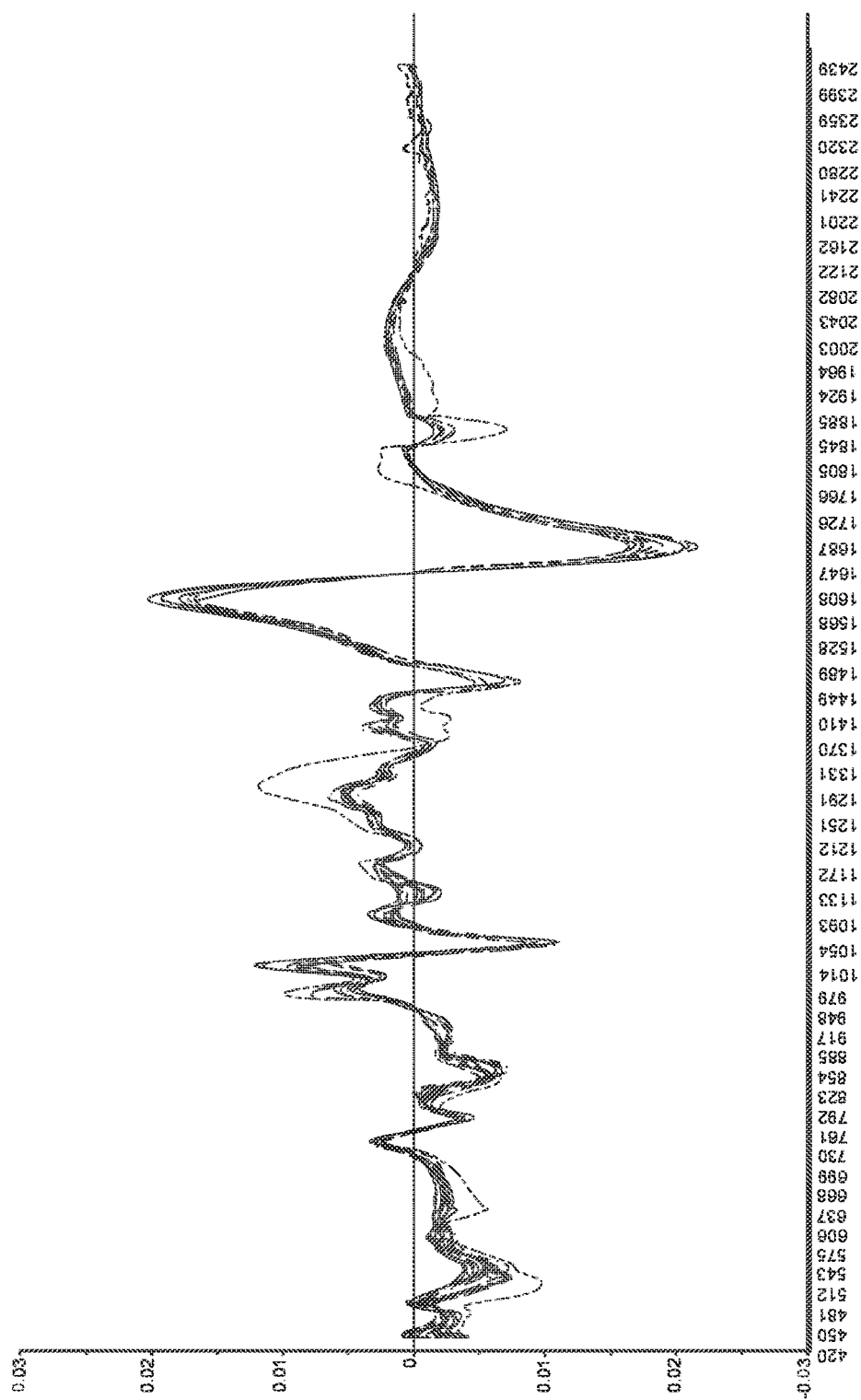

Preprocessing was performed by four steps: applying the Standard Normal Variate (SNV), detrending, applying the first derivative, and choosing a spectral range correlating to the molecule of interest. FIGS. 7-10 illustrate these preprocessing steps as applied to one of the qualification runs. FIG. 7 shows the raw, unprocessed spectra. FIG. 8 shows the same spectra as FIG. 7, but after applying SNV. FIG. 9 shows the same spectra after SNV and detrending. FIG. 10 shows the same spectra after SNV, detrending, and applying a 1st derivative.

The processed spectra were then modeled using partial least squares regression (PLS-R). Table 1 summarizes the statistics of the resulting models. Only 17 samples of ammonium were included in the PLS-R model because they had values of zero.

TABLE 1

Model calibration statistics

| Parameter | N | LV | $R^2Y$ | $R^2_{CV}$ | RMSEE | RMSECV | Range |
|---|---|---|---|---|---|---|---|
| Glucose (g/L) | 47 | 3 | 0.92 | 0.90 | 0.25 | 0.29 | 0.15-4.02 |
| Lactate (g/L) | 47 | 3 | 0.96 | 0.95 | 0.13 | 0.17 | 0.10-1.86 |
| Ammonium (mmol/L) | 17 | 4 | 0.94 | 0.91 | 0.16 | 0.20 | 0.02-2.35 |

TABLE 2

| | | Concentration | RMSEP | | | | | | |
|---|---|---|---|---|---|---|---|---|---|
| Parameter | N | range | 3L-33 | 3L-35A | 3L-35B | 3L-36A | 3L-36B | 3L-37A | 3L-37B |
| Glucose (g/L) | 50 | 1.65-4.28 | 0.29 | 0.18 | 0.18 | 0.21 | 0.20 | 0.33 | 0.11 |
| Lactate (g/L) | 45 | 0.02-1.04 | 0.07 | 0.10 | 0.16 | 0.08 | 0.15 | 0.12 | 0.19 |
| Ammonium (mmol/L) | 48 | 0.78-2.33 | 0.53 | 0.43 | 0.36 | 0.23 | 0.25 | 0.21 | 0.26 |

| | | Concentration | $R^2_P$ | | | | | | |
|---|---|---|---|---|---|---|---|---|---|
| Parameter | N | range | 3L-33 | 3L-35A | 3L-35B | 3L-36A | 3L-36B | 3L-37A | 3L-37B |
| Glucose (g/L) | 50 | 1.65-4.28 | 0.98 | 0.96 | 0.98 | 1.00 | 0.99 | 0.99 | 0.99 |
| Lactate (g/L) | 45 | 0.02-1.04 | 0.90 | 0.96 | 0.90 | 0.94 | 0.84 | 0.85 | 0.75 |
| Ammonium (mmol/L) | 48 | 0.78-2.33 | 0.19 | 0.18 | 0.24 | 0.71 | 0.98 | 0.68 | 0.55 |

Figure 11:
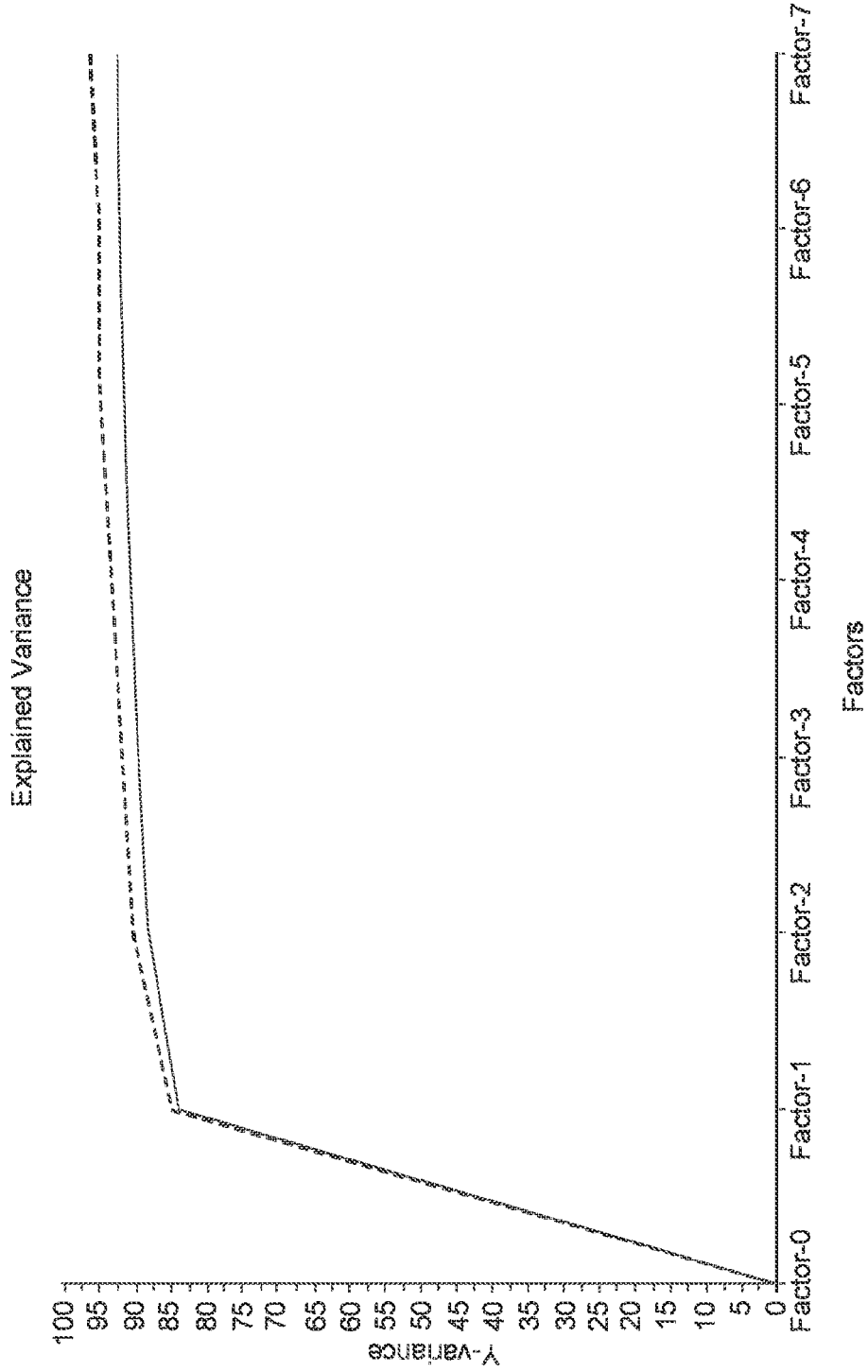
Figure 12:
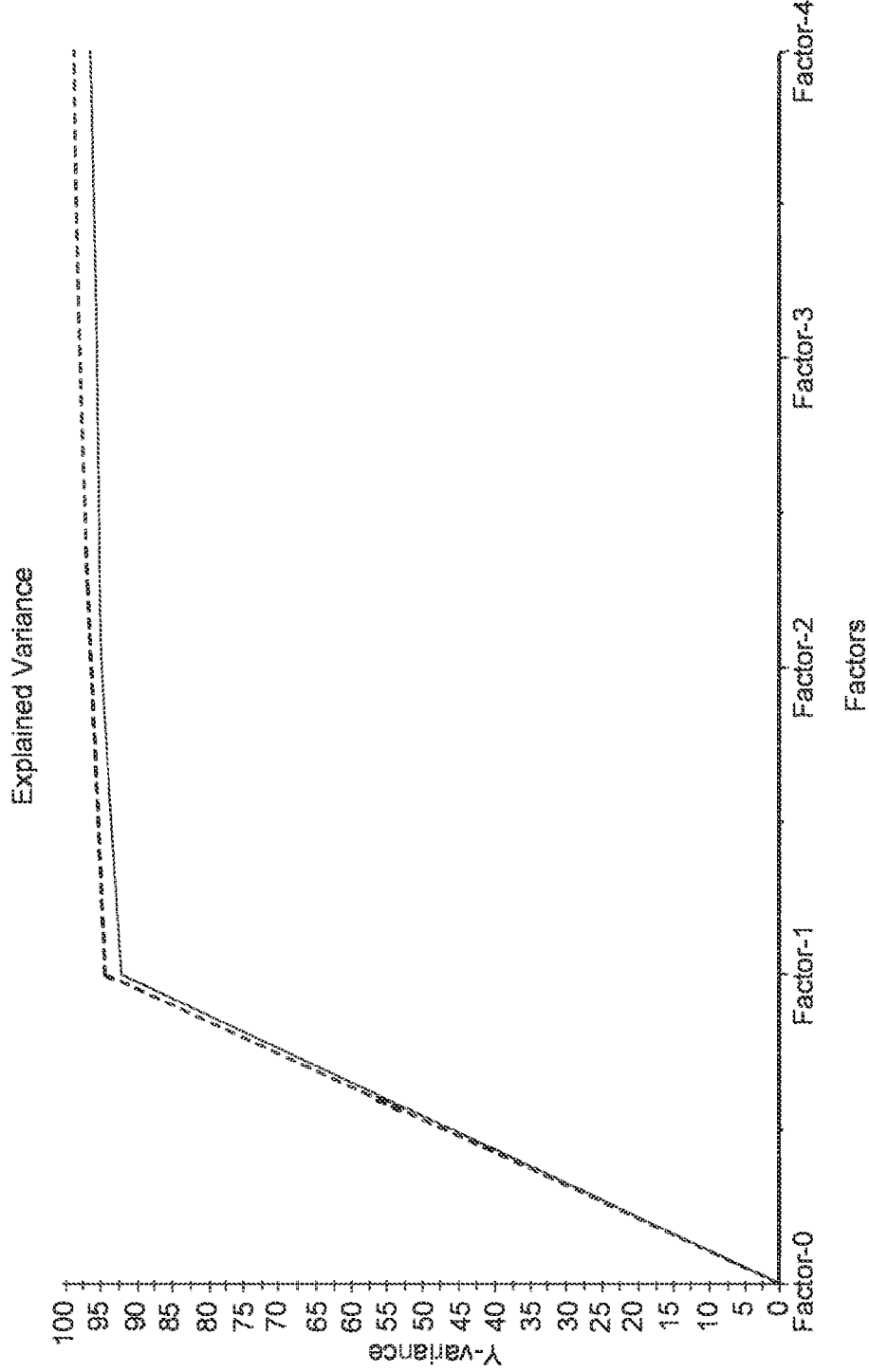
Figure 13:
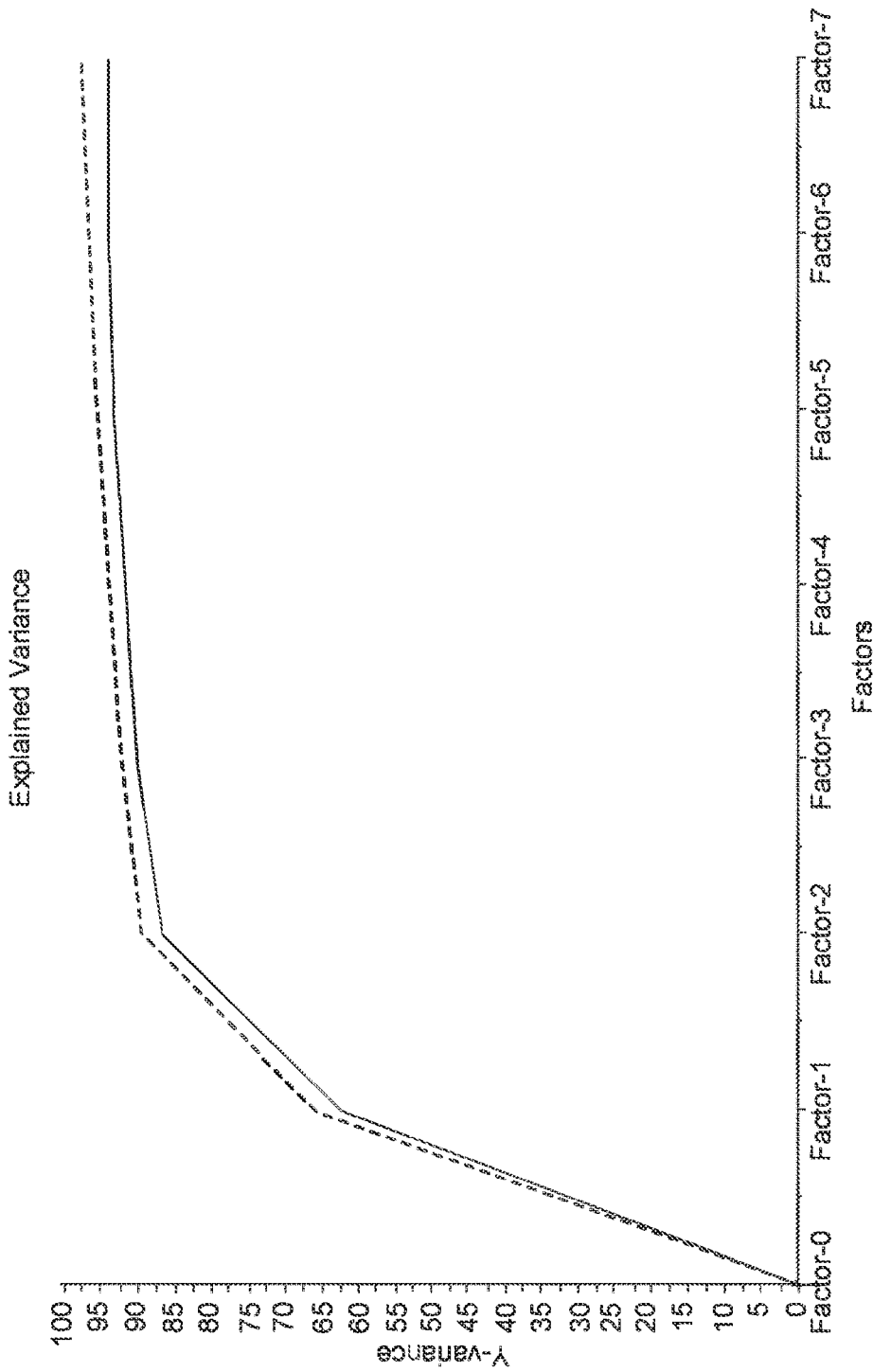
Figure 14:
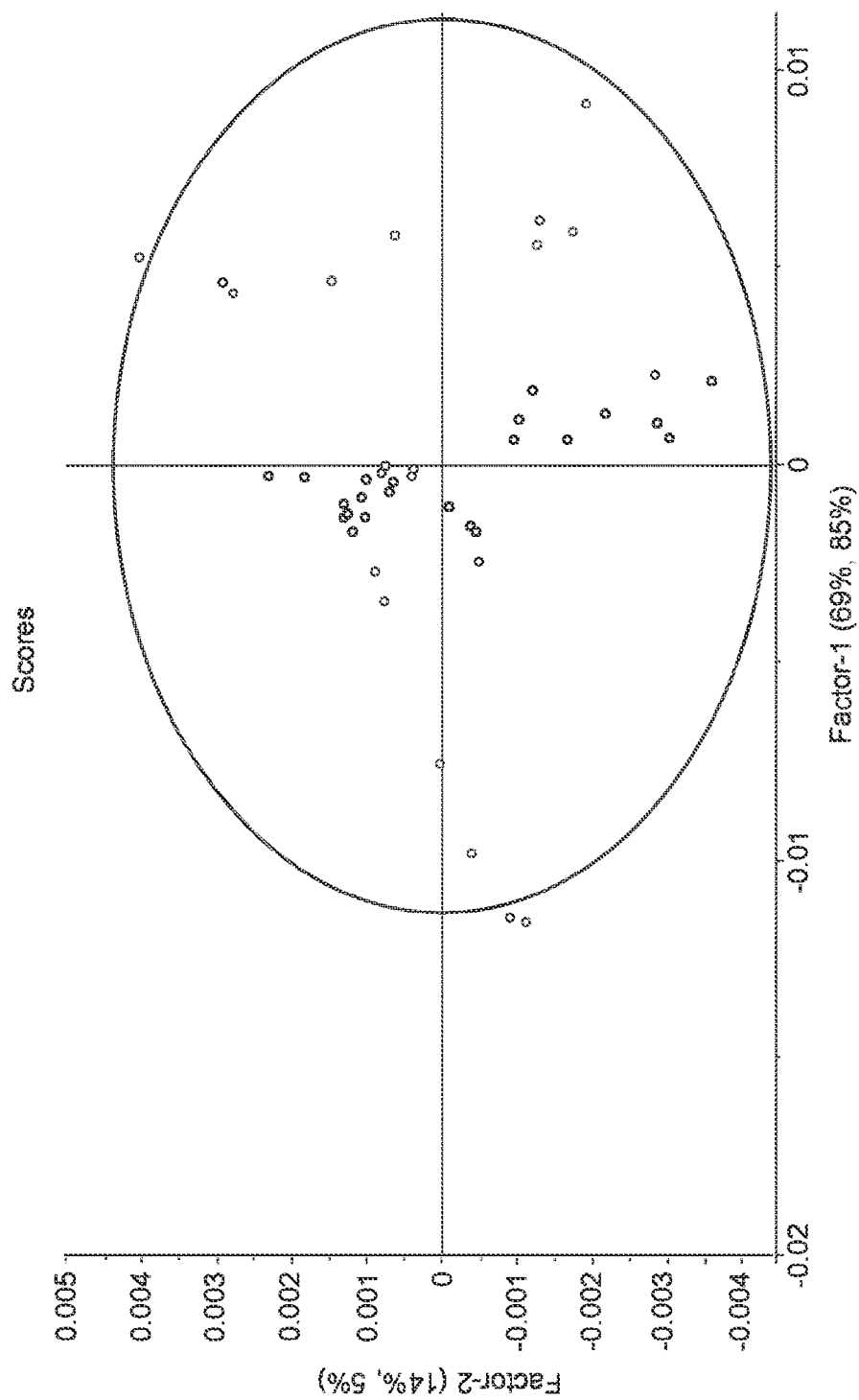
Figure 15:
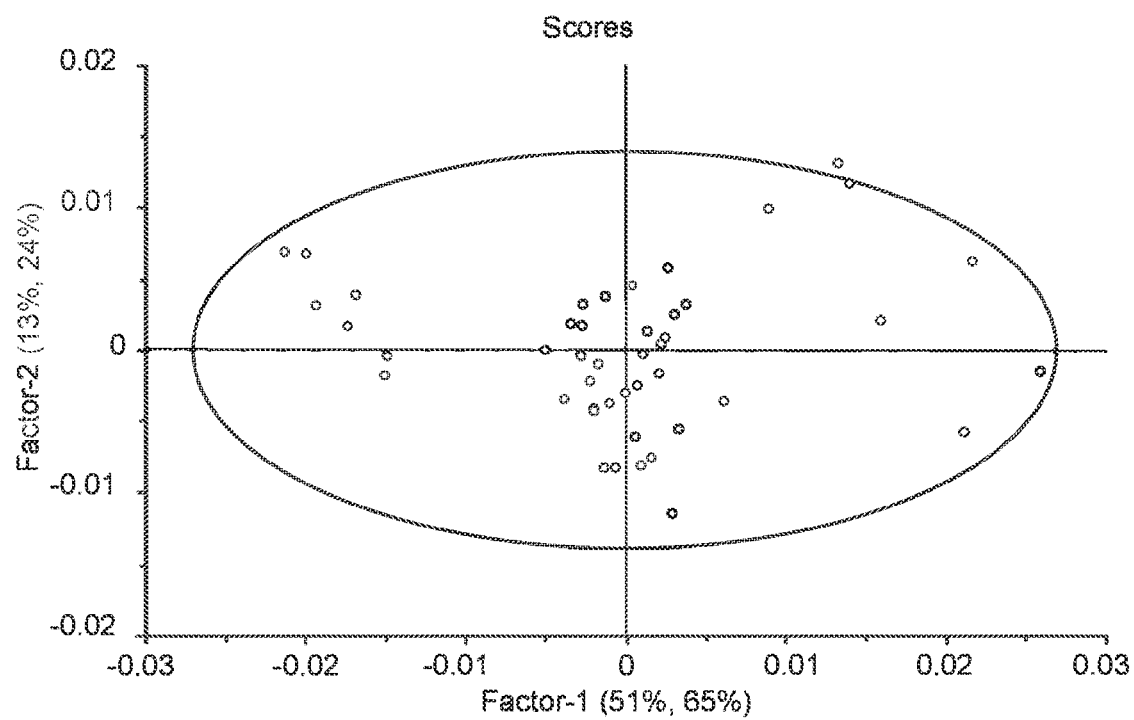
Figure 16:
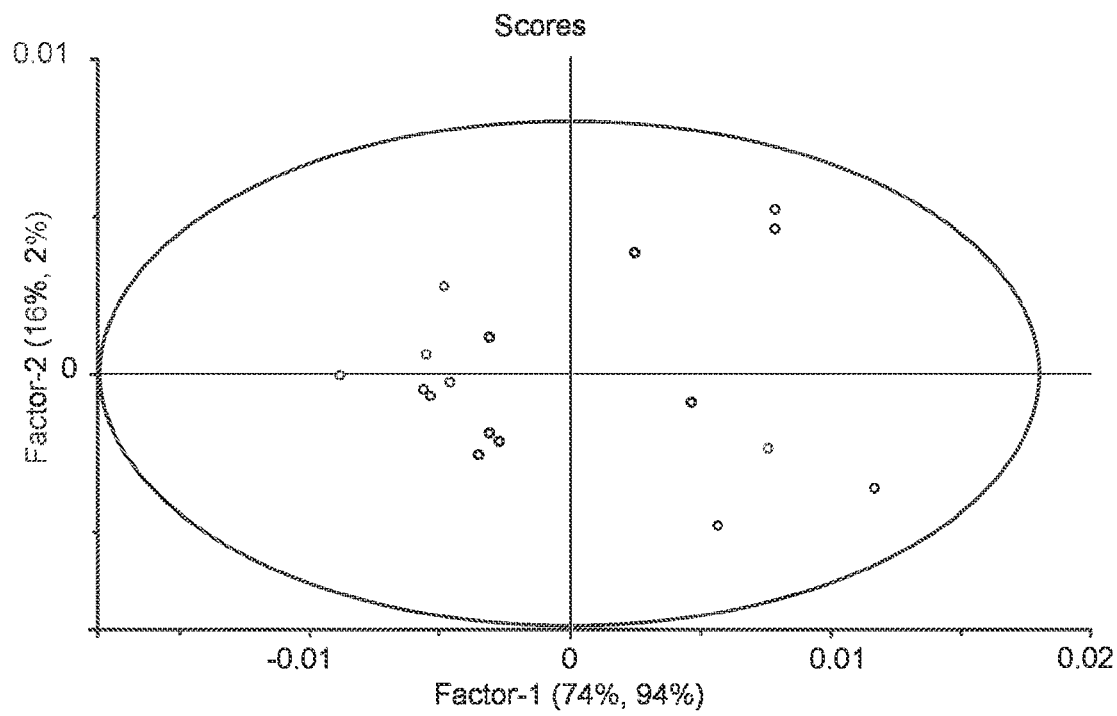

FIGS. 11-13 depict the increasing percentage of the Y variance explained by each additional factor (latent variables) in the model for each of the three modeled molecules. FIGS. 14-16 depict Hotelling's $T^2$ Ellipses for each of the three modeled molecules, which visualizes which points in the calibration set are inside versus outside the 95% confidence interval.

The conclusion from these statistics is that the model is a good fit for glucose, lactate and ammonium within relatively small error relative to the concentration range intended to be measured in the processes.

Model Qualification:

Seven 3 L bioreactors with working volumes ranging from 2-3 L were run for model qualification. An average of 7 samples were taken from each bioreactor run, totaling 50 samples. A small number of samples are missing reference values for lactate and ammonium, this was due to technical issues with the Nova for those particular samples and some zero values. The MSC process for the qualification runs was largely the same as the process used for calibration, with a few small exceptions: different lots of media were used, the qualification runs were performed using gentamicin, and the qualification runs include the addition of antifoam during part of the process. There was a difference in Raman spectra caused by the presence of gentamicin, this was corrected for by chemometrics.

Figure 17:
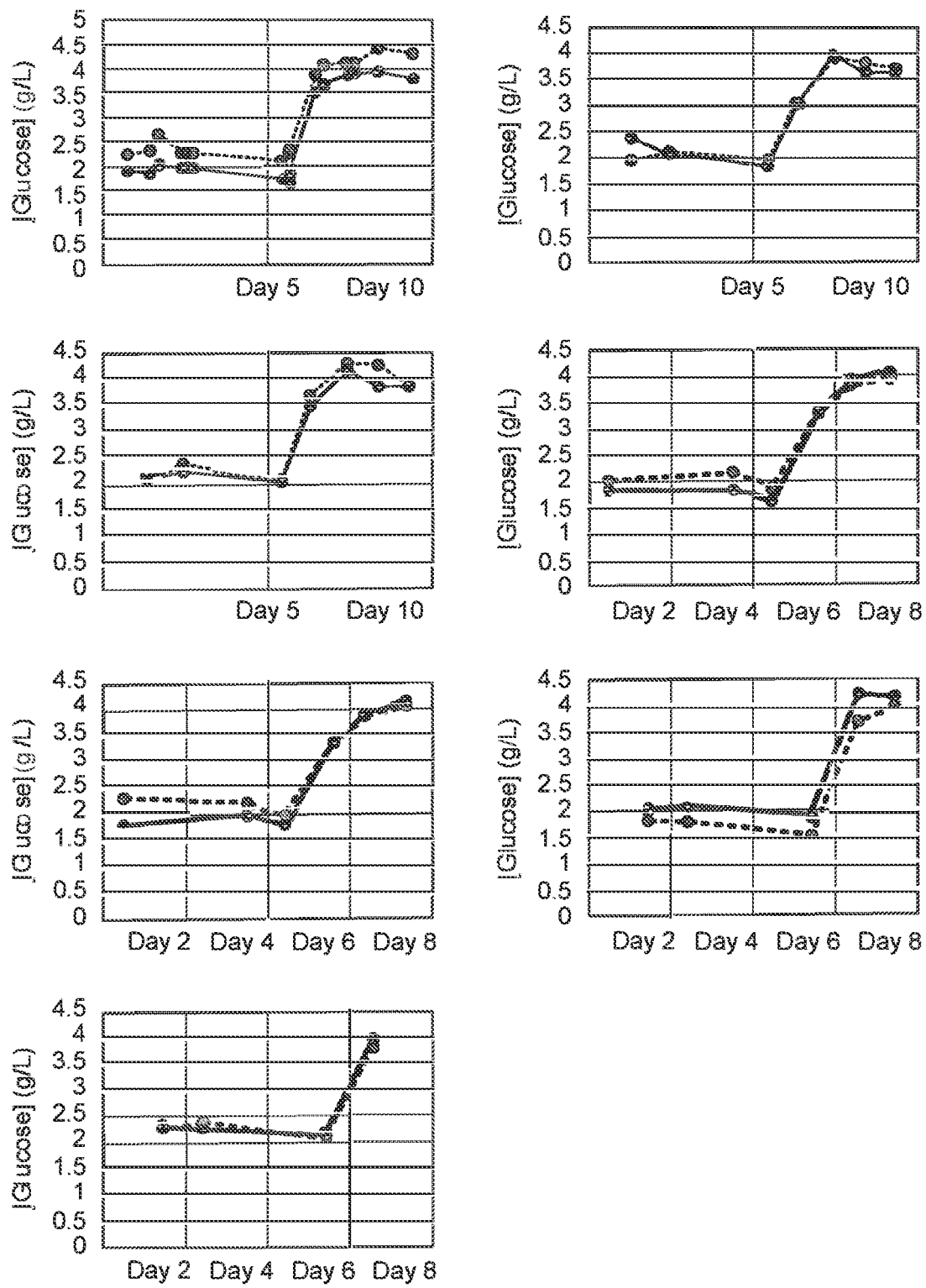
Figure 18:
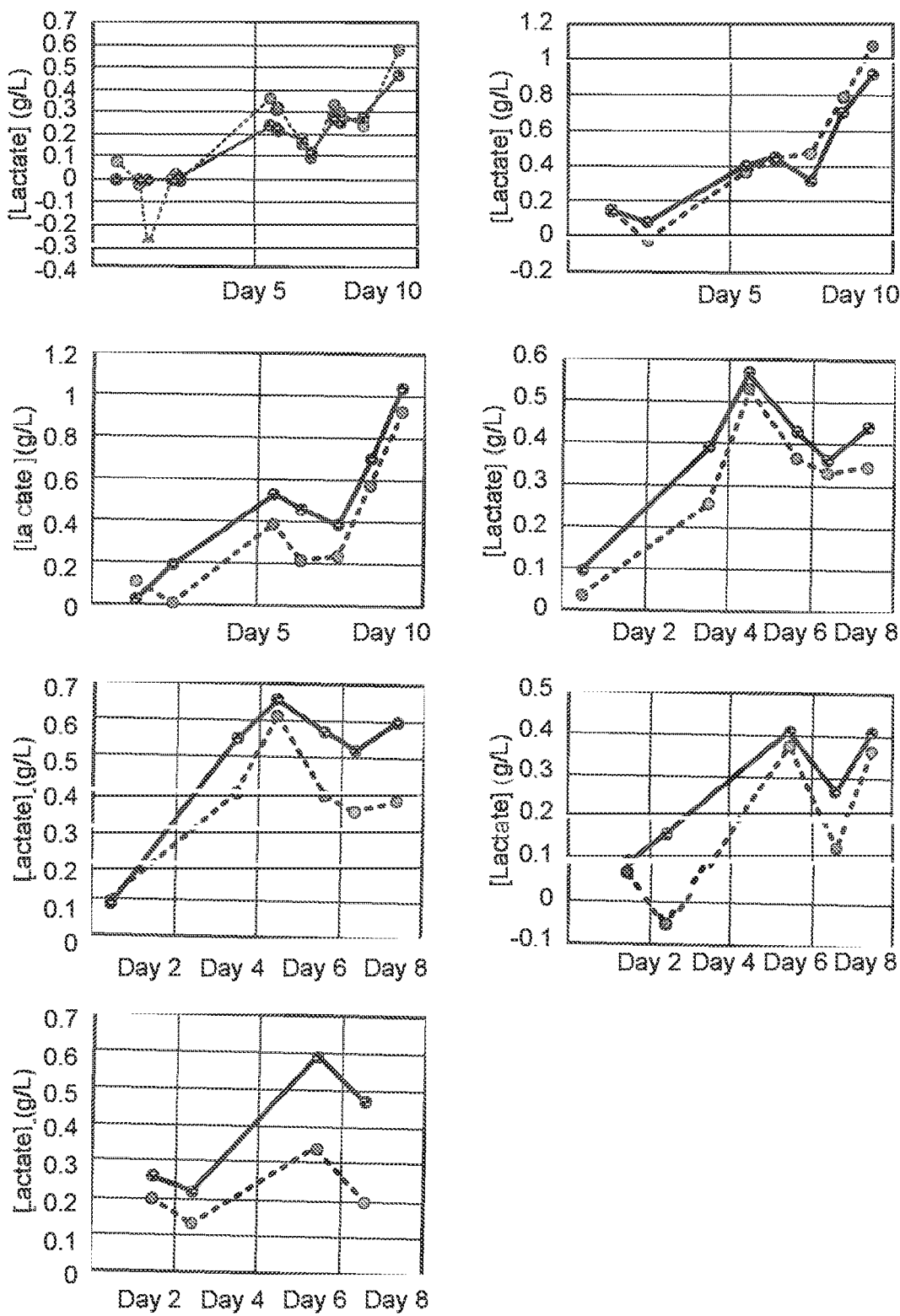
Figure 19:
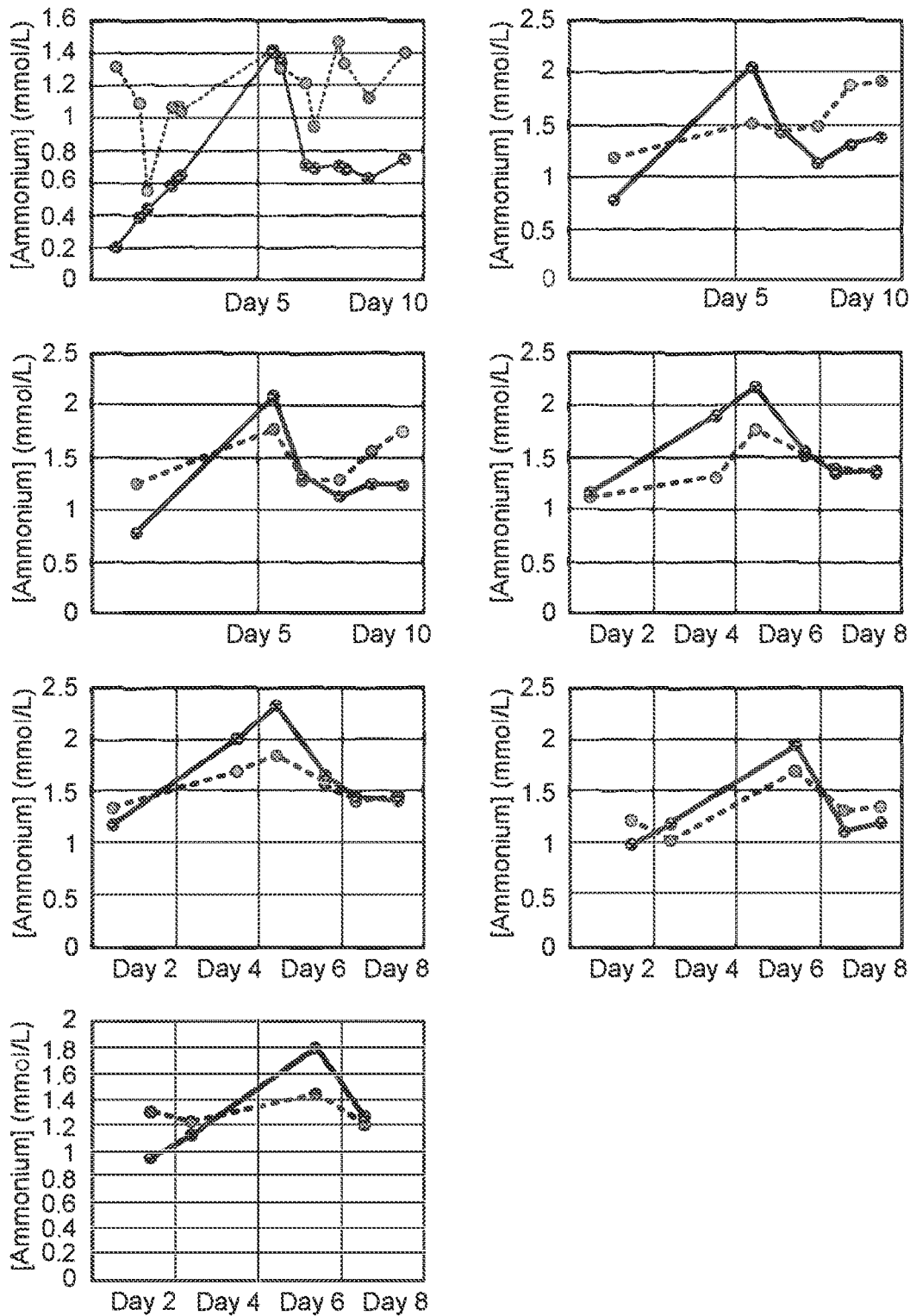

Table 2 shows the statistics from the qualification runs. In six of seven runs, glucose was predicted within the range forecast by the calibration statistics, and in the seventh run the RMSEP value was 0.33, only slightly higher than the RMSECV of 0.29. In six of seven runs, lactate was predicted within the range forecast by the calibration statistics, and in the seventh run the RMSEP value was 0.19, only slightly higher than the RMSECV of 0.17. In all seven runs, ammonium was predicted outside the range forecast by the calibration statistics, although still within 0.5 g/L of the true value, with the exception of the first run. This was likely due to a lower number of ammonium samples in the calibration set. Predictive plots for all seven runs, for all three molecules, can be seen in FIGS. 17-19.

Automated Raman-Driven Control:

One run was performed to test automated Raman-driven control. The frequency of measurements was increased, resulting in a measurement every 10 minutes. Prior to conducting this run, the Raman system was integrated into the bioreactor controller such that it was possible to define a set point for any of the molecules measured via Raman.

Figure 20:
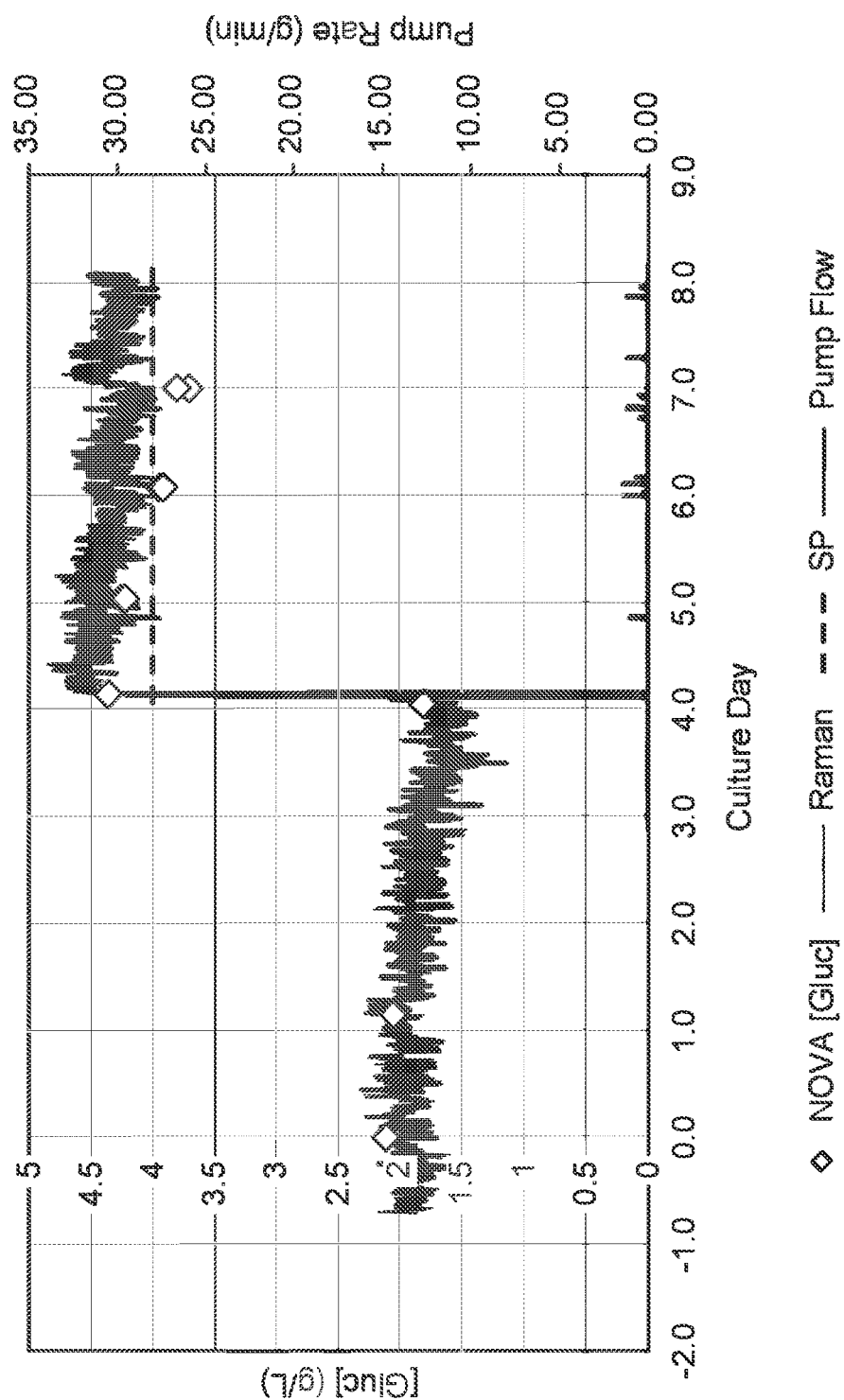

In this run, glucose was chosen to illustrate this. MSCs were initially cultured at 2 g/L glucose FIG. 20. On day 4, the glucose concentration was modified by defining a set point of 4 g/L. The controller was connected to a concentrated glucose feed, which, through a custom feedback function, was automatically pumped into the bioreactor—pump activity is indicated by red spikes in FIG. 20. Throughout the remaining 4 days of culture, glucose was fed in automatically in order to maintain the set point.

The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reacotrs within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBvl3.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cells are for cell therapy.

In one embodiment, the cells may include T cells, or immune cells. For instance, the cells can include B cells, natural killer cells, dendritic cells, tumor infiltrating lymphocytes, monocytes, megakaryocytes, or the like.

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri,* and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii,*), the *Geotrichum* genus (e.g. *Geotrichum fermentans*), *Hansenula polymorpha, Yarrowia lipolytica,* or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina,* or *Ochromonas*), or a plant cell (e.g., cells from monocotyledonous plants (e.g., maize, rice, wheat, or Setaria), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus*. *Bacillus* that can be used is, e.g. the *B. subtilis, B. amyloliquefaciens, B. licheniformis, B. natto,* or *B. megaterium*. In embodiments, the cell is *B. subtilis,* such as *B. subtilis* 3NA and *B. subtilis* 168. *Bacillus* is obtainable from, e.g., the *Bacillus* Genetic Stock Center, Biological Sciences 556, 484 West 12th Avenue, Columbus Ohio 43210-1214.

In one embodiment, the prokaryotic cell is a Gram-negative cell, such as *Salmonella* spp. or *Escherichia coli,* such as e.g., TG1, TG2, W3110, DH1, DHB4, DH5a, HMS174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Samm lung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin,Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostirn, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, traferm in, ziconotide, taltirelin, diboterminalfa, atosiban, becaplerm in, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AID-SVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, romidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OSi, AC-162352, PRX-302, LFn-p24 fusion vaccine (Therapore), EP-1043, S pneumoniae pediatric vaccine, malaria vaccine, Neisseria meningitidis Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™), bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of US2016/0097074:

TABLE I

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |

TABLE I-continued

| Protein Product | Reference Listed Drug |
|---|---|
| Alefacept; recombinant dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated Bacillus Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLARIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venogiobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molelcule, fusion protein, protein vaccine, or peptide as shown in Table 2.

TABLE 2

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel |
| | Lutropin-α | Luveris |
| | Glucagon | GlcaGen |
| | | Geref |
| | Growth hormone releasing hormone (GHRH) | ChiRhoStim (human peptide), SecreFlo (porcine peptide) |
| | Secretin | Thyrogen |
| | Thyroid stimulating hormone (TSH), thyrotropin | |
| Blood Clotting/ Coagulation | Factor VIIa | NovoSeven |
| | Factor VIII | Bioclate, Helixate, Kogenate, |
| | Factor IX | Recombinate, ReFacto |

TABLE 2-continued

Exemplary Products

| Therapeutic Product type | Product | Trade Name |
|---|---|---|
| Factors | Antithrombin III (AT-III) Protein C concentrate | Benefix Thrombate III Ceprotin |
| Cytokine/ Growth factor | Type I alpha-interferon Interferon-αn3 (IFNαn3) Interferon-β1a (rIFN-β) Interferon-β1b (rIFN-β) Interferon-γ1b (IFN γ) Aldesleukin (interleukin 2(IL2), epidermal theymocyte activating factor; ETAF Palifermin (keratinocyte growth factor; KGF) Becaplemin (platelet-derived growth factor; PDGF) Anakinra (recombinant IL1 antagonist) | Infergen Alferon N Avonex, Rebif Betaseron Actimmune Proleukin Kepivance Regranex Anril, Kineret |
| Antibody molecules | Bevacizumab (VEGFA mAb) Cetuximab (EGFR mAb) Panitumumab (EGFR mAb) Alemtuzumab (CD52 mAb) Rituximab (CD20 chimeric Ab) Trastuzumab (HER2/Neu mAb) Abatacept (CTLA Ab/Fc fusion) Adalimumab (TNFα mAb) Etanercept (TNF receptor/Fc fusion) Infliximab (TNFα chimeric mAb) Alefacept (CD2 fusion protein) Efalizumab (CD11a mAb) Natalizumab (integrin α4 subunit mAb) Eculizumab (C5mAb) Muromonab-CD3 | Avastin Erbitux Vectibix Campath Rituxan Herceptin Orencia Humira Enbrel Remicade Amevive Raptiva Tysabri Soliris Orthoclone, OKT3 |
| Other: Fusion proteins/ Protein vaccines/ Peptides | Insulin Hepatitis B surface antigen (HBsAg) HPV vaccine OspA Anti-Rhesus(Rh) immunoglobulin G Enfuvirtide Spider silk, e.g., fibrion | Humulin, Novolin Engerix, Recombivax HB Gardasil LYMErix Rhophylac Fuzeon QMONOS |

In embodiments, the protein is multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T-cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A method of controlling a bioreactor process, comprising:
   supplying a cell culture in a perfusion bioreactor, wherein conditions in the perfusion bioreactor allow for propagation of the cell culture to produce a product;
   measuring one or more parameters within the perfusion bioreactor by a Raman probe to generate Raman spectra,
      wherein one or more parameters are selected from the group consisting of nutrient concentration, waste product concentration, glucose concentration, lactate concentration, glutamate concentration, ammonium concentration, viable cell concentration, total cell concentration, product concentration, process conditions, and product characteristics;
   measuring a mass of the cell culture within the perfusion bioreactor;
   withdrawing one or more of parameter influencing substances from the perfusion bioreactor using one or more ports
      wherein the one or more of parameter influencing substances comprises one or more nutrient medias;
   adding one or more of parameter influencing substances to the perfusion bioreactor using one or more ports; and
   adjusting a flow of one or more of parameter influencing substances to and/or from the perfusion bioreactor in order to maintain one or more parameters within preset limits,
   wherein the flow of one or more of parameter influencing substances into and out of the perfusion bioreactor are adjusted based on the Raman spectra and/or the mass of the cell culture of the perfusion bioreactor.

2. A method as defined in claim 1, wherein the product produced by the cell culture is a protein.

3. A method as defined in claim 1, wherein one or more parameters are measured periodically or continuously.

4. A method as defined in claim 1, wherein one or more of parameter influencing substances are withdrawn from the bioreactor continuously or periodically.

5. A method as defined in claim 1, wherein prior to adjusting the flow of one or more parameter influencing substances, the method comprises:

determining a loop control, based on one or more parameters measured by the Raman probe, that selectively increases or decreases flow of one or more parameter influencing substances to and/or from the bioreactor, wherein one or more parameters are measured at least every hour.

6. A method as defined in claim 1, wherein the flow of one or more of parameter influencing substances to and/or from the perfusion bioreactor are adjusted automatically.

7. A method as defined in claim 1, wherein the method is configured to maintain the cell culture at an average viable cell concentration between about 0.5 million cells per mL to about 35 million cells per mL.

8. A method as defined in claim 1, wherein the perfusion bioreactor has a volume of about 1 L to about 20 L, and the method is configured to measure the mass of the cell culture within the perfusion bioreactor in association with a load cell.

9. A method as defined in claim 1, wherein, when one or more parameters deviate from the preset limit, one or more of parameter influencing substances are maintained so as to minimize fluctuations in another one or more of parameter influencing substances.

10. A method as defined in claim 1, wherein at least one parameter is an amino acid concentration.

11. A method as defined in claim 1, wherein the method is configured to maintain the glucose concentration between about 1 g/L to about 10 g/L.

12. A method as defined in claim 1, wherein the method is configured to maintain the lactate concentration less than about 4.5 g/L.

13. A method as defined in claim 1, wherein the method is configured to maintain the ammonium concentration less than about 0.25 g/L.

14. A method as defined in claim 1, wherein one or more parameters include the process conditions selected from the group consisting of pH, oxygen tension, dissolved carbon dioxide, temperature, agitation conditions, alkali condition, pressure, and foam levels.

15. A method as defined in claim 1, wherein one or more parameter influencing substances include a nutrient media comprising a carbohydrate source, an amino acid, a vitamin, a lipid, a protein, a peptide, or mixtures thereof.

16. A method as defined in claim 1, wherein the product characteristics comprise glycosylation profile and/or charge variant profile.

17. A method as defined in claim 1, wherein the withdrawing of one or more of parameter influencing substances form the perfusion bioreactor and/or the adding of one or more of parameter influencing substances to the perfusion bioreactor is controlled by a controller that regulates a respective pump.

18. A method as defined in claim 1, wherein the withdrawing of one or more of parameter influencing substances form the perfusion bioreactor is effectuated using a dip tube.

19. A method as defined in claim 1, wherein the perfusion bioreactor has a volume of at least 10L and wherein the glucose concentration is maintained at a desired set point by way of the cell culture fluids being continuously removed and replenished based on measurements by the Raman probe.

20. A method as defined in claim 1, wherein the method is configured to maintain the cell culture at an average viable cell concentration of at least 30 million cells per mL and wherein one or more parameters deviate from a desired set point within ±2.0 RMSEP.

* * * * *